United States Patent [19]

Moore et al.

[11] Patent Number: 5,952,298

[45] Date of Patent: *Sep. 14, 1999

[54] CRYPTOPHYCINS

[75] Inventors: Richard E. Moore, Honolulu, Hi.; Charles D. Smith, Feasterville, Pa.; Gregory M.L. Patterson; Susan L. Mooberry, both of Honolulu, Hi.; Thomas H. Corbett, Grosse Point; Frederick A. Valeriote, Shelby Township, both of Mich.; Trimurtulu Golakoti, Honolulu, Hi.

[73] Assignees: The University Of Hawaii, Honolulu, Hi.; Wayne State University, Detroit, Mich.

[ * ] Notice: This patent is subject to a terminal disclaimer.

[21] Appl. No.: 08/482,141

[22] Filed: Jun. 7, 1995

Related U.S. Application Data

[63] Continuation-in-part of application No. PCT/US94/14740, Dec. 21, 1994, which is a continuation-in-part of application No. 08/249,955, May 27, 1994, abandoned, which is a continuation of application No. 08/172,632, Dec. 21, 1993, abandoned.

[51] Int. Cl.⁶ .............................. A61K 38/12; C07K 7/52
[52] U.S. Cl. ................ 514/9; 514/11; 930/270; 530/317
[58] Field of Search ............ 514/9, 1; 930/270; 530/317

[56] References Cited

U.S. PATENT DOCUMENTS 4,946,835  8/1990  Hirsch et al. .......................... 514/183

OTHER PUBLICATIONS

Smith et al., Cancer Res. vol. 54 (Jul. 1994) 3779–84.
Trinurtulu et al. JACS vol. 116 4729–37 (1994).
Kobayoshi et al., Chem. Pharm Bull. vol. 42(10) Oct. 1994 2196–98.
Goodman & Gilman "The Pharmacological Basis of Therapeutics" 6th Ed. (Macmillan Publishing) pp. 1249–1255; 1738–1740.

*Primary Examiner*—Cecilia J. Tsang
*Assistant Examiner*—Bennett Celsa
*Attorney, Agent, or Firm*—Gray Cary Ware & Freidenrich LLP; Stephen E. Reiter; Stanley E. Kim

[57] ABSTRACT

A cryptophycin compound is provided having the structure:

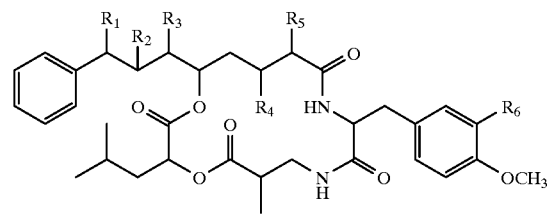

Further provided are methods for producing novel cryptophycins from the Nostoc sp. of blue-green algae (cyanobacteria). Pharmaceutical compositions comprising novel cryptophycins are also provided, as are methods for using cryptophycins to inhibit the proliferation of hyperproliferative cells. Further provided are methods for using cryptophycins to inhibit the proliferation of hyperproliferative cells with drug resistant phenotypes, and to treat pathological conditions, such as neoplasia.

5 Claims, 4 Drawing Sheets

Time of Incubation (hr)

CRYPTOPHYCINS

This is a continuation-in-part of copending International application Serial No. PCT\US94\14740 filed Dec. 21, 1994, which is a continuation-in-part of application Ser. No. 08/249,955 filed May 27, 1994, now abandoned, which is a continuation of application Ser. No. 08/172,632, filed Dec. 21, 1993, now abandoned. These patent applications are hereby incorporated by reference.

This invention was made in part with U.S. Government support under Grant No. CA12623 from The National Cancer Institute, Department of Health and Human Services. Accordingly, the U.S. Government may have certain rights in this invention.

BACKGROUND OF THE INVENTION

Neoplastic diseases, characterized by the proliferation of cells not subject to the normal control of cell growth, are a major cause of death in humans. Clinical experience in cancer chemotherapy has demonstrated that new and more effective drugs are desirable to treat these diseases. Such clinical experience has also demonstrated that drugs which disrupt the microtubule system of the cytoskeleton can be effective in inhibiting the proliferation of neoplastic cells.

The microtubule system of eucaryotic cells is a major component of the cytoskeleton and is in a dynamic state of assembly and disassembly; that is, heterodimers of tubulin are polymerized and form microtubules. These microtubules play a key role in the regulation of cell architecture, metabolism, and division and their dynamic character is essential to their normal function in the cell. For example, with respect to cell division, microtubules are created, that is, polymerized from tubulin, to form the mitotic spindle. When the mitotic spindle's use has been fulfilled, the microtubules contained in it are subsequently depolymerizd. Disrupting either the polymerization or depolymerization of microtubules in the cell can inhibit mitosis, and thereby cell proliferation.

An agent which could prevent a cell from proliferating by inhibiting a cells' microtubule dynamic state would be useful in treating cancer, a disease characterized by cells proliferating at abnormally high rates. Indeed, such agents comprise some of the most effective cancer chemotherapeutic agents in clinical use today.

These anti-mitotic agents or poisons are classified into three groups based on their molecular mechanism of action. The first group, including colchicine and colcemid, inhibit the formation of microtubules by sequestering tubulin. The second group, including vinblastine and vincristine, induce the formation of paracrystalline aggregates of tubulin. These two agent's action preferentially inhibits the proliferation of hyperproliferating cells by disrupting mitotic spindle microtubules. The third group, including taxol, promotes the polymerization of tubulin, thereby disrupting the dyanmic state of microtubule polymerization and depolymerization.

However, an agent's having activity as an antimitotic poison does not lead to the conclusion that this agent would evince such activity in a tumor cell nor in a tumor cell with a drug-resistant phenotype. For example, vinca alkaloids such as vinblastine and vincristine are effective against some neoplastic cells and tumors, yet they lack activity against some drug-resistant tumors and cells. One basis for a neoplastic cell displaying drug resistance (DR) or multiple-drug resistance (MDR) is through the over-expression of P-glycoprotein. Compounds which are poor substrates for transport of P-glycoprotein should be useful in circumventing such a MDR phenotype.

Accordingly, the exhibition of the DR or MDR phenotype by many tumor cells and the clinically proven mode of action of anti-microtubule agents against neoplastic cells necessitates the development of anti-microtubule agents cytotoxic to non-drug resistant neoplastic cells as well as cytotoxic to neoplastic cells with a drug resistant phenotype.

BACKGROUND ART

Selected cryptophycin compounds, dioxa-diazacyclohexadecenetetrones isolated or synthesized from isolates from the blue-green algae (cyanobacteria) of the genus Nostoc, were characterized as antifungal agents with activity toward filamentous fungi, specifically the Aspergillus, Penicillium and Phoma species thereof; however, their mechanism of action was unknown. Five cryptophycin compounds, herein designated Cryptophycins 1, 3, 5, 13 and 15, were disclosed in U.S. Pat. Nos. 4,946,835, 4,845,085, 4,845,086, and 4,868,208, such compounds either having been isolated from a strain of Nostoc sp. designated MB 5357 or having been synthesized from such an isolated compound.

SUMMARY OF THE INVENTION

The present invention provides novel cryptophycin compounds having the following structure:

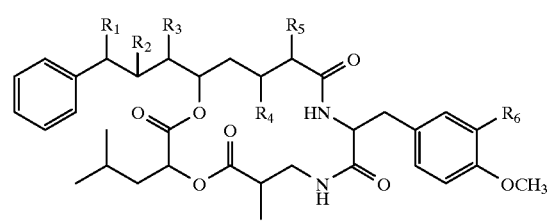

Wherein
$R_1$ is H or a halogen;
$R_2$ is H, an oxygen of a ketone or OH; or
$R_1$ and $R_2$ may be taken together to form an epoxide ring;
or $R_1$ and $R_2$ may be taken together to form an episulfide ring;
$R_3$ is H, or a lower alkyl group;
$R_4$ is H or OH;
$R_5$ is H or OH; or
$R_4$ and $R_5$ may be taken together to form a second bond;
$R_6$ is H or a halogen;
With the following proviso
when $R_1$ and $R_2$ are taken together to form an epoxide group, $R_4$ and $R_5$ are taken together to form a second bond and $R_6$ is chlorine, $R_3$ is not methyl.

Further provided by the present invention are methods for producing novel cryptophycin compounds from the Nostoc sp. of blue-green algae (cyanobacteria). Pharmaceutical compositions comprising the new cryptophycin compounds are also provided by the present invention, as are methods for using novel cryptophycin compounds to inhibit the proliferation of normal and hyperproliferative mammalian cells. The present invention also provides methods for using novel cryptophycin compounds to inhibit the proliferation of hyperproliferative mammalian cells with drug-resistant phenotypes, including those with multiple drug-resistant phenotypes. Furthermore, methods of using novel cryptophycin compounds to treat pathological conditions, such as neoplasia, are provided by the present invention.

DETAILED DESCRIPTION OF THE INVENTION

Figure 1:
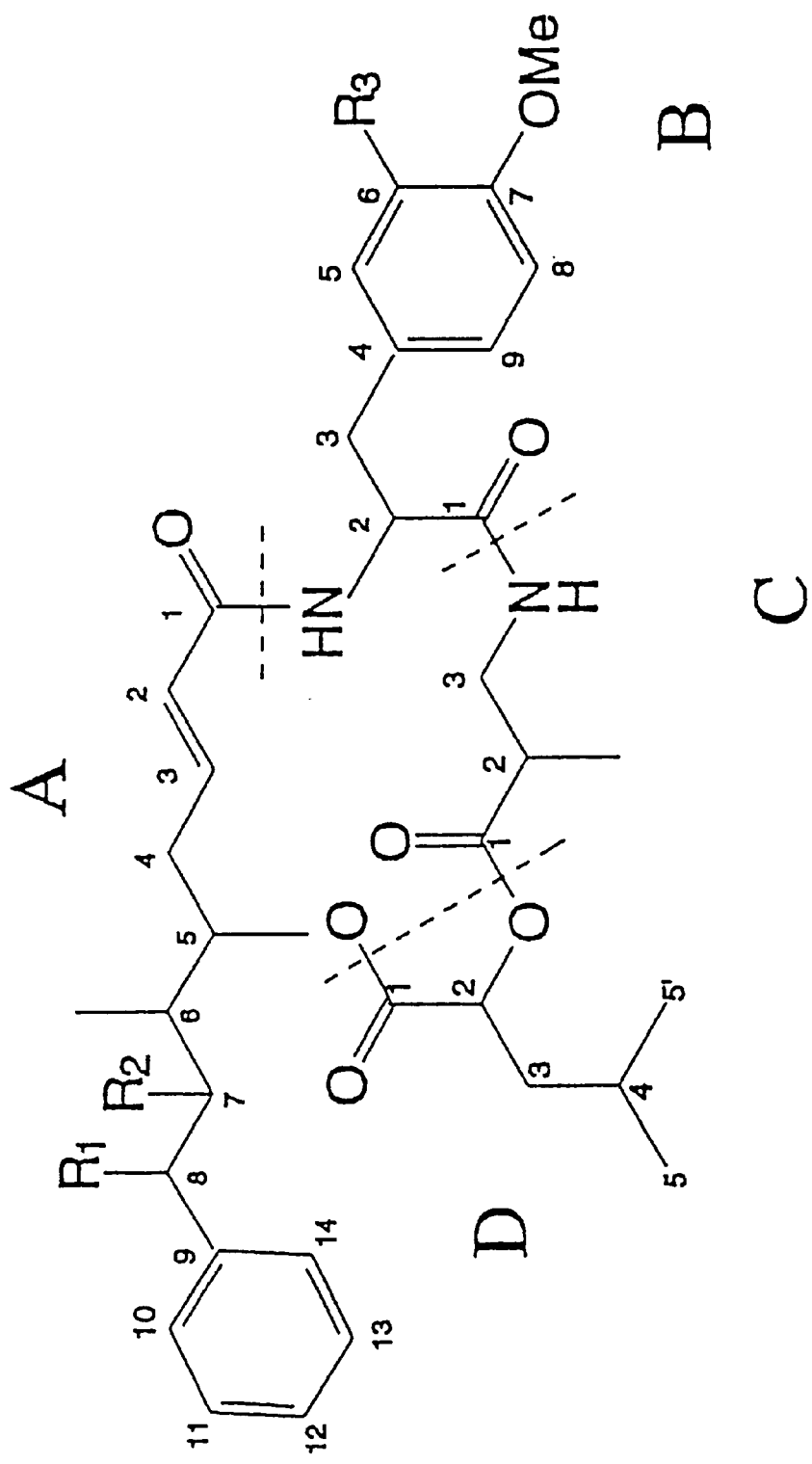
FIG. 1 provides a general structure of selected cryptophycin compounds of the present invention and a numbering system for the hydroxy acid units A and D and two amino acid units B and C in the selected embodiments.

The present invention provides novel cryptophycin compounds having the following structure:

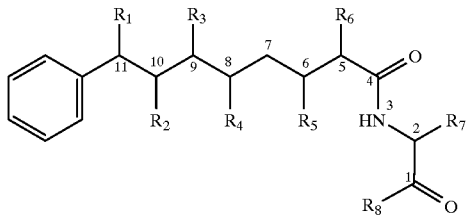

Wherein
$R_1$ is H, OH, a halogen, O of a ketone group, $NH_2$, SH, a lower alkoxyl group or a lower alkyl group;
$R_2$ is H, OH, O of a ketone group, $NH_2$, SH, a lower alkoxyl group or a lower alkyl group; or
$R_1$ and $R_2$ may be taken together to form an epoxide ring, an aziridene ring, a sulfide ring or a second bond between $C_{10}$ and $C_{11}$; or
$R_1$ and $R_4$ may be taken together to form a tetrahydrofuran ring;
$R_3$ is H or a lower alkyl group;
$R_4$ is OH, a lower alkanoyloxy group or a lower α-hydroxy alkanoyloxy group;
$R_5$ is H or an OH group;
$R_6$ is H; or
$R_5$ and $R_6$ may be taken together to form a second bond between $C_5$ and $C_6$;
$R_7$ is a benzyl, hydroxybenzyl, methoxybenzyl, halohydroxybenzyl, dihalohydroxybenzyl, halomethoxybenzyl, or dihalomethoxybenzyl group;

$R_8$ is OH, a lower β-amino acid wherein $C_1$ is bonded to N of the β-amino acid, or an esterified lower β-amino acid wherein $C_1$ is bonded to N of the esterified lower β-amino acid group;
$R_4$ and $R_8$ may be taken together to form a didepsipeptide group consisting of a lower β-amino acid bonded to a lower α-hydroxy alkanoic acid; and
$R_5$ and $R_8$ may be taken together to form a didepsipeptide group consisting of a lower β-amino acid bonded to a lower α-hydroxy alkanoic acid; and with the following provisos:
$R_1$ is H, a lower alkyl group, or a lower alkoxyl group only if $R_2$ is OH, O of a ketone group, $NH_2$, SH;
$R_2$ is H, a lower alkyl group, or a lower alkoxyl group only if $R_1$ is OH, O of a ketone group, $NH_2$, SH;
when $R_1$ is OH, $R_2$ is OH, $R_3$ is methyl, $R_5$ and $R_6$ are taken together to form a second bond between $C_5$ and $C_6$, $R_4$ and $R_8$ are taken together to form the didepsipeptide group with the structure X:

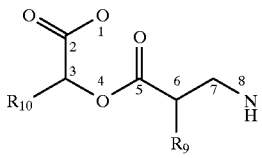

wherein $O_1$ of X corresponds to $R_4$, $N_8$ of X corresponds to $R_8$, $R_9$ is methyl, and $R_{10}$ is isobutyl, $R_7$ is not 3-chloro4-methoxybenzyl;

when $R_1$ and $R_2$ are taken together to form an epoxide ring, $R_3$ is methyl, $R_5$ and $R_6$ are taken together to form a second bond between $C_5$ and $C_6$, $R_4$ and $R_8$ are taken together to form a didepsipeptide with the structure X, $R_9$ is methyl, and $R_{10}$ is isobutyl, $R_7$ is not 3-chloro-4-methoxybenzyl;

when $R_1$ and $R_2$ are taken together to form a second bond between $C_{10}$ and $C_{11}$, $R_3$ is methyl, $R_5$ and $R_6$ are taken together to form a second bond between $C_5$ and $C_6$, $R_4$ and $R_8$ are taken together to form a didepsipeptide with the structure X, $R_9$ is methyl, and $R_{10}$ is isobutyl, $R_7$ is not 3-chloro-4-methoxybenzyl; and when $R_1$ and $R_2$ are taken together to form an epoxide group, $R_3$ is methyl, $R_5$ and $R_6$ are taken together to form a second bond between $C_5$ and $C_6$, $R_4$ is bonded to the carboxy terminus of leucic acid, and $R_8$ is bonded to the nitrogen terminus of either 3-amino-2-methylpropionic acid or 3-amino-2-methylpropionic acid methyl ester, $R_7$ is not 3-chloro-4-methoxybenzyl.

The invention further provides cryptophycin compounds wherein at least one of the groups attached to $C_2$, $C_8$, $C_9$, $C_{10}$, and $C_{11}$ has R stereochemistry. In a further embodiment of the invention, at least one of the groups attached to $C_2$, $C_8$, $C_9$, $C_{10}$, and $C_{11}$ has S stereochemistry.

The invention further provides cryptophycin compounds in accordance with the above structure where the structure of the didepsipeptide that is formed when $R_4$ or $R_5$ is taken together with $R_8$ is the following structure X:

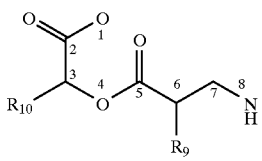

wherein $O_1$ of X corresponds to $R_4$ or $R_5$, $N_8$ of X corresponds to $R_8$, $R_9$ is H or a lower alkyl group, and $R_{10}$ is H or a lower alkyl group.

As used herein, "lower β-amino acid" means any β-amino acid having three to eight carbons and includes linear and non-linear hydrocarbon chains; for example, 3-amino-2-methylpropionic acid. As used herein, "esterified lower β-amino acid" means any β-amino acid having three to five carbons where the hydrogen of the carboxylic acid group is substituted with a methyl group; for example, 3-amino-2-methylpropionic acid methyl ester. As used herein, "lower alkanoyloxy group" means an alkanoyloxy group of one to seven carbons and includes linear and non-linear hydrocarbon chains. As used herein, "lower α-hydroxyalkanoyloxy group" means an α-hydroxyalkanoyloxy group of two to seven carbons and includes linear and non-linear hydrocarbon chains; for example, 2-hydroxy-4-methylvaleric acid.

As used herein, "lower alkoxyl group" means any alkyl group of one to five carbons bonded to an oxygen atom. As used herein, "lower alkyl group" means an alkyl group of one to five carbons and includes linear and non-linear hydrocarbon chains.

As used herein, "epoxide ring" means a three-membered ring whose backbone consists of two carbons and an oxygen atom. As used herein, "aziridine ring" means a three-membered ring whose backbone consists of two carbons and a nitrogen atom. As used herein, "sulfide ring" means a three-membered ring whose backbone consists of two carbons and a sulfur atom.

As used herein, "halogen" refers to those members of the group on the periodic table historically known as the halogens. Methods of halogenation include, but are not limited to, the addition of hydrogen halides, substitution at high temperature, phohalogenation, etc., and such methods are known to those of ordinary skill in the art. [1,2]

An example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 2, is the following:

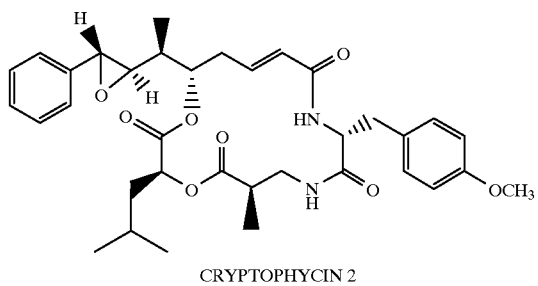

CRYPTOPHYCIN 2

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 4, is the following:

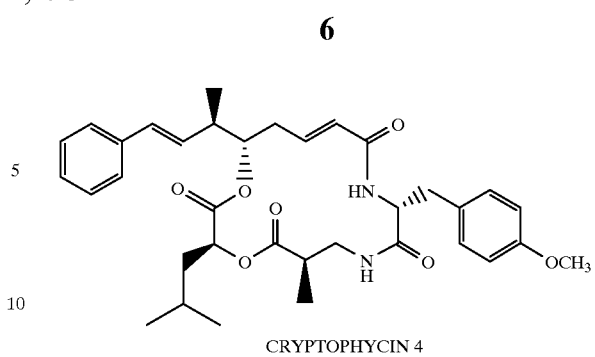

CRYPTOPHYCIN 4

A further example of a novel cryptophycin compound of the present invention is when $R_1$ and $R_4$ are taken together to form a tetrahydrofuran ring, $R_2$ is an OH group, $R_3$ is methyl, $R_5$ and $R_6$ are taken together to form a second bond between $C_5$ and $C_6$ such that there is a double bond, $R_7$ is 3-chloro4-methoxybenzyl, and $R_8$ is a (2-carbomethoxypropyl)amino group. The structure of this cryptophycin compound, Cryptophycin 6, is the following:

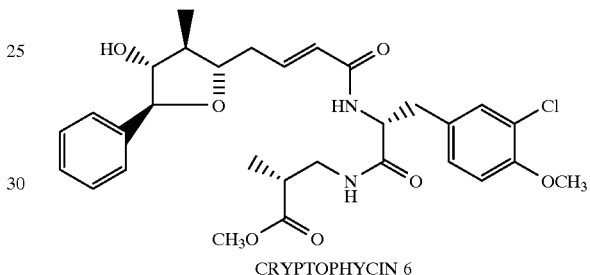

CRYPTOPHYCIN 6

A further example of a novel cryptophycin compound of the present invention is when $R_1$ and $R_4$ are taken together to form a tetrahydrofuran ring, $R_2$ and $R_8$ are OH groups, $R_3$ is methyl, $R_5$ and $R_6$ are taken together to form a second bond between $C_5$ and $C_6$ such that there is a double bond, and $R_7$ is 3-chloro-4-methoxybenzyl. The structure of this cryptophycin compound, Cryptophycin 7, is the following:

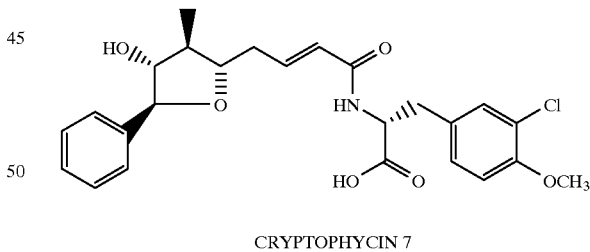

CRYPTOPHYCIN 7

A further example of a novel cryptophycin compound of the present invention is when $R_1$ is a chloro group, $R_2$ is an OH group, $R_3$ is methyl, $R_5$ and $R_6$ are taken together to form a second bond between $C_5$ and $C_6$ such that there is a double bond, $R_7$ is 3-chloro4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 8, is the following:

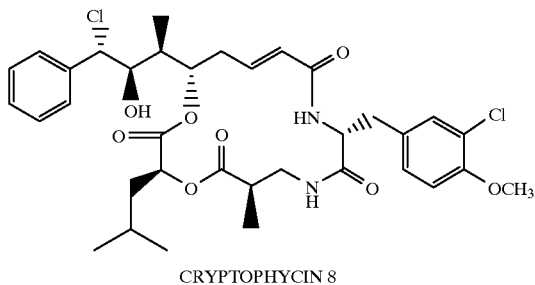

CRYPTOPHYCIN 8

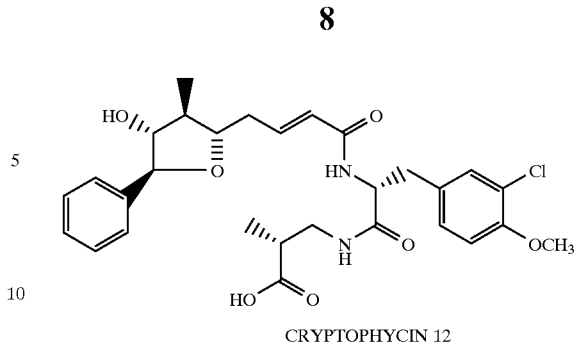

CRYPTOPHYCIN 12

A further example of a novel cryptophycin compound of the present invention is when $R_1$ is a methoxy group, $R_2$ is an OH group, $R_3$ is methyl, $R_5$ and $R_6$ are taken together to form a second bond between $C_5$ and $C_6$ such that there is a double bond, $R_7$ is 3-chloro4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 9, is the following:

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_4$ is an OH group, $R_5$ and $R_6$ are taken together to form a second bond between $C_5$ and $C_6$ such that there is a double bond, $R_7$ is 3-chloro-4-methoxybenzyl, and $R_8$ is a (2-carboxypropyl)amino group. The structure of this cryptophycin compound, Cryptophycin 14, is the following:

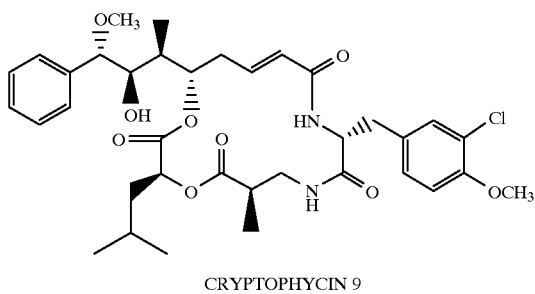

CRYPTOPHYCIN 9

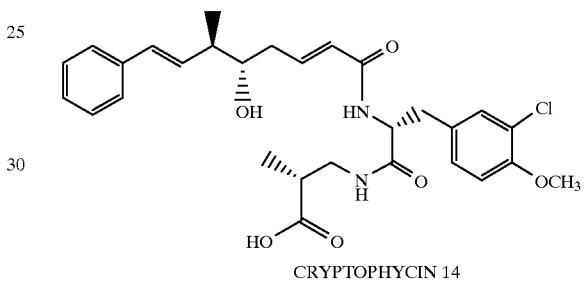

CRYPTOPHYCIN 14

A further example of a novel cryptophycin compound of the present invention is when $R_1$ is a methoxy group, $R_2$ and $R_4$ are OH groups, $R_3$ is methyl, $R_5$ and $R_6$ are taken together to form a second bond between $C_5$ and $C_6$ such that there is a double bond, $R_7$ is 3-chloro-4-methoxybenzyl, and $R_8$ is a (2-carboxypropyl)amino group. The structure of this cryptophycin compound, Cryptophycin 10, is the following:

A further example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 3-chloro-4-hydroxybenzyl, and $R_4$ and $R_8$ are taken together to form the didepsipeptide with the structure X where $R_9$ is methyl and $R_{10}$ is isobutyl. The structure of this cryptophycin compound, Cryptophycin 16, is the following:

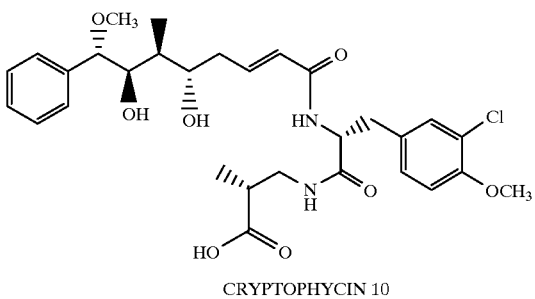

CRYPTOPHYCIN 10

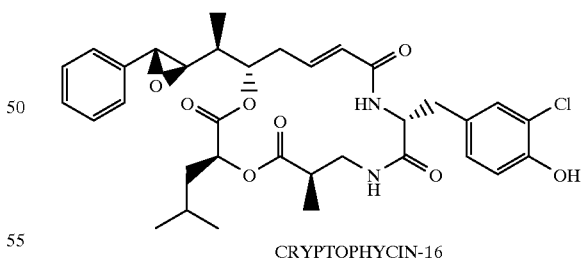

CRYPTOPHYCIN-16

A further example of a novel cryptophycin compound of the present invention is when $R_1$ and $R_4$ are taken together to form a tetrahydrofuran ring, $R_2$ is an OH group, $R_3$ is methyl, $R_5$ and $R_6$ are taken together to form a second bond between $C_5$ and $C_6$ such that there is a double bond, $R_7$ is 3-chloro4-methoxybenzyl, and $R_8$ is a (2-carboxypropyl) amino group. The structure of this cryptophycin compound, Cryptophycin 12, is the following:

A further example of a novel cryptophycin compound of the present invention is when $R_1$ and $R_2$ are taken together to form a second bond between $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 3-chloro-4-hydroxybenzyl, and $R_4$ and $R_8$ are taken together to form the didepsipeptide with the structure X where $R_9$ is methyl and $R_{10}$ is isobutyl. The structure of this cryptophycin compound, Cryptophycin 17, is the following:

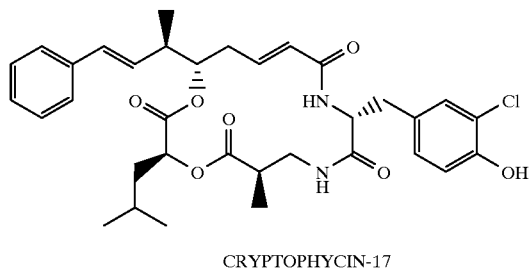

CRYPTOPHYCIN-17

A further example of a novel cryptophycin compound of the present invention is when $R_1$ and $R_2$ are taken together to form a second bond between $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 3-chloro4-methoxybenzyl, and $R_4$ and $R_8$ are taken together to form the didepsipeptide with the structure X where $R_9$ is methyl and $R_{10}$ is sec-butyl. The structure of this cryptophycin compound, Cryptophycin 18, is the following:

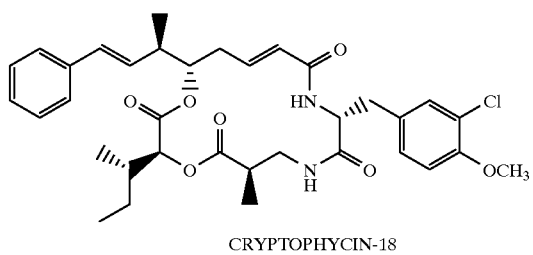

CRYPTOPHYCIN-18

A further example of a novel cryptophycin compound of the present invention is when $R_1$ and $R_2$ are taken together to form a second bond between $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 3-chloro-4-methoxybenzyl, and $R_4$ and $R_8$ are taken together to form the didepsipeptide with the structure X where $R_9$ is methyl and $R_{10}$ is isopropyl. The structure of this cryptophycin compound, Cryptophycin 19, is the following:

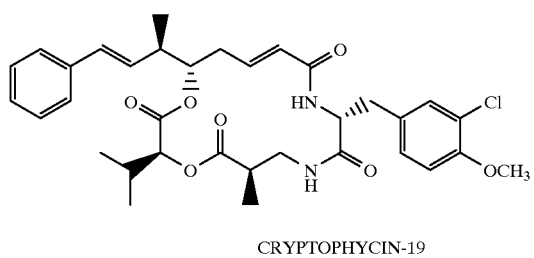

CRYPTOPHYCIN-19

A further example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 3-chloro-4-methoxybenzyl, and $R_4$ and $R_8$ are taken together to form the didepsipeptide with the structure X where $R_9$ is hydrogen and $R_{10}$ is isobutyl. The structure of this cryptophycin compound, Cryptophycin 21, is the following:

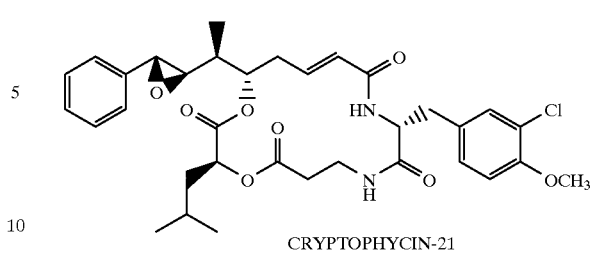

CRYPTOPHYCIN-21

A further example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 3,5-dichloro-4-hydroxybenzyl, and $R_4$ and $R_8$ are taken together to form the didepsipeptide with the structure X where $R_9$ is methyl and $R_{10}$ is isobutyl. The structure of this cryptophycin compound, Cryptophycin 23, is the following:

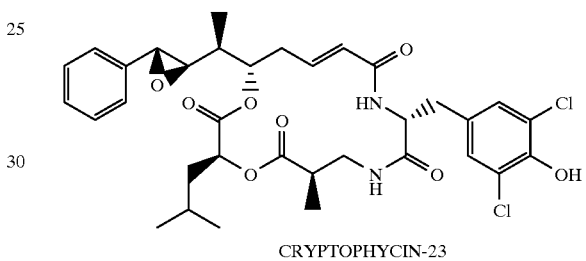

CRYPTOPHYCIN-23

A further example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 4-methoxybenzyl, and $R_4$ and $R_8$ are taken together to form the didepsipeptide with the structure X where $R_9$ is hydrogen and $R_{10}$ is isobutyl. The structure of this cryptophycin compound, Cryptophycin 24, is the following:

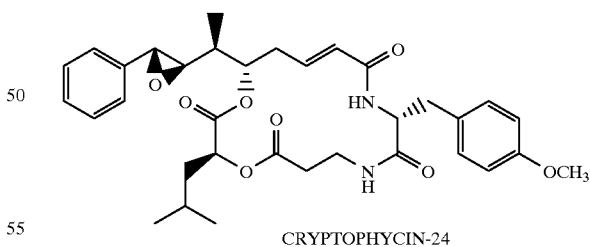

CRYPTOPHYCIN-24

A further example of a novel cryptophycin compound of the present invention is when $R_1$ and $R_2$ are taken together to form a second bond between $C_{10}$ and $C_{11}$ carbons such that there is a double bond, $R_3$ is methyl, $R_4$ is hydroxy, $R_6$ is hydrogen, $R_7$ is 3-chloro4-methoxybenzyl, and $R_5$ and $R_8$ are taken together to form the didepsipeptide with the structure X where $R_9$ is methyl and $R_{10}$ is isobutyl. The structure of this cryptophycin compound, Cryptophycin 26, is the following:

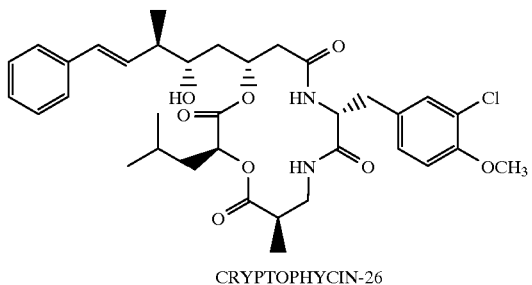

CRYPTOPHYCIN-26

A further example of a novel cryptophycin compound of the present invention is when $R_1$ and $R_2$ are taken together to form a second bond between the $C_{10}$ and $C_{11}$ carbons such that there is a double bond, $R_3$ is hydrogen, $R_5$ and $R_6$ are taken together to form a second bond between $C_5$ and $C_6$ such that there is a double bond, $R_7$ is 3-chloro-4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 28, is the following:

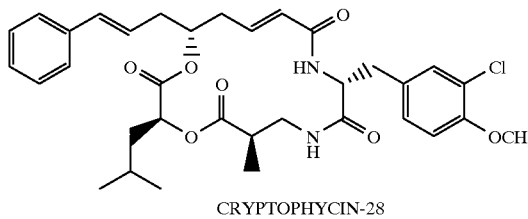

CRYPTOPHYCIN-28

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 3-chloro4-methoxybenzyl, and $R_4$ and $R_8$ are taken together to form the didepsipeptide with the structure X where $R_9$ is hydrogen and $R_{10}$ is isobutyl. The structure of this cryptophycin compound, Cryptophycin 29, is the following:

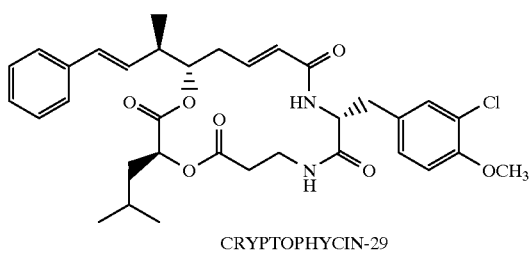

CRYPTOPHYCIN-29

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ is hydroxy, $R_6$ is hydrogen, $R_7$ is 3-chloro-4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 30, is the following:

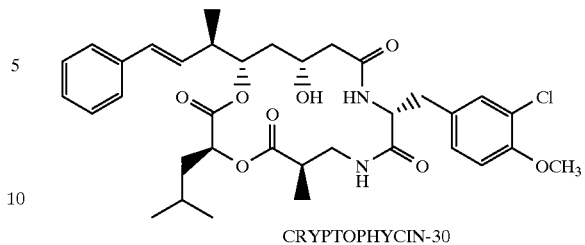

CRYPTOPHYCIN-30

A further example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 3,5-dichloro-4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 31, is the following:

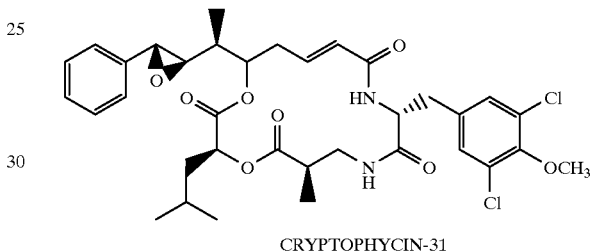

CRYPTOPHYCIN-31

A further example of a novel cryptophycin compound of the present invention is when $R_1$ and $R_2$ are taken together to form an epoxide group, $R_3$ is methyl, $R_5$ is hydrogen, $R_6$ is hydrogen, $R_7$ is 3-chloro4-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 35, is the following:

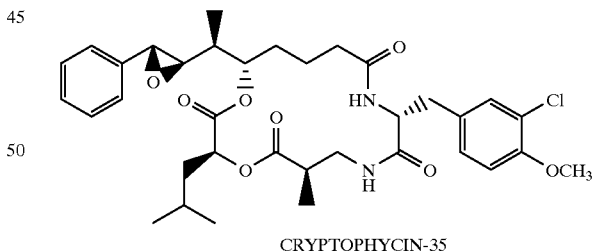

CRYPTOPHYCIN-35

A further example of a novel cryptophycin compound of the present invention is when $R_1$ and $R_2$ are taken together to form an epoxide group, $R_3$ is hydrogen, $R_5$ and $R_6$ are taken together to form a second bond between $C_5$ and $C_6$ such that there is a double bond, $R_7$ is 3-chloro-methoxybenzyl, and $R_4$ and $R_8$ are taken together to form the didepsipeptide with the structure X where $R_9$ is methyl and $R_{10}$ is isobutyl. The structure of this cryptophycin compound, Cryptophycin 40, is the following:

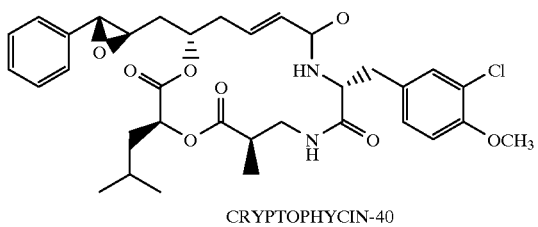

CRYPTOPHYCIN-40

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 3,5-dichloro-4-hydroxybenzyl, and $R_4$ and $R_8$ are taken together to form the didepsipeptide with the structure X where $R_9$ is methyl and $R_{10}$ is isobutyl. The structure of this cryptophycin compound, Cryptophycin 45, is the following:

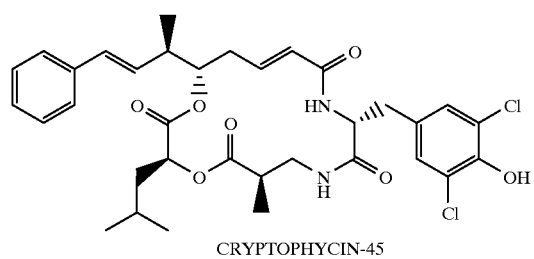

CRYPTOPHYCIN-45

A further example of a novel cryptophycin compound of the present invention is when $R_1$ and $R_2$ are taken together to form an epoxide, group, $R_3$ is methyl, $R_5$ and $R_6$ are taken together to form a second bond between $C_5$ and $C_6$ such that there is a double bond, $R_7$ is 3-chloro-4-methoxybenzyl, and $R_4$ and $R_8$ are taken together to form the didepsipeptide with the structure X where $R_9$ is methyl and $R_{10}$ is propyl. The structure of this cryptophycin compound, Cryptophycin 49, is the following:

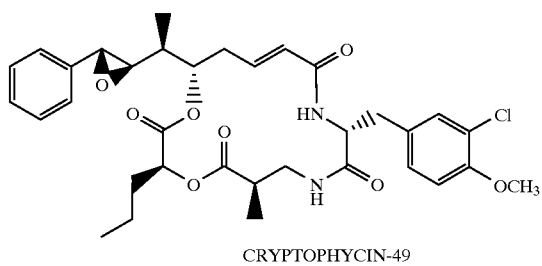

CRYPTOPHYCIN-49

A further example of a novel cryptophycin compound of the present invention is when $R_1$ and $R_2$ are taken together to form a second bond between the $C_{10}$ and $C_{11}$ carbons such that there is a double bond, $R_3$ is methyl, $R_5$ and $R_6$ are taken together to form a second bond between $C_5$ and $C_6$ such that there is a double bond, $R_7$ is 3-chloro4-methoxybenzyl, and $R_4$ and $R_8$ are taken together to form the didepsipeptide with the structure X where $R_9$ is methyl and $R_{10}$ is propyl. The structure of this cryptophycin compound, Cryptophycin 50, is the following:

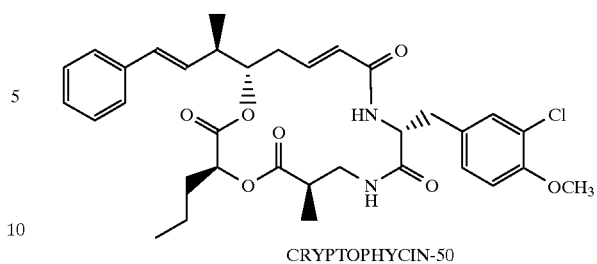

CRYPTOPHYCIN-50

A further example of a novel cryptophycin compound of the present invention is when $R_1$ and $R_2$ are taken together to form an epoxide group, $R_3$ is methyl, $R_5$ and $R_6$ are taken together to form a second bond between $C_5$ and $C_6$ such that there is a double bond, $R_7$ is 3-chloro-4-methoxybenzyl, and $R_4$ and $R_8$ are taken together to form the didepsipeptide with the structure X where $R_9$ is methyl and $R_{10}$ is sec-butyl. The structure of this cryptophycin compound, Cryptophycin 54, is the following:

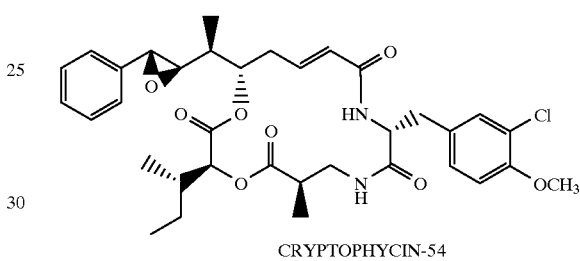

CRYPTOPHYCIN-54

The present invention further provides additional cryptophycins which have been produced via semi-synthetic pathways. These compounds can be represented by the following cryptophycin subgenus structure:

The present invention further provides a cryptophycin represented by the structure:

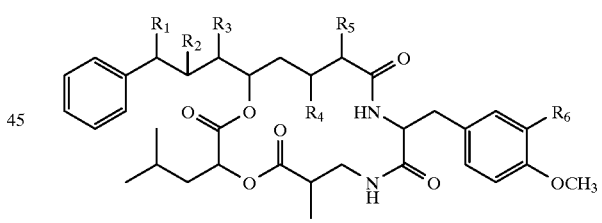

Wherein
$R_1$ is H or a halogen;
$R_2$ is H, an oxygen of a ketone or OH; or
$R_1$ and $R_2$ may be taken together to form an epoxide ring;
or $R_1$ and $R_2$ may be taken together to form an episulfide ring;
$R_3$ is H, or a lower alkyl group;
$R_4$ is H or OH;
$R_5$ is H or OH; or
$R_4$ and $R_5$ may be taken together to form a second bond;
$R_6$ is H or a halogen;
With the following proviso
when $R_1$ and $R_2$ are taken together to form an epoxide group, $R_4$ and $R_5$ are taken together to form a second bond and $R_6$ is chlorine, $R_3$ is not methyl.

The present invention further provides a method for producing a cryptophycin of the following structure:

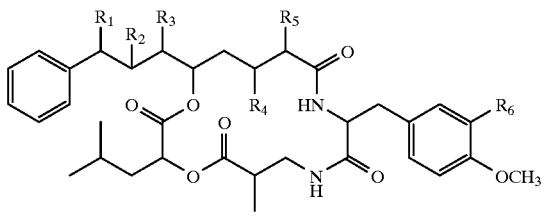

Wherein
R₁ is H or a halogen;
R₂ is H, an oxygen of a ketone or OH; or
R₁ and R₂ may be taken together to form an epoxide ring; or R₁ and R₂ may be taken together to form an episulfide ring;
R₃ is H, or a lower alkyl group;
R₄ is H or OH;
R₅ is H or OH; or
R₄ and R₅ may be taken together to form a second bond;
R₆ is H or a halogen;
With the following proviso
when R₁ and R₂ are taken together to form an epoxide group, R₄ and R₅ are taken together to form a second bond and R₆ is chlorine, R₃ is not methyl.

The present invention further provides a pharmaceutical composition useful for inhibiting the proliferation of a hyperproliferative mammalian cell comprising an effective amount of a compound with the following structure:

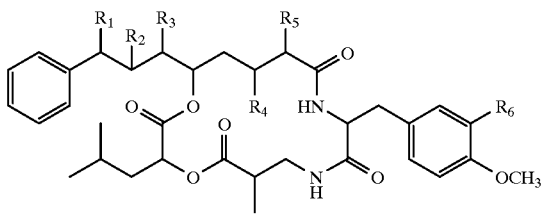

Wherein
R₁ is H or a halogen;
R₂ is H, an oxygen of a ketone or OH; or
R₁ and R₂ may be taken together to form an epoxide ring; or R₁ and R₂ may be taken together to form an episulfide ring;
R₃ is H, or a lower alkyl group;
R₄ is H or OH;
R₅ is H or OH; or
R₄ and R₅ may be taken together to form a second bond;
R₆ is H or a halogen;
With the following proviso
when R₁ and R₂ are taken together to form an epoxide group, R₄ and R₅ are taken together to form a second bond and R₆ is chlorine, R₃ is not methyl;
together with a pharmaceutically acceptable carrier.

In a preferred embodiment of the present invention, the pharmaceutical composition further comprises at least one additional anti-neoplastic agent. The present invention further provides a method for inhibiting the proliferation of a mammalian cell comprising contacting the mammalian cell with the cryptophycin compound set forth above in an amount sufficient to disrupt the dynamic state of microtubule polymerization and depolymerization to arrest cell mitosis, thereby inhibiting the proliferation of the cell. In a preferred embodiment, the method further comprises contacting the cell with at least one additional anti-neoplastic agent. In an additional preferred embodiment, the mammalian cell is hyperproliferative. In a preferred embodiment of the present invention, the hyperproliferative cell is human.

The present invention provides a method of alleviating a pathological condition caused by hyperproliferating mammalian cells comprising administering to a subject an effective amount of the pharmaceutical composition set forth above to inhibit proliferation of the cells. In a preferred embodiment, the mammalian cells are human. In an additional preferred embodiment, the method comprises administering to the subject at least one additional therapy directed to alleviating the pathological condition. In a preferred embodiment, the pathological condition is characterized by the formation of neoplasms. The neoplasms are selected from the group consisting of mammory, small-cell lung, non-small-cell lung, colorectal, leukemia, melanoma, pancreatic adenocarcinoma, central nervous system (CNS), ovarian, prostate, sarcoma of soft tissue or bone, head and neck, gastric which includes pancreatic and esophageal, stomach, myeloma, bladder, renal, neuroendocrine which includes thyroid and non-Hodgkin's disease and Hodgkin's disease neoplasms.

Set forth hereinbelow are additional cryptophycins, their substituent groups based upon the following structure:

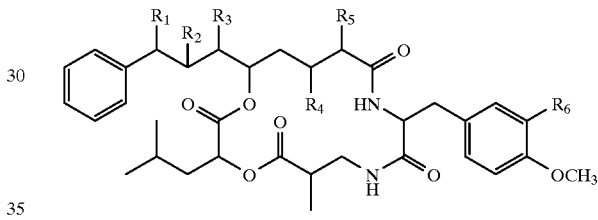

Wherein

R₁ is H or a halogen;

R₂ is H, an oxygen of a ketone or OH; or

R₁ and R₂ may be taken together to form an epoxide ring; or R₁ and R₂ may be taken together to form an episulfide ring;

R₃ is H, or a lower alkyl group;

R₄ is H or OH;

R₅ is H or OH; or

R₄ and R₅ may be taken together to form a second bond;

R₆ is H or a halogen;

With the following proviso when R₁ and R₂ are taken together to form an epoxide group, R₄ and R₅ are taken together to form a second bond and R₆ is chlorine, R₃ is not methyl.

An example of a novel cryptophycin compound of the present invention is when R₁ is hydrogen, R₂ is an oxygen of a ketone group, R₃ is S-methyl, R₄ and R₅ are taken together to form a second bond and R₆ is chloro. The structure of this cryptophycin compound, Cryptophycin 20 is the following:

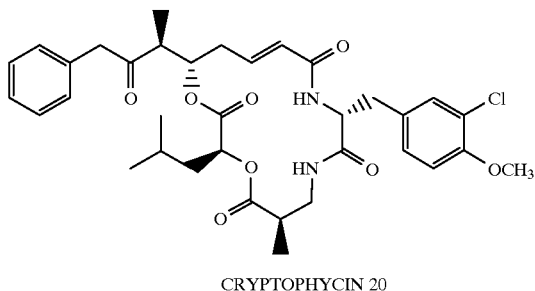

CRYPTOPHYCIN 20

A further example of a novel cryptophycin compound of the present invention is when $R_1$ is S-bromo, $R_2$ is R-hydroxy, $R_3$ is S-methyl, $R_4$ and $R_5$ are taken together to form a second bond and $R_6$ is chloro. The structure of this cryptophycin compound, Cryptophycin 25 is the following:

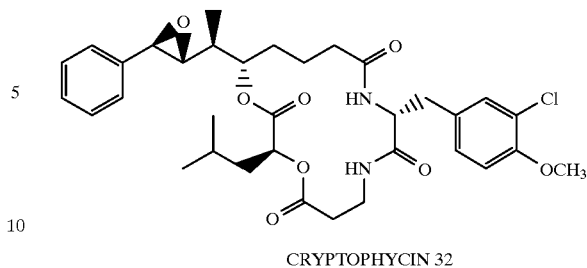

CRYPTOPHYCIN 32

A further example of a novel cryptophycin compound of the present invention is when $R_1$, $R_4$ and $R_5$ are hydrogen, $R_2$ is S-hydroxy, $R_3$ is R-methyl and $R_6$ is chloro. The structure of this cryptophycin compound, Cryptophycin 33 is the following:

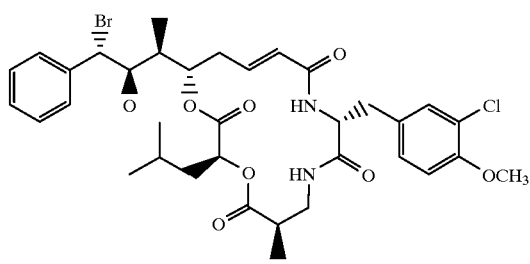

CRYPTOPHYCIN 25

A further example of a novel cryptophycin compound of the present invention is when $R_1$ is R-chloro, $R_2$ is R-hydroxy, $R_3$ is S-methyl, $R_4$ and $R_5$ are taken together to form a second bond and $R_6$ is chloro. The structure of this cryptophycin compound, Cryptophycin 27 is the following:

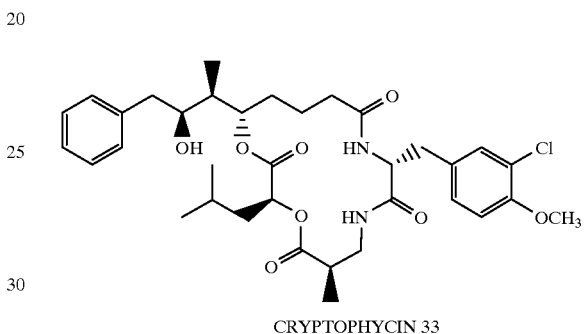

CRYPTOPHYCIN 33

A further example of a novel cryptophycin compound of the present invention is when $R_1$, $R_2$, $R_4$ and $R_5$ are hydrogen, $R_3$ is R-methyl and $R_6$ is hydrogen. The structure of this cryptophycin compound, Cryptophycin 34 is the following:

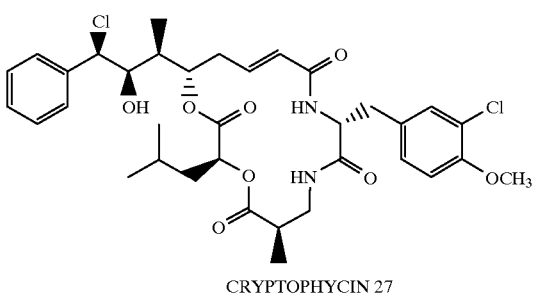

CRYPTOPHYCIN 27

A further example of a novel cryptophycin compound of the present invention is when $R_1$ and $R_2$ are taken together to form a R,R-epoxide ring, $R_3$ is S-methyl, $R_4$ and $R_5$ are hydrogen and $R_6$ is chloro. The structure of this cryptophycin compound, Cryptophycin 32 is the following:

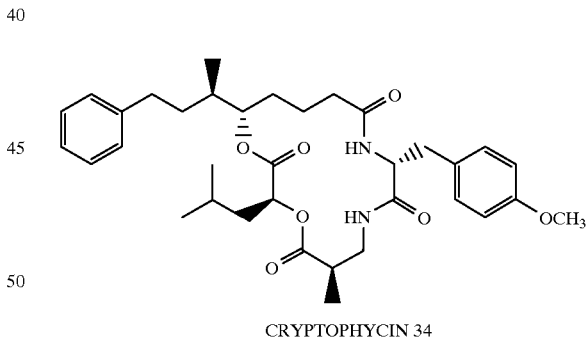

CRYPTOPHYCIN 34

A further example of a novel cryptophycin compound of the present invention is when $R_1$ is R-bromo, $R_2$ is R-hydroxy, $R_3$ is S-methyl, $R_4$ and $R_5$ are taken together to form a second bond and $R_6$ is chloro. The structure of this cryptophycin compound, Cryptophycin 37 is the following:

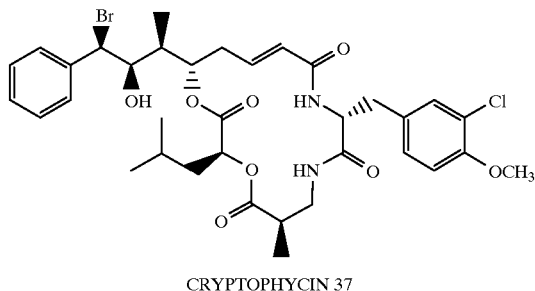

CRYPTOPHYCIN 37

A further example of a novel cryptophycin compound of the present invention is when $R_1$ and $R_2$ are taken together to form a S,S-epoxide ring, $R_3$ is S-methyl, $R_4$ and $R_5$ are taken together to form a second bond and $R_6$ is chloro. The structure of this cryptophycin compound, Cryptophycin 38, is the following:

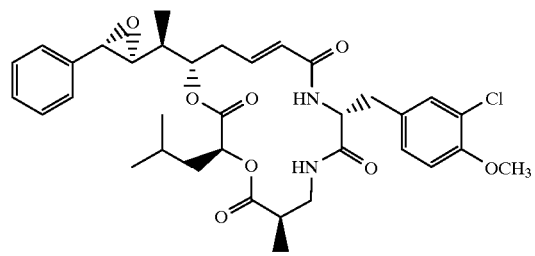

CRYPTOPHYCIN 38

A further example of a novel cryptophycin compound of the present invention is when $R_1$ and $R_2$ are taken together to form a S,R-epoxide ring, $R_3$ is S-methyl, $R_4$ and $R_5$ are taken together to form a second bond and $R_6$ is chloro. The structure of this cryptophycin compound, Cryptophycin 39, is the following:

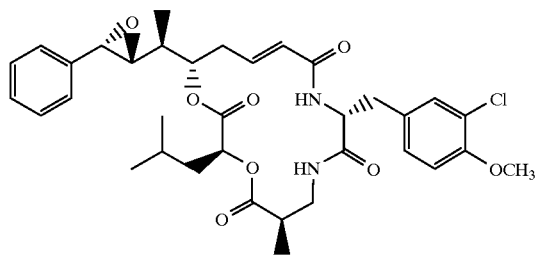

CRYPTOPHYCIN 39

A further example of a novel cryptophycin compound of the present invention is when $R_1$ and $R_2$ are taken together to form a R,R-epoxide ring, $R_3$ is S-methyl, $R_4$ is S-hydroxy, $R_5$ is R-hydroxy and $R_6$ is chloro. The structure of this cryptophycin compound, Cryptophycin 41, is the following:

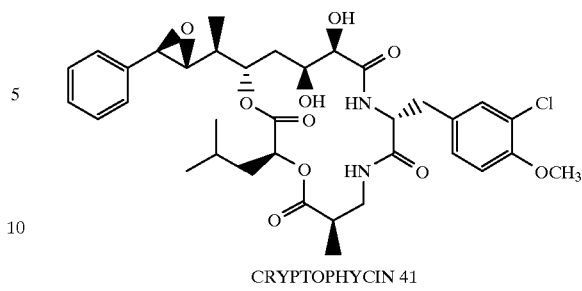

CRYPTOPHYCIN 41

A further example of a novel cryptophycin compound of the present invention is when $R_1$ and $R_2$ are taken together to form a R,R-epoxide ring, $R_3$ is S-methyl, $R_4$ is R-hydroxy, $R_5$ is S-hydroxy and $R_6$ is chloro. The structure of this cryptophycin compound, Cryptophycin 42, is the following:

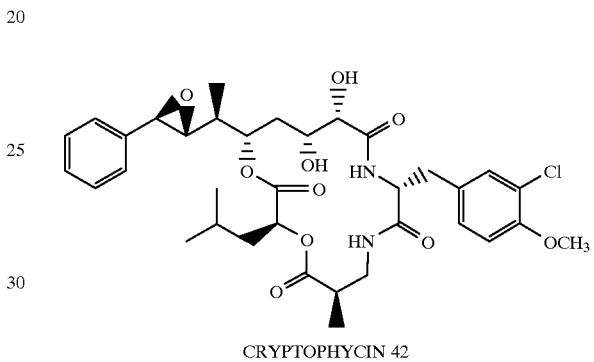

CRYPTOPHYCIN 42

A further example of a novel cryptophycin compound of the present invention is when $R_1$ is hydrogen, $R_2$ is S-hydroxy, $R_3$ is R-methyl, $R_4$ and $R_5$ are taken together to form a second bond and $R_6$ is chloro. The structure of this cryptophycin compound, Cryptophycin 48, is the following:

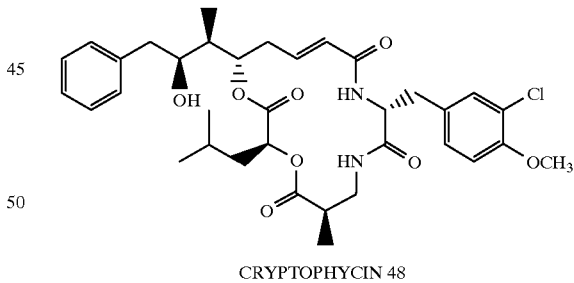

CRYPTOPHYCIN 48

A further example of a novel cryptophycin compound of the present invention is when $R_1$ is S-chloro, $R_2$ is R-hydroxy, $R_3$ is S-methyl, $R_4$ and $R_5$ are hydrogen and $R_6$ is chloro. The structure of this cryptophycin compound, Cryptophycin 59, is the following:

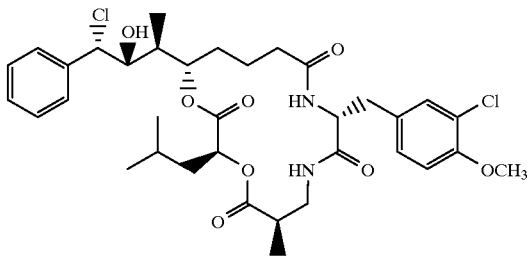

CRYPTOPHYCIN 59

A further example of a novel cryptophycin compound of the present invention is when $R_1$ and $R_2$ are taken together to form a S,S-episulfide ring, $R_3$ is S-methyl, $R_4$ and $R_5$ are taken together to form a second bond and $R_6$ is chloro. The structure of this cryptophycin compound, Cryptophycin 60, is the following:

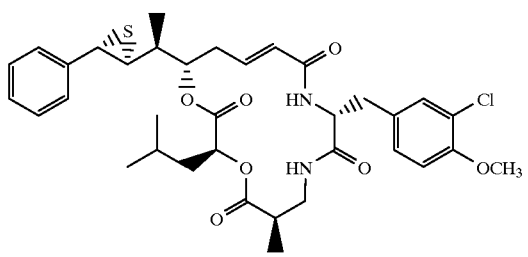

CRYPTOPHYCIN 60

A further example of a novel cryptophycin compound of the present invention is when $R_1$ is S-chloro, $R_2$ is R-hydroxy, $R_3$ is hydrogen, $R_4$ and $R_5$ are taken together to form a second bond and $R_6$ is chloro. The structure of this cryptophycin compound, Cryptophycin 63, is the following:

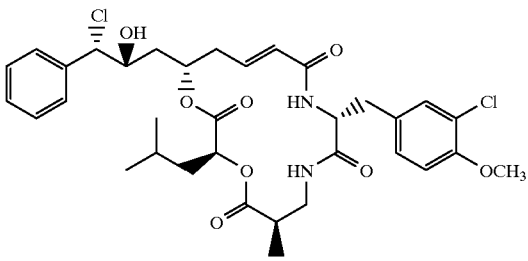

CRYPTOPHYCIN 63

A further example of a novel cryptophycin compound of the present invention is when $R_1$ is R-chloro, $R_2$ is R-hydroxy, $R_3$ is S-methyl, $R_4$ and $R_5$ are hydrogen and $R_6$ is chloro. The structure of this cryptophycin compound, Cryptophycin 64, is the following:

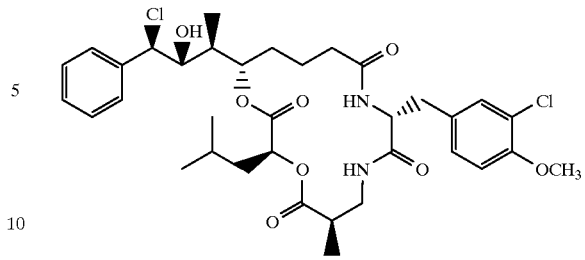

CRYPTOPHYCIN 64

A further example of a novel cryptophycin compound of the present invention is when $R_1$ is R-chloro, $R_2$ is S-hydroxy, $R_3$ is S-methyl, $R_4$ and $R_5$ are taken together to form a second bond and $R_6$ is chloro. The structure of this cryptophycin compound, Cryptophycin 69, is the following:

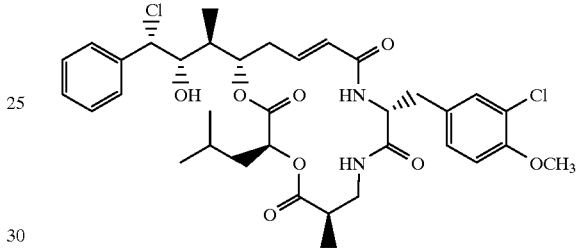

CRYPTOPHYCIN 69

A further example of a novel cryptophycin compound of the present invention is when $R_1$ is S-chloro, $R_2$ is S-hydroxy, $R_3$ is S-methyl, $R_4$ and $R_5$ are taken together to form a second bond and $R_6$ is chloro. The structure of this cryptophycin compound, Cryptophycin 70, is the following:

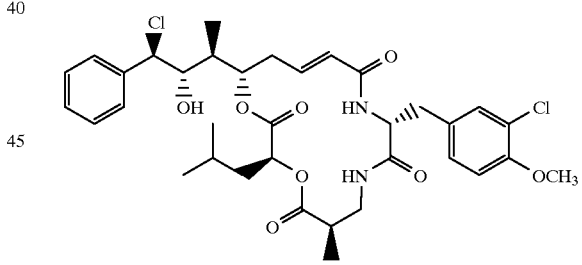

CRYPTOPHYCIN 70

A further example of a novel cryptophycin compound of the present invention is when $R_1$ is R-bromo, $R_2$ is S-hydroxy, $R_3$ is S-methyl, $R_4$ and $R_5$ are taken together to form a second bond and $R_4$ is chloro. The structure of this cryptophycin compound, Cryptophycin 71, is the following:

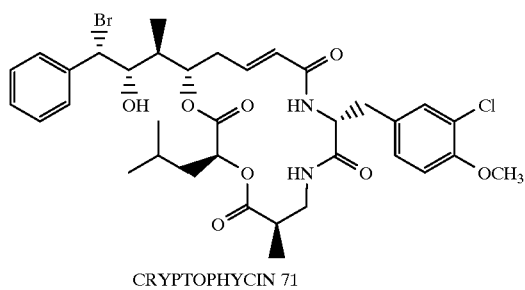

CRYPTOPHYCIN 71

A further example of a novel cryptophycin compound of the present invention is when $R_1$ is S-bromo, $R_2$ is S-hydroxy, $R_3$ is S-methyl, $R_4$ and $R_5$ are taken together to form a second bond and $R_6$ is chloro. The structure of this cryptophycin compound, Cryptophycin 72, is the following:

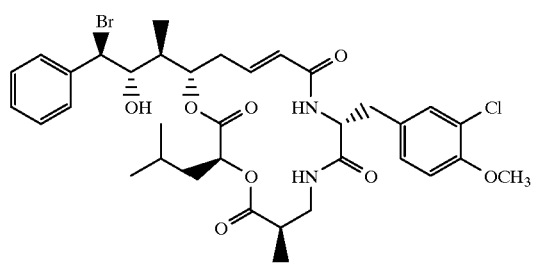

CRYPTOPHYCIN 72

A further example of a novel cryptophycin compound of the present invention is when $R_1$ is S-chloro, $R_2$ is S-hydroxy, $R_3$ is S-methyl, $R_4$ and $R_5$ are taken together to form a second bond and $R_6$ is chloro. The structure of this cryptophycin compound, Cryptophycin 73, is the following:

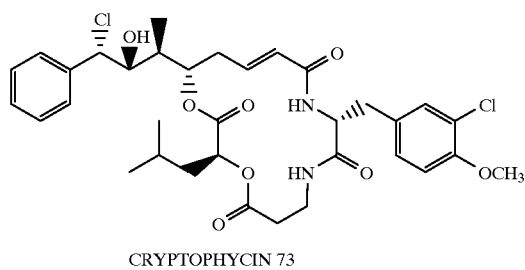

CRYPTOPHYCIN 73

A further example of a novel cryptophycin compound of the present invention is when $R_1$ is S-chloro, $R_2$ is R-hydroxy, $R_3$ is S-methyl, $R_4$ and $R_5$ are taken together to form a second bond and $R_6$ is hydrogen. The structure of this cryptophycin compound, Cryptophycin 74, is the following:

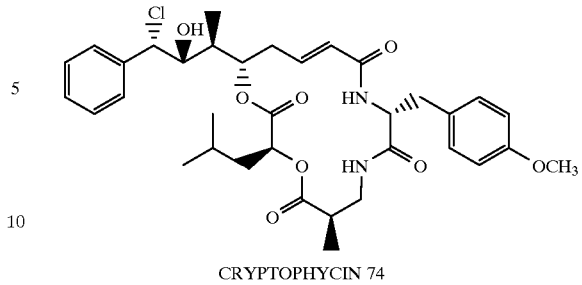

CRYPTOPHYCIN 74

A further example of a novel cryptophycin compound of the present invention is when $R_1$ is S-fluoro, $R_2$ is R-hydroxy, $R_3$ is S-methyl, $R_4$ and $R_5$ are taken together to form a second bond and $R_6$ is chloro. The structure of this cryptophycin compound, Cryptophycin 75, is the following:

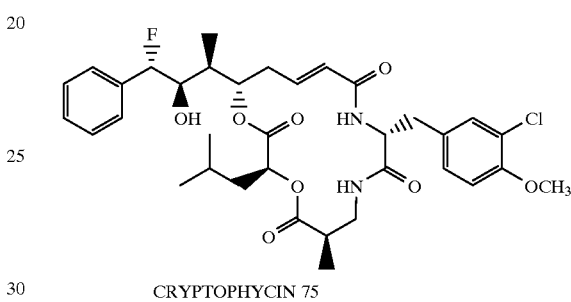

CRYPTOPHYCIN 75

A further example of a novel cryptophycin compound of the present invention is when $R_1$ is R-fluoro, $R_2$ is R-hydroxy, $R_3$ is S-methyl, $R_4$ and $R_5$ are taken together to form a second bond and $R_6$ is chloro. The structure of this cryptophycin compound, Cryptophycin 76, is the following:

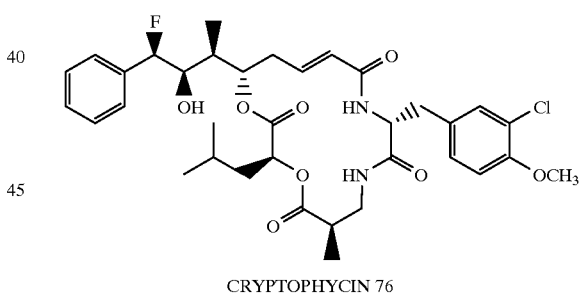

CRYPTOPHYCIN 76

Of the above compounds, Cryptophycins 2, 4, 16–19, 21, 23, 24, 26, 28–31, 40, 43, 45, 49, 50, and 54 are metabolites produced by a strain of Nostoc sp. of blue-green algae (cyanobacteria) which has been cultured, with these compounds subsequently isolated from this culture. Cryptophycins 6 and 7 are artifacts that are produced if the isolation procedure utilizes solvents containing methanol. Cryptophycins 8, 9, 10–12, 14, 20, 25, 27, 32–35, 37, 38, 41, 42, 48, 59, 60, 63, 64 and 69–76 are derivatives of these naturally-produced metabolites, having been chemically modified with the methods described in the Experimental Section of this application, with alternate methods to create the exemplified compounds, as well as the non-exemplified compounds, available to those of ordinary skill in the art.

The present invention provides methods of producing the above cryptophycin compounds through the culturing of a strain of the Nostoc sp. The morphological characteristics of the Nostoc sp. of blue-green algae (cyanobacteria), as provided in U.S. Pat. No. 4,946,835, are that they are filamentous and consist of vegetative cells. In longer filaments, heterocysts occasionally are observed in an intercalary position. Akinetes are not observed. Reproduction is by hormogonia in addition to random trichome breakage. The basis for an identification of a Nostoc sp. can be found in J. Gen. Micro., 111:1–61 (1979).

The invention further provides that a Nostoc sp. may be cultured and that novel cryptophycin metabolites, as well as previously disclosed cryptophycin metabolites, may be isolated from this culture. In a preferred embodiment of the present invention, the Nostoc sp. strain designated GSV 224 is the strain which is cultivated and from which are isolated compounds represented by the following structure:

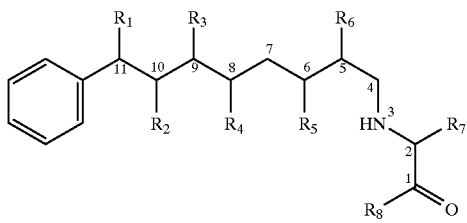

Wherein
$R_1$ is H, OH, a halogen, O of a ketone group, $NH_2$, SH, a lower alkoxyl group or a lower alkyl group;
$R_2$ is H, OH, O of a ketone group, $NH_2$, SH, a lower alkoxyl group or a lower alkyl group; or
$R_1$ and $R_2$ may be taken together to form an epoxide ring, an aziridene ring, a sulfide ring or a second bond between $C_{10}$ and $C_{11}$; or
$R_1$ and $R_4$ may be taken together to form a tetrahydrofuran ring;
$R_3$ is H or a lower alkyl group;
$R_4$ is OH, a lower alkanoyloxy group or a lower α-hydroxy alkanoyloxy group;
$R_5$ is H or an OH group;
$R_6$ is H; or
$R_5$ and $R_6$ may be taken together to form a second bond between $C_5$ and $C_6$;
$R_7$ is a benzyl, hydroxybenzyl, methoxybenzyl, halohydroxybenzyl, dihalohydroxybenzyl, halomethoxybenzyl, or dihalomethoxybenzyl group;
$R_8$ is OH, a lower β-amino acid wherein $C_1$ is bonded to N of the β-amino acid, or an esterified lower β-amino acid wherein $C_1$ is bonded to N of the esterified lower β-amino acid group;
$R_4$ and $R_8$ may be taken together to form a didepsipeptide group consisting of a lower β-amino acid bonded to a lower α-hydroxy alkanoic acid; or
$R_5$ and $R_8$ may be taken together to form a didepsipeptide group consisting of a lower β-amino acid bonded to a lower α-hydroxy alkanoic acid;
with the following provisos:
$R_1$ is H, a lower alkyl group, or a lower alkoxyl group only if $R_2$ is OH, O of a ketone group, $NH_2$, SH.

In a preferred embodiment of the invention, chemically modifying a cryptophycin metabolite isolated by the above method provides a distinct compound also having this structure. Procedures for chemically modifying cryptophycin compounds to produce additional compounds within the scope of the present invention are available to those of ordinary skill in the art. Moreover, additional procedures are described in greater detail in the Experimental Section of this application.

In addition to the novel cryptophycin compounds of the present invention, the present invention provides novel methods of producing, as well as using, the above structure which includes the following previously disclosed cryptophycin species, Cryptophycins 1, 3, 5, 13 and 15. The structures of these compounds are the following:

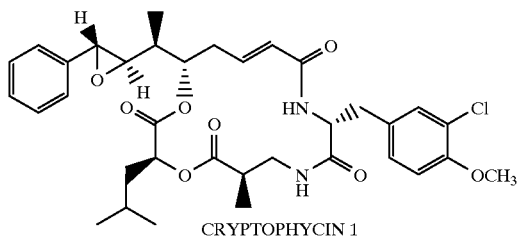

CRYPTOPHYCIN 1

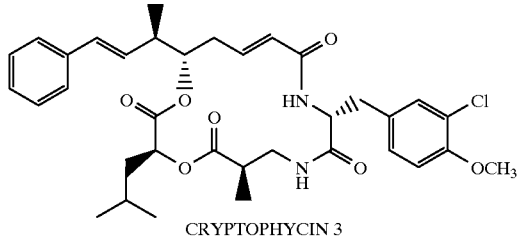

CRYPTOPHYCIN 3

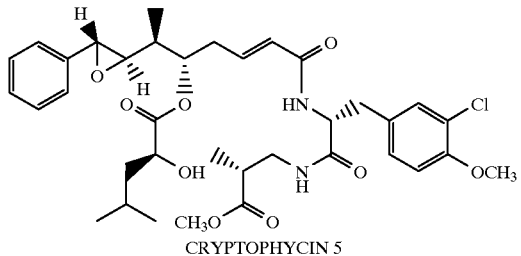

CRYPTOPHYCIN 5

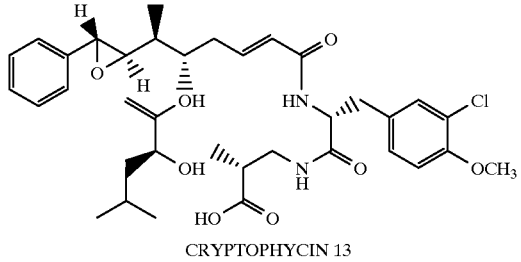

CRYPTOPHYCIN 13

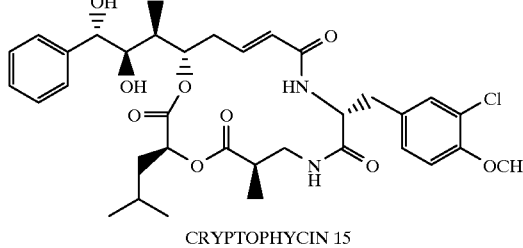

CRYPTOPHYCIN 15

The invention provided herewith is directed to any strain of the Nostoc sp. and preferably to the Nostoc sp. GSV 224 strain to produce cryptophycin compounds. To that end, the GSV 224 strain of Nostoc sp. was deposited on Oct. 7, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 55483. Other strains of Nostoc sp., in particular strain MB 5357 previously deposited by Merck and Co. under ATCC accession No. 53789, are strains contemplated to be utilized to practice the present invention.

As is the case with other organisms, the characteristics of Nostoc sp. are subject to variation. For example, recombinants, variants, or mutants of the specified strains may be obtained by treatment with various known physical and chemical mutagens, such as ultraviolet ray, X-rays, gamma rays, and N-methyl-N'-nitro-N-nitrosoguanidine. All natural and induced variants, mutants, and recombinants of the specified strains which retain the characteristic of producing a cryptophycin compound are intended to be within the scope of the claimed invention.

The cryptophycin compounds of the present invention can be prepared by culturing a strain of Nostoc sp. under submerged aerobic conditions in a suitable culture medium until substantial antibiotic activity is produced. Other culture techniques, such as surface growth on solidified media, can also be used to produce these compounds. The culture medium used to grow the specified strains can include any of one of many nitrogen and carbon sources and inorganic salts that are known to those of ordinary skill in the art. Economy in production, optimal yields, and ease of product isolation are factors to consider when choosing the carbon sources and nitrogen sources to be used. Among the nutrient inorganic salts which can be incorporated in the culture media are the customary soluble salts capable of yielding iron, potassium, sodium, magnesium, calcium, ammonium, chloride, carbonate, phosphate, sulfate, nitrate, and like ions.

Essential trace elements which are necessary for the growth and development of the organisms should also be included in the culture medium. Such trace elements commonly occur as impurities in other constituents of the medium in amounts sufficient to meet the growth requirements of the organisms. It may be desirable to add small amounts (i.e. 0.2 mL/L) of an antifoam agent such as polypropylene glycol (M.W. about 2000) to large scale cultivation media if foaming becomes a problem.

For production of substantial quantities of the cryptophycin compounds, submerged aerobic cultivation in tanks can be used. Small quantities may be obtained by shake-flask culture. Because of the time lag in metabolite production commonly associated with inoculation of large tanks with the organisms, it is preferable to use a vegetative inoculum. The vegetative inoculum is prepared by inoculating a small volume of culture medium with fragments of the vegetative trichome or heterocyst-containing form of the organism to obtain a fresh, actively growing culture of the organism. The vegetative inoculum is then transferred to a larger tank. The medium used for the vegetative inoculum can be the same as that used for larger cultivations or fermentation, but other media can also be used.

The organisms may be grown at temperatures between about 20° C. and 30° C. and an incident illumination intensity of about 100 to 200 $\mu$mol photons $m^{-2}Sec^{-1}$ (photosynthetically active radiation).

As is customary in aerobic submerged culture processes of this type, carbon dioxide gas is introduced into the culture by addition to the sterile air stream bubbled through the culture medium. For efficient production of the cryptophycin compounds, the proportion of carbon dioxide should be about 1% (at 24° C. and one atmosphere of pressure).

The prior art, specifically U.S. Pat. No. 4,946,835, provides methods of cultivating Nostoc sp., the contents of which are hereby incorporated by reference.

Cryptophycin compound production can be followed during the cultivation by testing samples of the broth against organisms known to be sensitive to these antibiotics. One useful assay organism is *Candida albicans*.

Following their production under submerged aerobic culture conditions, cryptophycin compounds of the invention can be recovered from the culture and from the culture media by methods known to those of ordinary skill in this art. Recovery is generally accomplished by initially filtering the culture medium to separate the algal cells and then freeze-drying the separated cells. The freeze-dried alga can be extracted with a suitable solvent such as ethanol, methanol, isopropanol, or dichloromethane. The cryptophycins can be separated by subjecting this extract, as well as the culture media, to rapid chromatography on reversed-phase column. The cryptophycins can be purified by reversed-phase high-performance liquid chromatography (HPLC).

As will be apparent from their structures, the cryptophycin compounds have groups which are capable of chemical modification. The genus compound of the present invention contemplates those cryptophycins which exhibit anti-neoplastic activity. For example, the derivatives exemplified in the present invention include compounds having the epoxide oxygen or hydroxy groups on C-7 and C-8 of unit A or the leucic acid group of unit B of FIG. 1. Such derivatives of the novel and previously disclosed compounds which display the desired anti-neoplastic activity are included in the claimed invention. Moreover, the relationship between the structure of the cryptophycin compounds and anti-neoplastic activity is provided in the Experimental Section hereinbelow.

While selected cryptophycin compounds are known to be metabolites produced by the alga of the present invention, other cryptophycin compounds, e.g. Cryptophycins 8–15, can be derived from the metabolites using published techniques which are known to those of ordinary skill in the art; for example, the syntheses disclosed in U.S. Pat. Nos. 4,868,208, 4,845,086, and 4,845,085, the contents of which are hereby incorporated by reference, or by utilizing other methods which are known to those of ordinary skill in the art. Moreover, the present invention provides methods of producing derivatives in the Experimental Section.

The novel cryptophycin compounds of the present invention and the previously disclosed cryptophycin compounds can be therapeutically employed as anti-neoplastic agents and thereby used in methods to treat neoplastic diseases. As used herein, "neoplastic" pertains to a neoplasm, which is an abnormal growth, such growth occurring because of a proliferation of cells not subject to the usual limitations of growth. As used herein, "anti-neoplastic agent" is any compound, composition, admixture, co-mixture or blend which inhibits, eliminates, retards or reverses the neoplastic phenotype of a cell.

Chemotherapy, surgery, radiation therapy, therapy with biologic response modifiers, and immunotherapy are currently used in the treatment of cancer. Each mode of therapy has specific indications which are known to those of ordinary skill in the art, and one or all may be employed in an attempt to achieve total destruction of neoplastic cells. Chemotherapy utilizing one or more cryptophycins is provided by the present invention. Moreover, combination chemotherapy, chemotherapy utilizing cryptophycins in combination with other neoplastic agents, is also provided by the subject invention as combination therapy is generally more effective than the use of single anti-neoplastic agents. Thus, a further aspect of the present invention provides compositions containing a therapeutically effective amount of at least one new cryptophycin compound of the present invention, including nontoxic addition salts thereof, which serve to provide the above-recited therapeutic benefits. Such compositions can also be provided together with physiologically tolerable liquid, gel or solid carriers, diluents, adjuvants and excipients. Such carriers, diluents, adjuvants and excipients may be found in the *United States Pharmacopeia Vol. XXII and National Formulary Vol XVII,* U.S. Pharmacopeia Convention, Inc., Rockville, Md. (1989), the contents of which are herein incorporated by reference. Additional modes of treatment are provided in *AHFS Drug Information,* 1993 ed. by the American Hospital Formulary Service, pp. 522–660, the contents of which are herein incorporated by reference.

The present invention further provides that the pharmaceutical composition used to treat neoplastic disease contains at least one cryptophycin compound and at least one additional anti-neoplastic agent. Anti-neoplastic compounds which may be utilized in combination with cryptophycin include those provided in *The Merck Index,* 11th ed. Merck & Co., Inc. (1989) pp. Ther 16–17, the contents of which are hereby incorporated by reference. In a further embodiment of the invention, anti-neoplastic agents may be antimetabolites which may include, but are not limited to, methotrexate, 5-fluorouracil, 6-mercaptopurine, cytosine arabinoside, hydroxyurea, and 2-chlorodeoxyadenosine. In another embodiment of the present invention, the anti-neoplastic agents contemplated are alkylating agents which may include, but are not limited to, cyclophosphamide, melphalan, busulfan, paraplatin, chlorambucil, and nitrogen mustard. In a further embodiment of the subject invention, the anti-neoplastic agents are plant alkaloids which may include, but are not limited to, vincristine, vinblastine, taxol, and etoposide. In a further embodiment of the present invention, the anti-neoplastic agents contemplated are antibiotics which may include, but are not limited to, doxorubicin (adriamycin), daunorubicin, mitomycin c, and bleomycin. In a further embodiment of the subject invention, the anti-neoplastic agents contemplated are hormones which may include, but are not limited to, calusterone, diomostavolone, propionate, epitiostanol, mepitiostane, testolactone, tamoxifen, polyestradiol phosphate, megesterol acetate, flutamide, nilutamide, and trilotane. In a further embodiment of the subject invention, the anti-neoplastic agents contemplated include enzymes which may include, but are not limited to, L-Asparaginase or aminoacridine derivatives which may include, but are not limited to, amsacrine. Additional anti-neoplastic agents include those provided in Skeel, Roland T., "Antineoplastic Drugs and Biologic Response Modifier: Classification, Use and Toxicity of Clinically Useful Agents," *Handbook of Cancer Chemotherapy* (3rd ed.), Little Brown & Co. (1991), the contents of which are herein incorporated by reference.

These compounds and compositions can be administered to mammals for veterinary use, such as for domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 mg/kg, more usually 0.01 to 10 mg/kg, of the host body weight. Alternatively, dosages within these ranges can be administered by constant infusion over an extended period of time, usually exceeding 24 hours, until the desired therapeutic benefits have been obtained. Indeed, drug dosage, as well as route of administration, must be selected on the basis of relative effectiveness, relative toxicity, growth characteristics of tumor and effect of cryptophycins on cell cycle, drug pharmacokinetics, age, sex, physical condition of the patient, and prior treatment.

The cryptophycin compounds, with or without additional anti-neoplastic agents, may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Such salts may also be formed as acid addition salts with any free cationic groups and will generally be formed with inorganic acids such as, for example, hydrochloric or phosphoric acids, or organic acids such as acetic, oxalic, tartaric, mandelic, and the like. Additional excipients which the further invention provides are those available to one of ordinary skill in the art, for example, that found in the *United States Pharmacopeia Vol. XXI and National Formulary Vol XVII,* U.S. Pharmacopeia Convention, Inc., Rockville, Md. (1989), which is herein incorporated by reference.

The suitability of particular carriers for inclusion in a given therapeutic composition depends on the preferred route of administration. For example, anti-neoplastic compositions may be formulated for oral administration. Such compositions are typically prepared either as liquid solution or suspensions, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

Compositions of the present invention may also be prepared as injectable, either as liquid solutions, suspensions, or emulsions; solid forms suitable for solution in, or suspension in, liquid prior to injection may be prepared. Such injectables may be administered subcutaneously, intravenously, intraperitoneally, intramuscularly, intrathecally, or intrapleurally. The active ingredient or ingredients are often mixed with diluents or excipients which are physiologically tolerable and compatible with the active ingredient(s). Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

The invention further provides methods for using cryptophycin compounds encompassed by the genus structure to inhibit the proliferation of mammalian cells by contacting these cells with a cryptophycin compound in an amount sufficient to inhibit the proliferation of the mammalian cell. A preferred embodiment is a method to inhibit the proliferation of hyperproliferative mammalian cells. For purposes of this invention, "hyperproliferative mammalian cells" are mammalian cells which are not subject to the characteristic limitations of growth, e.g., programmed cell death (apoptosis). A further preferred embodiment is when the mammalian cell is human. The invention further provides contacting the mammalian cell with at least one cryptophycin compound and at least one additional anti-neoplastic agent. The types of anti-neoplastic agents contemplated are the same as those disclosed hereinabove.

The invention further provides methods for using cryptophycin compounds encompassed by the genus structure to inhibit the proliferation of hyperproliferative cells with drug-resistant phenotypes, including those with multiple drug-resistant phenotypes, by contacting said cell with a cryptophycin compound in an amount sufficient to inhibit the proliferation of a hyperproliferative mammalian cell. A preferred embodiment is when the mammalian cell is human. The invention further provides contacting the mammalian cell with a cryptophycin compound and at least one additional anti-neoplastic agent. The types of anti-neoplastic agents contemplated are the same as those disclosed hereinabove.

The invention further provides a method for alleviating pathological conditions caused by hyperproliferating mammalian cells, for example, neoplasia, by administering to a subject an effective amount of a pharmaceutical composition provided hereinabove to inhibit the proliferation of the hyperproliferating cells. As used herein "pathological condition" refers to any pathology arising from the proliferation of mammalian cells that are not subject to the normal limitations of cell growth. Such proliferation of cells may be due to neoplasms, including, but not limited to the following neoplasms: mammary, small-cell lung, non-small-cell lung, colorectal, leukemia, melanoma, central nervous system (CNS), ovarian, prostate, sarcoma of soft tissue or bone, head and neck, gastric which includes pancreatic and esophageal, stomach, myeloma, bladder, renal, neuroendocrine which includes thyroid and lymphoma, non-Hodgkin's and Hodgkin's. In a further embodiment of the invention, the neoplastic cells are human. The present invention further provides methods of alleviating such pathological conditions utilizing cryptophycin in combination with other therapies, as well as other anti-neoplastic agents. Such therapies and their appropriateness for different neoplasia may be found in *Cancer Principles and Practice of Oncology,* 4th ed., Editors DeVita, V., Hellman, S., and Rosenberg., S., Lippincott Co. (1993), the contents of which are herein incorporated by reference.

In the present disclosure, cryptophycin compounds are shown to potently disrupt the microtubule structure in cultured cells. In addition, and in contrast with the Vinca alkaloids, cryptophycin compounds appear to be a poor substrate for the drug-efflux pump P-glycoprotein. Cryptophycin 1 is the major cytotoxin in the blue-green alga (cyanobacteria) Nostoc sp. strain designated GSV 224 and shows excellent activity against tumors implanted in mice. This cyclic didepsipeptide had previously been isolated from Nostoc sp. ATCC accession no. 53787 as an antifungal agent and its gross structure was previously determined. The relative and absolute stereochemistry of this potentially important drug has now been established using a combination of chemical and spectral techniques. Twenty-four additional cryptophycin compounds, Cryptophycins 2–7, 16–19, 21, 23, 24, 26, 28–31, 40, 43, 45, 49, 50 and 54 have also been isolated from GSV 224 and their total structures and cytotoxicities determined. Several derivatives and degradation products are described, both chemically and pharmacologically.

The following examples serve to illustrate certain preferred embodiments and aspects of the present invention and are not to be construed as limiting the scope thereof.

Experimental Section

In the experimental disclosure which follows, all weights are given in grams (g), milligrams (mg), micrograms (mg), nanograms (ng), picograms (pg) or moles (mol), all concentrations are given as percent by volume (%), molar (M), millimolar (mM), micromolar ($\mu$M), nanomolar (nM), or picomolar (pM), normal (N) and all volumes are given in liters (L), milliliters (mL) or microliters ($\mu$L), and measures in millimeters (mm), unless otherwise indicated.

The following examples demonstrate the isolation and synthesis of cryptophycin compounds as well as their use as therapeutic agents in accordance with the invention.

In screening extracts of over 1000 blue-green algae (cyanobacteria) for antitumor activity, the lipophilic extract of Nostoc sp. GSV 224 was found to be strongly cytotoxic,[3] exhibiting minimum inhibitory concentrations (MICs) of 0.24 ng/mL against KB, a human nasopharyngeal carcinoma cell line, and 6 ng/mL against LoVo, a human colorectal adenocarcinoma cell line. More importantly, this extract showed significant tumor selective cytotoxicity in the Corbett assay.[4,5] Bioassay monitored reversed-phase chromatography of the algal extract led to a fraction which was predominantly Cryptophycin 1, a potent fungicide that had been isolated earlier from Nostoc sp. ATCC 53789 by researchers at Merck[6,7] and found to be very active against strains of Cryptococcus.

Cryptophycin 1 accounted for most of the cytotoxic activity of the crude algal extract of Nostoc sp. GSV 224 and the pure compound showed $IC_{50}$ values of 3 and 5 pg/mL against KB and LoVo, respectively. In the Corbett assay Cryptophycin 1 was found to be strongly tumor selective and equally cytotoxic against drug-sensitive and drug-resistant tumor cells. Immunofluorescence assays showed that Cryptophycin 1 interact with a cellular target similar to that of vinblastine, but differed from the latter drug in having a longer time course of action and in not forming paracrystalline bodies. In preliminary in vivo experiments, Cryptophycin 1 exhibited very promising activity against tumors implanted in mice.

Minor amounts of several other cryptophycin compounds were present in Nostoc sp. GSV 224. Twenty-one of these could be isolated in sufficient quantities for structure determinations and antitumor evaluation in vitro by extraction of the alga with 1:5 dichloromethane/acetonitrile and reversed-phase HPLC of the extract. Cryptophycins 2, 3, 4, 16, 17, 18, 19, 21, 23, 24, 26, 28, 29, 30, 31, 40, 43, 45, 49, 50 and 54 accompanied Cryptophycin 1 in the fraction eluted from a reversed-phase flash column with 65:35 acetonitrile/water. Cryptophycins 2, 3, 4, 5, 6, and 7 were the only compounds found when the alga was extracted with methanol and the reversed-phase chromatography was carried out with methanol/water. Cryptophycins 2, 3, 4, 5 and 6 were eluted with 3:1 methanol/water and Cryptophycin 7 was found in an earlier, less cytotoxic fraction eluted with 1:3 methanol/water. Acyclic Cryptophycins 5, 6 and 7 appear to be artifacts generated by decomposition of Cryptophycin 1 during the isolation procedure.

Cryptophycins 3 and 5 appeared to be identical with fungicidal semi-synthetic compounds prepared from Cryptophycin 1 by researchers at Merck.[8,9] Cryptophycin 3 was prepared by treating Cryptophycin 1 with a zinc-copper couple or with diphosphorus tetraiodide.[8] Cryptophycin 5 was prepared by methanolysis of Cryptophycin 1.[9]

EXAMPLE 1

Structure Determination

The determination of the structures of the new cryptophycins, as well as those previously disclosed, were carried out in a straightforward manner using methodology that is well-known to those trained in the art. Mass spectral data were consistent with the molecular compositions. Proton and carbon NMR data obtained from COSY, HMQC, HMBC and NOESY spectra allowed one to assemble all of the gross structures of these depsipeptide-type compounds. The presence of the various hydroxy and amino acid units in each compound were confirmed by gas chromatographic mass spectral analysis. Total structures, including absolute stereochemistries, were determined using a combination of chemical degradative and special analytical techniques on appropriate derivatives of the cryptophycin compounds.

EXAMPLE 2

Structure-Activity Relationships (SAR)

To probe the structural features in Cryptophycin 1 needed for optimal activity, all of the compounds described herein were evaluated for cytotoxicity against KB (human nasopharyngeal carcinoma), LoVo (human colon carcinoma), and SKOV3 (human ovarian carcinoma) cell lines. $IC_{50}$ values are listed in Tables 1 and 2. Comparison of the cytotoxicities show that the intact macrolide ring, the epoxy and methyl groups and the double bond in the 7,8-epoxy-5-hydroxy-6-methyl-8-phenyl-2-octenoic acid unit (see Unit A in FIG. 1), the chloro and O-methyl groups in the 3-(3-chloro-4-methoxyphenyl)alanine unit (Unit B), the methyl group in the 3-amino-2-methylpropionic acid unit (Unit C), and the isobutyl group in the leucic acid unit (Unit D) of Cryptophycin 1 are needed for optimal cytotoxicity. The potent cytotoxicity of Cryptophycin 8 is most likely due to the chlorohydrin functionality which acts as a masked epoxide.

The most active compounds were also evaluated for selective cytotoxicity against four different cell types, viz. a murine leukemia (L1210 or P388), a murine solid tumor (colon adenocarcinoma 38, pancreatic ductal adenocarcinoma 03, mammary adenocarcinoma M16/M17), a human solid tumor (colon CX-1, HCT8, H116; lung H125; mammary MX-1, MCF-7), and a low malignancy fibroblast (LML), using the Corbett assay, 2 a disk diffusion assay modeled after the one commonly used in antifungal and antibacterial testing. The results, shown in Table 1, indicated that Cryptophycins 1–5 and 8 were neither solid tumor nor leukemia selective, but rather equally active against tumor cell lines, including drug-resistant ones such as M17. None of the compounds showed a zone of inhibition for any of the solid tumor cell lines that was $^3$250 zone units, i.e. $^3$7.5 mm, larger than the zone of inhibition for the leukemia cell line. Cryptophycins 1–5 and 8, however, displayed markedly larger zones of inhibition ($^3$400 zone units) for all of the tumor cell lines compared with the zone of inhibition for the fibroblast LML. Diagnostically LML has been found to behave more like a normal cell than a tumor cell with respect to clinically-useful cytotoxic agents (see Corbett assay data for 5-fluorouracil, etoposide and taxol in Table 1). Since the differential cytotoxicities were >250 zone units, Cryptophycins 1–5 and 8 were tumor selective. These compounds therefore became candidates for in vivo testing.

Cryptophycin 1 is active against a broad spectrum of murine and human tumors implanted in mice, including drug-resistant ones (Table 3). It exhibits excellent activity against five early stage murine tumors, viz. colon adenocarcinomas #38 and #51, taxol-sensitive and taxol-resistant mammary #16/C/RP, and pancreatic ductal adenocarcinoma #03, and two early stage human tumors tested in SCID mice, viz. MX-1 breast and H125 adenosquamous lung, showing tumor burden T/C (mean tumor burden in treated animals/ mean tumor burden untreated animals) values that are less than 10%.

T/C values that are less than 42% are considered to be active by NCI standards; T/C values that are less than 10% are considered to have excellent activity and potential clinical activity by NCI standards.[9] Two of the trials showed gross (tumor cell) log kill values of 2.0. Gross log kill is defmed as T-C/3.2 Td where T is the median time in days for the tumors of the treated group to reach 750 mg, C is the median time in days for the tumors of the control group to reach 750 mg, and Td is the tumor volume doubling time. Gross log kill values of >2.8, 2.0–2.8, 1.3–1.9, 0.5–0.8, and <0.5 with duration of drug treatment of 5–20 days are scored ++++, +++, ++, + and – (inactive), respectively. An activity rating of +++ to ++++, which is indicative of clinical activity, is needed to effect partial or complete regression of 100–300 mg size masses of most transplanted solid tumors of mice.

Cryptophycin 8 is also active against a broad spectrum of tumors implanted in mice (Table 4). It has shown excellent activity against all of the tumors tested to date, showing tumor burden T/C values <10%, but more importantly gross log kill activity ratings of +++ to ++++ and some cures.

Good in vivo activity was also seen with Cryptophycin 35 in the one trial that has been run to date.

Lethal toxicity observed during testing of Cryptophycins 1 and 8 was attributed to leucopenia which is common to all clinically used antitumor drugs.

TABLE 1

Cytotoxicity data for cryptophycins and semi-synthetic analogs. Corbett/Valeriote assay data for 5-fluorouracil, etoposide (VP-16) and taxol are included for comparison.

Type of Cytotoxicity (Differential in Zone Units)

| Compound | µg/disk | Corbett Assay[a] | µg/disk | Valeriote Assay[b] | KB $IC_{50}$ ng/mL | LoVo $IC_{50}$ ng/mL |
|---|---|---|---|---|---|---|
| 1 | 12.5 | E/T(>400)[c] | | N | 0.005 | 0.003 |
| 2 | 25 | E/T(>400)[c] | | N | 0.007 | 0.0002 |
| 3 | 25 | E/T(>400)[c] | | N | 0.3 | 0.5 |
| 4 | 20 | E/T(>400)[c] | | N | 1.3 | 0.5 |
| 5 | 2.9 | E/T(>600)[c] | | N | 0.02 | 0.02 |
| 6 | 250 | I | | | ≧100 | ≧100 |
| 7 | | | | | ≧750 | ≧480 |
| 8 | 30 | E/T(>500)[c] | 30 | N | 0.0002 | 0.01 |
| 9 | | | | | 15 | Not Determined |
| 10 | | | | | ≧100 | ≧100 |
| 12 | | | | | ≧100 | ≧100 |
| 14 | | | | | 1.8 | 3 |
| 5-FU | 2.5 | M/T(>400)[d] | 2.5 | LL(>400) | | |
| VP-16 | 5 | L(350), T(350)[d] | 5 | LL(260) | | |
| taxol | 0.2 | M/H/T (≧400)[d] | | | | |

[a]L = leukemia selective (e.g. $Z_{L1210} - Z_{C38}$ and $Z_{L1210} - Z_{H8} \geq 250$ zu)
M = murine solid tumor selective (e.g. $Z_{C38} - Z_{L1210} \geq 250$ zu)
H = human solid selective (e.g. $Z_{H8} - Z_{L1210} \geq 250$ zu)
E = equally cytotoxic towards leukemia and solid tumor cell lines (inhibition zones ≧ 250 zu)
T = tumor selective (e.g. $Z_{L1210} - Z_{LML}$, $Z_{C38} - Z_{LML}$, and $Z_{H8} - Z_{LML} \geq 250$ zu)
I = inactive (inhibition zones < 250)
[b]N = non-selective towards tumor (leukemia) and normal cell (CFU-GM) lines
LL = lymphocytic leukemia selective ($Z_{L1210} - Z_{CFU-M} \geq 250$ zu)
ML = acute myelogenous leukemia (AML) selective ($Z_{AML} - Z_{CFU-GM} \geq 250$ zu).
[c]Selective against drug-sensitive and drug-resistant cell lines ($Z_{C38} - Z_{LML}$, $Z_{M17} - Z_{LML}$ and $Z_{H8} - Z_{LML}$).
[d]Selective against drug-sensitive cell lines only.

TABLE 2

In Vitro Cytotoxicity Data of Cryptophycins

| Cryptophycin | $KBIC_{50}$ ng/mL | $LoVoIC_{50}$ ng/mL | $SKOV3IC_{50}$ ng/mL |
|---|---|---|---|
| 1 | 0.0025 | 0.001 | 0.026 |
| 2 | 0.023 | 0.021 | 0.18 |
| 3 | 1.8 | 0.6 | 2.8 |
| 4 | 6 | 2.5 | 21 |
| 5 | 12 | 2 | 7.4 |
| 8 | 0.01 | 0.0022 | 0.15 |
| 12 | 18 | 3 | |
| 15 | | | 12 |
| 16 | 0.08 | 0.02 | 0.64 |
| 17 | 4.7 | 5.9 | 11 |
| 18 | 15 | 4.5 | 23 |
| 19 | 9.8 | 5.9 | 41 |
| 21 | 0.01 | 0.0003 | 0.029 |
| 23 | 0.89 | 0.4 | 1.7 |
| 24 | 0.12 | 0.095 | 0.3 |
| 26 | 19 | 9.8 | 95 |
| 28 | 1.5 | 0.75 | 6.1 |
| 29 | 1 | 0.49 | 3.4 |
| 30 | 11 | 8 | 21 |

TABLE 2-continued

In Vitro Cytotoxicity Data of Cryptophycins

| Crypto-phycin | KBIC$_{50}$ ng/mL | LoVoIC$_{50}$ ng/mL | SKOV3IC$_{50}$ ng/mL |
|---|---|---|---|
| 31 | 0.53 | 0.062 | 1.9 |
| 35 | 0.055 | 0.01 | 0.092 |
| 40 | 9.0 | 1.0 | 1.7 |
| 43 | 0.72 | 0.8 | 1.1 |
| 45 | 2.3 | 2.4 | 1.6 |
| 49 | 1.4 | 1.9 | 1.1 |
| 50 | 0.17 | 0.17 | 0.2 |
| 54 | 0.80 | 2.2 | 2.2 |

TABLE 3

In Vivo Activity of Cryptophycin-1

| Exp # | SC Tumor | # of Inj. IV | mg/kg Total Dose | % Body Wt. Loss at Nadir | T/C | Log Kill | Cures |
|---|---|---|---|---|---|---|---|
| 1560 | Colon 38 | 8 | 10.3 | Gain | 6% | 1.5 | 0/5 |
| 1694 | Panc 03 | 8 | 16.0 | Gain | 0% | 2.0 | 0/5 |
| 1636 | Colon 51 | 7 | 28.1 | −11% | 7% | 1.3 | 0/5 |
| 1720 | Mam 16/C | 5 | 13.2 | −1% | 5% | 1.4 | 0/5 |
| 1733 | Mam 16/Taxol | 5 | 16.5 | 0% | 2% | 1.8 | 0/4 |
| 1833 | M17/0 (Adr. Sens.) | 5 | 5.4 | −10% | 23% | <1 | 0/5 |
| 1749 | Panc 02 | 5 | 11.0 | −5% | 20% | 1.1 | 0/5 |
| 1596 | Human Sm Cell L. DMS273 SCID | 6 | 7.3 | 0% | 27% | <1 | 0/5 |
| 1806 | MX-1 Human Breast | 8 | 12 | −3% | 3% | 2.0 | 0/5 |
| 1823 | H125 Human Adenosq-lung | 8 | 14.4 | −15% 1/5 dead | 9% | 1.1 | 0/5 |
| 1841 | LNCaP Human Prostate | 6 | 6.5 | −6% | 26% | <1 | 0/5 |

TABLE 4

In Vivo Activity of Cryptophycin Analogs

| Exp # | Agent | SC Tumor | # of Inj. IV | mg/kg TD | % Body Wt. Loss at Nadir | T/C | Log Kill | Cures |
|---|---|---|---|---|---|---|---|---|
| 1813 | Cryptophycin-2 | P03 | 10 | 37 | −2% | 44% | <1 | 0/5 |
| 1843 | Cryptophycin-3 | P03 | 4 | 28/5 | −9% | 54% | <1 | 0/5 |
| 1769 | Cryptophycin-8 | C38 | 15 | 45 | −2% | >100% | None | 0/5 |
| 1825 | Cryptophycin-8 | P03 | 11 | 106 | −6% | 4% | 4.6 | 0/5 |
| 1885 | Cryptophycin-8 | Mam 16/C | 7 | 21.3 | −4.5% | 6% | 2.5 | 0/5 |
| 1887B | Cryptophycin-8 | C38 | 6 | 30 | −2% | 0% | 2.8 | 1/5 |
| 1900 | Cryptophycin-8 | Colon 51 | 9 | 67.5 | −1% | 7% | 1.8 | 0/5 |
| 1843 | Cryptophycin-15 | P03 | 5 | 18 | −7% | 83% | None | 0/5 |
| 1878 | Cryptophycin-16 | P03 | 9 | 82 | −1% | 89% | None | 0/5 |
| 1813 | Cryptophycin-21 | P03 | 9 | 27 | −11% (1/5 dead) | 61% | None | 0/5 |
| 1843 | Cryptophycin-35 | P03 | 7 | 23 | −2% | 11% | 1.3 | 0/5 |

EXAMPLE 3

Culture Conditions

Nostoc sp. GSV 224 was obtained from Professor C. P. Wolk, MSU-DOE Plant Research Laboratory, Michigan State University. Nostoc sp. ATCC 53789 was purchased from the American Type Culture Collection. A 1 L flask culture of alga was used to inoculate an autoclaved 20 L glass carboy containing an inorganic medium, designated modified BG-11[3], the pH of which had been adjusted to 7.0 with NaOH. Cultures were continuously illuminated at an incident intensity of 200 μmol photons m$^{-2}$sec$^{-1}$ (photosynthetically active radiation) from banks of cool-white fluorescent tubes and aerated at a rate of 5 L/min with a mixture of 0.5% $CO_2$ in air at a temperature of 24+1° C. Typically, the culture was harvested by filtration after 21 days. The yields of lyophilized Nostoc sp. GSV 224 and ATCC 53789 averaged 0.61 and 0.3 g/L of culture, respectively.

EXAMPLE 4

Isolation

Method A

The lyophilized Nostoc sp. GSV224 (50 g) was extracted with 2 L of 1:5 $CH_2Cl_2$/$CH_3CN$ for 48 h and the extract concentrated in vacuo to give a dark green solid. The residue (1 g; KB MIC 0.24 ng/mL) was applied to an ODS-coated silica column (55 g, 7×5 cm) and subjected to flash chromatography with 1:3 $CH_3CN$/$H_2O$ (0.8 L), 1:1 $CH_3CN$/$H_2O$ (0.8 L), 65:35 $CH_3CN$/$H_2O$ (1.0 L), MeOH (0.8 L), and $CH_2Cl_2$ (0.5 L). The fraction that was eluted with 65:35 $CH_3CN$/$H_2O$ (420 mg; KB MIC 14 pg/mL) was subjected to reversed-phase HPLC (Econosil C18, 10 μm, 25 cm×21.5 mm, UV detection at 250 nm, 65:35 $CH_3CN$/$H_2O$, flow rate 6 mL/min) to obtain Cryptophycin 1 ($t_R$ 49.3 min, 220 mg) and a number of impure fractions. The fraction eluted from the Econosil C18 column at $t_R$ 28.8 min was further purified by normal phase HPLC (Econosil silica 5 m cartridge, 250×4.6 mm, 6:4 ethyl acetate/hexane, 3 mL/min) to give Cryptophycin 16 (3.0 mg). The fraction eluted from the Econosil C18 column at $t_R$ 32.5 min was subjected to HPLC on the Econosil silica column using 55:45 ethyl acetate/hexane at 3 mL/min to give Cryptophycin 24 (0.8 mg). The fraction eluted from the Econosil C18 column at $t_R$ 35.5 min was subjected to HPLC twice on the Econosil silica column, first using 1:1 ethyl acetate/hexane at 3 mL/min and second using 4:6 ethyl acetate /methylene chloride at 2.5 mL/min to give Cryptophycin 23 (1.2 mg) and Cryptophycin 43 (0.1 mg). The fraction eluted from the Econosil C18 column at $t_R$ 39.5 min was subjected to HPLC on the Econosil silica column with 1:1 ethyl acetate/hexane at 3 mL/min to give Cryptophycin 2 (6 mg) and Cryptophycin 21 (14 mg) and a complex mixture of Cryptophycins eluted at $t_R$ 32.5 min.

This latter fraction, accumulated from 400 gm dry alga, was chromatographed successively on a semi preparative column (partisil C18, 250×9.4 mm, 10 m) with 35:65 water/acetonitrile and a reversed phase analytical column (Econosil, 150×4.6 mm, 5 m) with 5:4:1 water/acetonitrile/methanol at 1.3 mL/min to give Cryptophycin 50 ($t_R$ 34.8, 0.4 mg) and Cryptophycin 40 ($t_R$ 38.8 min, 0.3 mg). The fraction eluted from the Econosil C18 column at $t_R$ 44.5 min was subjected to HPLC on the Econosil silica column with 1:1 ethyl acetate/hexane at 3 mL/min to give Cryptophycin 17 (0.3 mg). Normal phase HPLC purification of the fraction eluted from the Econosil C18 column at $t_R$ 54.5 as a shoulder to Cryptophycin 1 yielded Cryptophycin 45 ($t_R$ 6.7 min, 0.1 mg), Cryptophycin 26 ($t_R$ 8.9 min, 0.5 mg), and Cryptophycin 54 ($t_R$ 19.8 min, <0.1 mg) on elution with 1:1 ethyl acetate/hexane. The fraction eluted from the Econosil C18 column as a broad peak ($t_R$ 58 to 70 min) was subjected to HPLC on the Econosil silica column with 43:57 ethyl acetate/hexane at 2.5mL/min to give Cryptophycin 4 ($t_R$ 19.6 min, 1.5 mg), Cryptophycin 31 ($t_R$ 9.4 min, 0.8mg), Cryptophycin 19 ($t_R$ 25.8 min, 0.3 mg), Cryptophycin 49 ($t_R$ 28 min, 0.1 mg), Cryptophycin 28 ($t_R$ 29.0 min, 0.5 mg) and impure Cryptophycin 29 ($t_R$ 52.5 min, 2.0 mg) and Cryptophycin 30 ($t_R$ 49 min, 3.0 mg). Cryptophycins 29 and 30 obtained pure after reversed phase HPLC (Econosil C18, 10 m, 250×10 mm, 3:1 methanol/water). The fraction eluted from the Econosil C18 column at $t_R$ 78.9 min was subjected to HPLC on the Econosil silica column with to give Cryptophycin 3 ($t_R$ 16.4 min, 3.0 mg). The fraction eluted from the Econosil C18 column at $t_R$ 82.8 min was subjected to HPLC on the Econosil silica column with 45:55 ethyl acetate/hexane at 3 mL/min to give Cryptophycin 18 ($t_R$ 19.2, 0.8 mg).

Method B

The lyophilized Nostoc sp. GSV 224 (12.23 g) was extracted twice with 700 mL and 400 mL portions of MeOH for 12 and 5 hours (h), respectively. The extracts were combined and concentrated in vacuo to give 1.84 g of a dark green solid which was partitioned between water and $CH_2Cl_2$. The lipophilic portion (0.65 g; KB MIC 0.24 ng/mL) was applied to an ODS-coated silica column (55 g, 7×5 cm) and subjected to flash chromatography with 1:3 $MeOH/H_2O$ (0.8 L), 1:1 $MeOH/H_2O$ (0.8 L), 3:1 $MeOH/H_2O$ (0.8 L), MeOH (0.8 L), and $CH_2Cl_2$ (0.8 L). The fraction that was eluted with 3:1 $MeOH/H_2O$ (22 mg; KB MIC 14 pg/mL), which accounted for essentially all of the cytotoxic activity, was subjected to reversed-phase HPLC (Econosil C18, 10 μu, 250 cm×10 mm, UV detection at 250 nm, flow rate 3 mL/min) using 1:5 $MeOH/H_2O$ as the eluant to give Cryptophycins 7 ($t_R$ 7.6 min, 0.2 mg), 5 ($t_R$ 15.4 min, 2.3 mg), 2 ($t_R$ 16.0 min, 1.0 mg), 1 ($t_R$ 19.0 min, 12.0 mg), 4 ($t_R$ 26.5 min, 1.2 mg), and 3 ($t_R$ 30.2 min, 1.4 mg). From one of the cultures the fraction (8.1 mg) that eluted from the flash column with 1:3 $MeOH/H_2O$ showed milder cytotoxicity (KB MIC 2 μg/mL). Purification on HPLC using 2:3 $MeOH/H_2O$ as the eluant yielded cryptophycin G (7, $t_R$ 6.0 min, 2.4 mg).

EXAMPLE 5

Spectral Data for Cryptophycins 1–7

The bold italicized letters in the spectral data refer to the units A–D in FIG. 1.

Cryptophycin 1

$[α]_D$ +33.8°(MeOH, c 1.83); UV $λ_{max}(ε)$ 208 (42,400), 218 (33,700), 228 (23,800), 280 (2,210); CD $[θ]_{202}$ +15,900, $[θ]_{206}$ +64,900, $[θ]_{214}$ +26,900, $[θ]_{224}$ +46,300, $[θ]_{237}$ +10,500. IR ($CHCl_3$) $ν_{max}$ 3425, 2963, 1751, 1719, 1677, 1502, 1259 $cm^{-1}$. EIMS m/z (rel intensity) 654/656 (20/9), 412/414 (33/12), 280/282 (31/12), 227 (80), 195/197 (92/44), 91 (100); high resolution EIMS n/z 654.2665 (calcd for $C_{35}H_{43}ClN_2O_8$, 4.3 mmu error). $^1$H NMR ($CDCl_3$): amino or hydroxy acid unit δ (carbon position, multiplicity; J in Hz) 7,8-epoxy-S-hydroxy-6-methyl-8-phenyl-2-octenoic acid (A) 5.74 (2, dt; 15.5 and 0.9), 6.68 (3, ddd; 15.5, 9.6 and 5.2), 2.45 (4, ddd; 14.2, 11.1 and 9.6), 2.55 (4, brdd; 14.2 and 5.2), 5.16 (5, ddd; 11.1, 4.9 and 1.9), 1.80 (6, m), 1.14 (6-Me, d; 7.1), 2.92 (7, dd; 7.5 and 2.0), 3.69 (8, d; 2.0), 7.25 (10/14, m), 7.34–7.39 (11/12/13, m); leucic acid (D) 4.83 (2, dd; 6.8 and 3.3), 1.70 (3, m), 1.36 (3, m), 1.70(4, m), 0.86 (5, d; 6.6), 0.85 (5', d;6.6); 3-amino-2-methylpropionic acid (C) 2.71 (2, m), 1.22 (2-Me, d; 7.1), 3.30 (3, ddd; 13.4, 5.8 and 3.8), 3.48 (3, ddd; 13.4, 6.3 and 5.8), 6.93 (3-NH, brt; 5.8); 3-chloro-4-methoxyphenylalanine (B) 4.80 (2, ddd; 8.7, 7.3 and 5.4), 5.61 (2-NH, d; 8.7), 3.03 (3, dd; 14.4 and 7.3), 3.13 (3, dd; 14.4 and 5.4), 7.21 (5, d; 2.1), 3.87 (7-$OCH_3$,s), 6.83 (8, d; 8.5), 7.07 (9, dd; 8.5 and 2.1). $^{13}$C NMR ($CDCl_3$): unit δ (carbon position) A 165.3 (1), 125.3 (2), 141.0 (3), 36.7 (4), 76.2 (5), 40.6 (6), 13.5 (6-Me), 63.0 (7), 59.0 (8), 136.7 (9), 125.6 (10/14), 128.7 (11/13), 128.5 (12); D 170.7 (1), 71.3 (2), 39.4 (3), 24.5 (4), 22.9 (5), 21.3 (5'); C 175.6(1), 38.2 (2), 14.1 (2-Me), 41.1 (3); B 170.9 (1), 53.6 (2), 35.0 (3), 129.7 (4), 131.0 (5), 122.4 (6), 154.0 (7), 56.1 (7-$OCH_3$), 112.2 (8), 128.4 (9).

Cryptophycin 2

$[α]_D$ +20.4°(MeOH, c 0.54); UV $λ_{max}(ε)$ 206 (43,800), 218 (37,500), 232 (22,900), 278 (2,410); CD $[θ]_{203}$ +54,100, $[θ]_{212}$ +16,500, $[θ]_{225}$ +53,600, $[θ]_{236}$ −14,000. IR ($CHCl_3$) $ν_{max}$ 3423, 3029, 2961, 1742, 1724, 1678, 1512, 1258 $cm^{-1}$. EIMS m/z (rel intensity, assignment) 620 (11, M$^+$), 431 (3), 378(8), 377 (6), 311 (11), 246 (10), 244 (8), 227 (14), 195 (17), 161 (84, $CH_3O—C_6H_4—CH=CH=CO^+$), 121 (79, $CH_3O—C_6H_4—CH_2^+$), 91 (100); high resolution EIMS m/z 620.3094 (calcd for $C_{35}H_{44}N_2O_8$, 0.3 mmu error); 161.0605 (calcd for $C_{10}H_9O_2$, −0.2 mmu error); 121.0658 (calcd for $C_8H_9O$, −0.4 mmu error). $^1$H NMR ($CDCl_3$): amino or hydroxy acid unit δ (carbon position, multiplicity; J in Hz) 7,8-epoxy-5-hydroxy-6-metlyl-8-phenyl-2-octenoic acid (A) 5.71 (2, dd; 15.4 and 1.3), 6.70 (3, ddd; 15.4, 10.2 and 5.0), 2.45 (4, m), 2.55 (4, m), 5.18 (5, ddd; 11.3, 4.8 and 2.0), 1.79 (6, m), 1.14 (6-Me, d; 7.0), 2.92 (7, dd; 7.7 and 2.0), 3.68 (8, d; 2.0), 7.24 (10/14, m), 7.34–7.39 (11/12/13, m); leucic acid (D) 4.82 (2, dd; 10.1 and 3.7), 1.70 (3, m), 1.33 (3, m), 1.70 (4, m), 0.86 (5, d; 6.4), 0.84 (5', d; 6.4); 3-amino-2-methylpropionic acid (C) 2.68 (2, m), 1.23 (2-Me, d; 7.3), 3.39 (3-H$_2$, m), 7.02 (3-NH,brt; 6.0); O-methyltyrosine (B) 4.79 (2, ddd; 8.1, 7.0 and 5.7), 5.55 (2-NH, d; 8.1), 3.07 (3, dd; 14.5 and 7.0), 3.13 (3, dd; 14.5 and 5.7), 7.10 (5/9, d; 8.6), 6.81 (6/8, d; 8.6), 3.78 (7-$OCH_3$, s). $^{13}$C NMR ($CDCl_3$): unit δ (carbon position) A 165.1 (1), 125.1 (2), 141.1 (3), 36.7 (4), 76.0 (5), 40.7(6), 13.6 (6-Me), 63.0 (7), 59.0 (8), 136.7 (9), 125.6 (10/14), 128.7 (11/13), 128.5 (12); D 170.6(1), 71.3 (2), 39.4 (3), 24.5 (4), 21.3 (5), 22.9 (5'); C 176.0 (1), 38.1 (2), 14.2 (2-Me), 40.7 (3); B 171.1 (1), 53.9 (2), 35.3 (3), 131.0 (4), 130.2 (5/9), 114.1 (6/8), 158.6 (7), 55.2 (7-$OCH_3$).

Cryptophycin 3

$[α]_D$ +20.3°(MeOH, c 1. 13); UV $λ_{max}(ε)$ 206 (51,700), 218 (31,200), 230 (22,900), 246 (18,800), 280 (3,230); CD $[θ]_{205}$ +50,000, $[θ]_{212}$ −390, $[θ]_{218}$ −47,200, $[θ]_{233}$ −100, $[θ]_{251}$ +33,400, $[θ]_{271}$ +4,310. IR ($CHCl_3$) $ν_{max}$ 3417, 2926, 1742, 1721, 1676, 1499, 1336 $cm^{-1}$. EIMS m/z (rel intensity) 638/640 (2/0.7, M$^+$), 412/414 (63/19), 280/282 (15/5), 227 (100), 195 (63), 91 (98); high resolution EIMS m/z 638.2764 (calcd for $C_{35}H_{43}ClN_2O_7$, −0.5 mmu error), 412.1516 (calcd for $C_{20}H_{27}ClNO_6$, 1.1 mmu error), 227.1293 (calcd for $C_{15}H_{17}NO$, 1.0 mmu error). $^1$H NMR ($CDCl_3$): amino or hydroxy acid unit δ (carbon position, multiplicity; J in Hz) 5-hydroxy-6-methyl-8-phenyl-2,7-octadienoic acid (A) 5.77 (2, d; 15.5), 6.68 (3, ddd; 15.5, 9.5 and 5.3), 2.37 (4, m), 2.54 (4, m), 5.01 (5, ddd; 11.4, 6 and 1.5), 2.56 (6, m), 1.14 (6-Me, d; 7.0), 6.01 (7, dd; 15.8 and 8.8), 6.41 (8, d; 15.8), 7.28–7.34 (10/11/13/14, m), 7.23 (12, m); leucic acid (D) 4.84 (2, dd; 10.1 and 3.6), 1.62 (3, m), 1.36 (3, m), 1.62 (4, m), 0.77 (5, d; 6.5), 0.73 (5', d; 6.3); 3-amino-2-methylpropionic acid (C) 2.71 (2, m), 1.22 (2-Me, d; 7.3), 3.28 (3, dt; 13.5 and 7.0), 3.50 (3, ddd; 13.5, 4.9 and 4), 6.93 (3-NH, brt; 6.3); 3-chloro-4-methoxyphenylalanine (B) 4.82 (2, m), 5.64 (2-NH, d; 8.8), 3.05 (3, dd; 14.5 and 7.0), 3.13 (3, dd; 14.5 and 5.5), 7.22 (5, d; 2.2), 3.87 (7-OCH$_3$, s), 6.84 (8, d; 8.5), 7.08 (9, dd; 8.5 and 2.2). $^{13}$C NMR (CDCl$_3$): unit δ (carbon position) A 165.4 (1), 125.2 (2), 141.4 (3), 36.5 (4), 77.1 (5), 42.3 (6), 17.3 (6-Me), 130.1(7), 130.0 (8), 136.7 (9), 126.1 (10/14), 128.6 (11/13), 128.4 (12); D 170.1(1), 71.6 (2), 39.5 (3), 24.5 (4), 21.2 (5), 22.7 (5'); C 175.6 (1), 38.3 (2), 14.0 (2-Me), 41.2 (3); B 170.9 (1), 53.5 (2), 35.1 (3), 129.8 (4), 131.0 (5), 122.4 (6), 154.0 (7), 56.1 (7-OCH$_3$), 112.2 (8), 127.6 (9).

Cryptophycin 4

[α]$_D$ +36.7°(MeOH, c 1.93); UV λ$_{max}$(ε) 206 (41,800), 228 (25,000), 240 (21,200), 248 (22,500), 280 (3,000), 290 (1,230); CD [θ]$_{205}$ +63,900, [θ]$_{211}$ +3,040, [θ]$_{218}$ −71,900, [θ]$_{229}$ −11,700, [θ]$_{234}$ −130,[θ]$_{252}$ +47,500, [θ]$_{270}$ +5,400. IR (CHCl$_3$)ν$_{max}$ 3410, 2962, 2917, 1741, 1718, 1678, 1511, 1251 cm$^{-1}$. EIMS m/z (rel intensity) 604 (2, M+), 378 (74), 246 (11), 227 (46), 161 (100), 91 (96); high resolution EIMS m/z 604.3127 (calcd for C$_{35}$H$_{44}$N2O$_7$, 2.2 mmu error), 378.1910 (calcd for C$_{20}$H$_{28}$NO$_6$, 0.7 mmu error), 227.1293 (calcd for C$_{15}$H$_{17}$NO, 1.7 mmu error), 161.0605 (calcd for C$_{10}$H$_9$O$_2$, −0.2 mmu error). $^1$H NMR (CDCl$_3$): amino or hydroxy acid unit δ (carbon position, multiplicity; J in Hz) 5-hydroxy-6-methyl-8-phenyl-2,7-octadienoic acid (A) 5.74 (2, dd; 15.3 and 1.2), 6.71 (3, ddd; 15.3, 10.3 and 5.0), 2.37 (4, m), 2.53 (4, m), 5.03 (5, ddd; 11.2, 6.4 and 2.0), 2.55 (6, m), 1.13 (6-Me, d; 6.8), 6.01 (7, dd; 15.8 and 8.8), 6.40 (8, d; 15.8), 7.28–7.37 (10/11/13/14, m), 7.22 (12, m); leucic acid (D) 4.84 (2, dd; 10.1 and 3.6), 1.65 (3, m), 1.34 (3, m), 1.65 (4, m), 0.75 (5, d; 6.5), 0.72 (5', d; 6.3); 3-amino-2-methylpropionic acid (C) 2.69 (2, m), 1.22 (2-Me, d; 7.5), 3.39 (3-H$_2$, m), 7.03 (3-NH, brt; 6.0); O-methyltyrosine (B) 4.79 (2, m), 5.61 (2-NH, d; 7.8), 3.08 (3, dd; 14.5 and 7.0), 3.13 (3, dd; 14.5 and 5.3), 7.11 (5/9, d; 8.8), 6.81 (6/8, d; 8.8), 3.78 (7-OCH$_3$, s). $^{13}$C NMR (CDCl$_3$): unit δ (carbon position) A 165.3 (1), 125.1 (2), 141.5 (3), 36.5 (4), 77.1 (5), 42.3 (6), 17.3 (6-Me), 130.1 (7), 131.8 (8), 136.7 (9), 126.2 (10/14), 128.7 (11/13), 127.6 (12); D 170.8 (1), 71.6 (2), 39.5 (3), 24.5 (4), 21.2 (5), 22.7 (5'); C 175.9 (1), 38.2 (2), 14.2 (2-Me), 40.9 (3); B 171.2 (1), 53.8 (2), 35.3 (3), 131.0 (4), 130.2 (5/9), 114.6 (6/8), 158.6 (7), 55.2 (7-OCH$_3$).

Cryptophycin 5

[α]$_D$ +36.0°(MeOH, c 0.55); UV λ$_{max}$(ε) 206 (45,600), 218 (37,700), 280 (3,790), 286 (3,480), 325 (2,080); CD [θ]$_{203}$ +7,710, [θ]$_{206}$ +29,000, [θ]$_{210}$ +21,400, [θ]$_{222}$ +59, 800, [θ]$_{234}$ +12,800, [θ]$_{241}$ +13,700. IR (CHCl$_3$) ν$_{max}$ 3426, 2958, 1728, 1672, 1502, 1259 cm$^{-1}$. EIMS m/z (rel intensity) 686/688 (0.1510.05), 655/657 (1/0.3), 654/656 (1.5/0.5), 311/313 (75/27), 195 (66), 155 (54), 121 (51), 91 (100); high resolution EIMS m/z 686.2983 (calcd for C$_{36}$H$_{47}$ClN$_2$O$_9$, −1.3 mmu error). $^1$H NMR (CDCl$_3$): amino or hydroxy acid unit δ (carbon position, multiplicity; J in Hz) 7,8-epoxy-5-hydroxy-6-methyl-8-phenyl-2-octenoic acid (A) 5.87 (2, d; 15.3), 6.72 (3, dt; 15.3 and 6.8), 2.60 (4, m), 2.52 (4, ddd; 15.2, 7.8, and 6.8), 5.11 (5, ddd; 12.3, 7.8, and 7.1), 1.87 (6,m), 1. 12 (6-Me, d; 7.1), 2.91 (7, dd; 7.3 and 2.1), 3.70 (8, d; 2.1), 7.24 (10/14, brd; 7.4), 7.29–7.36 (11/12/13, m); leucic acid (D) 4.09 (2, m), 2.86 (2-OH, brd, 6.1), 1.83 (3, m), 1.42 (3, m), 1.86 (4, m), 0.90 (5, d; 6.6), 0.87 (5', d; 6.8); 3-amino-2-methylpropionic acid (C) 3.64 (I—OCH$_3$, s), 2.60 (2, m), 1.07 (2-Me, d; 7.3), 3.27 (3, ddd; 13.5, 8.0 and 5.5), 3.39 (3, m), 6.32 (3-NH, t; 5.4); 3-chloro-4-methoxyphenylalanine (B) 4.59 (2, dt; 6 and 7.5), 6.30 (2-NH, d; 7.5), 2.95 (3, dd; 13.6 and 7.5), 3.0 (3, dd; 13.6 and 6.0), 7.2 (5, d; 2. 1), 3.86 (7-OCH$_3$, s), 6.84 (8, d; 8.5), 7.05 (9, dd, 8.5; 2.1). $^{13}$C NMR (CDCl$_3$): unit δ (carbon position) A 164.8 (1), 126.5 (2), 139.2 (3), 34.4 (4), 75.5 (5), 39.2 (6), 12.9 (6-Me), 63.3 (7), 58.7 (8), 136.8 (9), 125.7 (10/14), 128.6 (11/13), 128.4 (12); D 175.1 (1), 69.2 (2), 43.2 (3), 24.3 (4), 21.2 (5), 23.2 (5'); C 175.4 (1), 51.9 (1-OMe), 39.1 (2), 14.7 (2-Me), 41.6 (3); D 170.6 (1), 54.6 (2), 37.4 (3), 129.5 (4), 131.0 (5), 122.4 (6), 154.1 (7), 56.1 (7-OMe), 112.2 (8), 128.4 (9).

Cryptophycin 6

[α]$_D$ +17.1°)(MeOH, c 1.1); UVλ$_{max}$(ε) 206 (40,000), 218 (30,100), 228 (21,400), 282 (2,430); CD [θ]$_{203}$ +37,700, [θ]$_{210}$ −5,430, [θ]$_{213}$ −1,260, [θ]$_{221}$ +24,100, [θ]$_{232}$ +8,480, [θ]$_{240}$ +13,400, [θ]$_{254}$ +790. IR (CHCl$_3$) ν$_{max}$ 3425, 3006, 2956, 1726, 1672, 1641, 1502, 1462, 1259 cm$^{-1}$. FABMS (thioglycerol) m/z, (rel intensity) 573/575 (13/6) [M-H$_2$O]$^+$, 217 (26), 91 (100). $^1$H NMR(CDCl$_3$): amino or hydroxy acid unit δ (carbon position, multiplicity; J in Hz) 5,7,8-triydroxy-6-methyl-8-phenyl-2-octenoic acid (A) 5.92 (2, dt; 15.0 and 1.5), 6.94 (3, dt; 15 and 7.5), 2.51 (4, m), 2.64 (4, m), 3.97 (5, ddd; 9.3, 6.5 and 4.5), 2.03 (6, m), 1.10 (6-Me, d; 6.5), 3.70 (7, dd; 9.0 and 7.5), 4.64 (8, d; 7.5), 7.33–7.39 (10/11/13/14, m), 7.28 (12, tt; 6.5 and 2.0); 3-chloro-4methoxyphenylalanine (B) 4.60 (2, td; 8.0 and 6.0), 6.09 (2-NH, brd; 8.0), 2.96 (3, dd; 13.8 and 8.0), 3.02 (3, dd; 13.8 and 6.0), 7.22 (5, d; 2.0), 3.86 (7-OCH$_3$, s), 6.84 (8, d; 8.5), 7.07 (9, dd;. 8.5 and 2.0) 3-amino-2-methylpropionic acid (C) 3.63 (1-OCH$_3$,s), 2.58 (2, m), 1.07 (2-Me, d; 7.0), 3.24 (3, ddd; 13.8, 8 and 6.5), 3.41 (3, ddd; 13.8, 6.5 and 4.8), 6.21 (3-NH, brt; 6.5). $^{13}$C NMR (CDCl$_3$): unit δ (carbon position) A 165.2 (1), 125.6 (2), 141.3 (3), 36.9 (4), 82.5 (5), 46.3 (6), 14.3 (6-Me), 85.1 (7), 84.8 (8), 140.9 (9), 125.8 (10/14), 128.6 (11/13), 127.8 (12); B 170.6 (1), 54.5 (2), 37.3 (3), 129.6 (4), 131.0 (5), 122.5 (6), 154.1 (7), 56.1 (7-OCH$_3$), 112.2 (8), 128.5 (9) C52.0 (1-OCH$_3$), 175.4 (1), 39.2 (2), 14.7 (2-Me), 41.6 (3).

Cryptophycin 7

[α]$_D$ −51.9°(MeOH, c 0.89); UV λ$_{max}$(ε) 206 (23,400), 220 (14,900), 282 (1,670); CD [θ]$_{202}$ +35,400, [θ]$_{206}$ −1,730, [θ]$_{211}$ −19,200, [θ]$_{220}$ −15,800, [θ]$_{232}$ +29,000, [θ]$_{263}$ +2,040. IR (CHCl$_3$) ν$_{max}$ 3426, 2946, 1732, 1675, 1501, 1258 cm$^{-1}$. EIMS m/z (rel intensity) 455/457 (1/0.3, [M-2H$_2$O]$^+$), 105 (100), 77 (98); FABMS m/z (magic bullet matrix) 496/498 [M-H$_2$O+Na]$^+$, (thioglycerol matrix) 474/476 [M-H$_2$O1+H]$^+$. $^1$H NMR (CD$_3$OHD): amino or hydroxy acid unit δ (carbon position, multiplicity; J in Hz) 5,7,8-trihydroxy-6-methyl-8-phenyl-2-octenoic acid (A) 6.06 (2, ddd; 15.5, 1.3 and 1.0), 6.80 (3, dt; 15.5 and 7.5), 2.49 (4, m), 2.59 (4, m), 3.92 (5, ddd; 9.5, 6.3 and 4.7), 1.95 (6, m), 1.08 (6-Me, d; 6.7), 3.59 (7, dd; 9.0 and 7.8), 4.56 (8, d; 7.8), 7.37 (10/14, brd; 7.3), 7.31 (11/13, brt; 7.3), 7.24 (12, tt; 7.3 and 1.5); 3-chloro-4-methoxyphenylalanine (B) 4.52 (2, dd; 6.9 and 5.0), 2.93 (3, dd; 13.8 and 6.9), 3.15 (3, dd; 13.8 and 5.0), 7.20 (5, d; 2.2), 3.78 (7-OCH$_3$, s), 6.88 (8, d; 8.4), 7.08 (9, dd; 8.4 and 2.2). $^{13}$C NMR (CD$_3$OD): unit δ (carbon position) A 167.4 (1), 127.6 (2), 140.9 (3), 37.9 (4), 84.0 (5), 47.6 (6), 14.4 (6-Me), 86.0 (7), 85.8 (8), 142.9 (9), 127.1 (10/14), 129.3 (11/13), 128.5 (12); B 177.6 (1), 57.3 (2), 38.2 (3), 132.8 (4), 132.1 (5), 122.9 (6), 155.0 (7), 56.5 (7-OCH$_3$), 113.2 (8), 130.1 (9).

Cryptophycin 16

[α]$_D$ +41.3°(MeOH, c 5.2); UV λ$_{max}$(ε) 242 (4963), 280 (2430), 286 (2212); IR (neat) ν$_{max}$ 3402, 3270, 2960, 1748, 1724, 1676, 1514, 1466, 1343, 1239, 1177 cm$^{-1}$; EIMS m/z (rel intensity) 640/642 (66/27), 398/400 (47/16), 265 (55), 227 (93), 181 (100); high resolution EIMS m/z 640.25676 (calcd for C$_{34}$H$_{41}$ClN$_2$O$_{8b}$ , $_{-1.6}$ mmu error). $^1$H NMR (CDCl$_3$): amino or hydroxyacid unit δ (carbon position, multiplicity; J in Hz) 7, 8-epoxy-5-hydroxy-6-methyl-8-phenyl-2-octenoic acid (A) 5.74 (2, d; 16), 6.67 (3, ddd;

15.3, 9.7 and 5.5), 2.45 (4, dt; 14.3 and 10.4), 2.55 (4, brdd; 14.3 and 5.3), 5.15 (5, ddd; 11.2, 4.8 and 1.8), 1.8 (6, m), 1.14 (6-Me, d; 7.0), 2.92 (7, dd; 7.5 and 2.0), 3.69 (8, d; 2.0), 7.24–7.26 (10/14, m), 7.33–7.39 (11/12/13, m); 3-chloro-4-hydroxyphenylalanine (B) 4.8 (2, m), 5.64 (2-NH, d; 8.8), 3.03 (3, dd; 14.5 and 7.0), 3.11 (3, dd; 14.4 and 5.6), 7.17 (5, d; 2.2), 5.61(7-OH, s), 6.91 (8, d; 8.3), 7.0 (9, dd; 8.3 and 2.2); 3-amino-2-methylpropionic acid (C) 2.71 (2, m), 1.22 (2-Me, d; 7.3), 3.28 (3, dt; 13.6 and 6.8), 3.49 (3, ddd; 13.6, 5 and 4.1), 6.92 (3-NH, br t; 6.1); leucic acid (D) 4.83 (2, dd; 10.1 and 3.3), 1.36 (3, m), 1.67–1.75 (3, m), 1;67–1.75 (4, m), 0.85 (5, d; 7.5), 0.86 (5', d; 6.8). $^{13}$C NMR (CDCl$_3$) unit δ (carbon position) A 165.3 (1), 125.3 (2), 141.0 (3), 36.7 (4), 76.2 (5), 40.6 (6), 13.5 (6-Me), 63.0 (7), 59.0 (8), 136.8 (9), 125.6 (10/14), 128.7 (11/13), 128.6 (12); B 170.9 (1), 53.6 (2), 35.1 (3), 129.9 (4), 129.6 (5), 120.0 (6), 150.4 (7), 116.4 (8), 129.2 (9); C 175.6 (1), 38.3 (2), 14.1 (2-Me), 41.1 (3); D 170.8 (1), 71.3 (2), 39.4 (3), 24.6 (4), 21.3 (5), 22.9 (5').

Cryptophycin 17

$[\alpha]_D$ +27.8°(CHCl$_3$c. 0.37); UV λ$_{max}$ (ε) 248 (14740), 268 (8100), 278 (3400), 284 (2840); IR (neat) ν$_{max}$ 3412, 2958, 1750, 1723, 1668, 1504, 1463, 1290, 1177, 751 cm$^{-1}$; EIMS m/z (rel intensity) 624/626 (10/3), 398/400 (95/35), 284 (100), 149 (95); high resolution EIMS m/z 624.26161 (calcd for C$_{34}$H$_{41}$ClN$_2$O$_7$, −1.4 mmu error). $^1$H NMR (CDCl$_3$): amino or hydroxyacid unit δ (carbon position, multiplicity; J in Hz) 5-hydroxy-6-methyl-8-phenyl-2,7-octadienoic acid (A) 5.77 (2, d; 15.4), 6.67 (3, ddd; 15.4, 9.5, and 5.3), 2.37 (4, m ), 4.99 (5, ddd; 11.2, 6.3, and 1.6), 2.54 (6, m), 1.14 (6-Me, d; 6.7), 6.01 (7, dd; 15.7, and 8.7), 6.41 (8, d; 15.9), 7.28–7.34 (10/11/13/14, m), 7.23 (12, m); 3-chloro-4-hydroxyphenylalanine (B) 4.82 (2, m), 5.63 (2-NH, d; 8.7), 3.12 (3, dd; 14.7, and 5.6), 3.03 (3', dd; 14.7, and 7.1), 7.18 (5, d; 2.0), 5.47 (7-OH, br s), 6.91 (8, d; 8.3), 7.02 (9, dd; 8.3, and 2.0); 3-amino-2-methylpropionic acid (C) 2.71 (2, m), 1.21 (2-Me, d' 6.9), 3.25 (3, m), 3.52 (3', m), 6.89 (3-NH, br t; 6.1); luecic acid (D) 4.84 (2, dd; 9.6, and 3.1), 1.62 (3, m), 1.36 (3', m), 1.62 (4, m), 0.77 (5, d' 6.5), 0.73 (5', d; 6.5); $^{13}$C NMR (CDCl$_3$) unit δ (carbon position) A 165.4 (1), 125.3 (2), 141.3 (3), 36.5 (4), 77.1 (5), 42.3 (6), 17.3 (6-Me), 130.0 (7), 129.9 (8), 136.7 (9), 126.2 (10/14), 128.6 (11/13), 127.6 (12); B 170.9 (1), 53.5 (2), 35.1 (3), 129.6 (4), 131.9 (5), 126.2 (6), 150.3 (7), 116.3 (8), 127.6 (9); C 175.9 (1), 38.4 (2), 13.9 (2-Me), 41.3 (3); D 170.9 (1), 71.6 (2), 39.5 (3), 24.5 (4), 21.2 (5), 22.7 (5').

Cryptophycin 18

$[\alpha]_D$ +54.9°(MeOH, c 0.93); UV λ$_{max}$(ε) 250 (20518), 284 (3857); IR (neat) ν$_{max}$ 3411, 3271, 2966, 1746, 1728, 1668, 1505, 1463, 1258, 1178 cm$^{-1}$; EIMS m/z (rel intensity) 638/640 (4.5/1.1), 412/414 (59/19), 280(17), 227 (100); high resolution EIMS m/z 638.272934 (calcd for C$_{35}$H$_{43}$ClN$_2$O$_7$, 2.9 mmu error). $^1$H NMR (CDCl$_3$): amino or hydroxy acid unit δ (carbon position, multiplicity; J in Hz) 5-hydroxy-6-methyl-8-phenyl-2,7-octadienoic acid (A) 5.76 (2, d; 15.5), 6.65 (3, ddd; 15.4, 9.2 and 6.2), 2.38–2.47 (4, m), 5.08 (5,ddd; 10.6, 4.9 and 2.2), 2.58 (6, m), 1.15 (6-Me, d; 6.8), 6.07 (7, dd; 15.9 and 8.5), 6.43 (8, d; 15.9), 7.21–7.35 (10/11/12/13/14, m); 3-chloro-4methoxy-phenylalanine (B) 4.83 (2, m), 3.05(3, dd; 14.5 and 7.1), 5.65 (2-NH, d; 8.7), 3.14 (3, dd; 14.4 and 5.5), 7.21 (5, d; 2.4), 3.86 (7-OCH$_3$, s), 6.83 (8, d; 8.3), 7.08 (9, dd; 8.3 and 2.2); 3-amino-2-methylpropionic acid (C) 2.73 (2, m), 1.23 (2-Me, d; 7.2), 3.23 (3, dt; 13.5 and 6.8), 3.56 (3, ddd; 13.5, 5.7 and 4.0), 6.85 (3-NH, dd; 7.1 and 6.2); leucic acid (D) 4.8 (2, d; 4.6), 1.86–1.89 (3, m), 0.94 (3-Me, d; 7.0), 1.20–1.26 (4, m), 1.39–1.44 (4, m), 0.77 (5, d; 7.4). $^{13}$C NMR (CDCl$_3$) unit δ (carbon position) A 165.5 (1), 125.2 (2), 141.5 (3), 36.4 (4), 77.5 (5), 41.9 (6), 17.1 (6-Me), 129.8 (7), 131.9 (8), 136.8 (9), 128.6 (10/14), 126.2 (11/13), 127.6 (12); B 170.0 (1), 53.5 (2), 35.1 (3), 129.4 (4), 131.1 (5), 122.4 (6), 153.9 (7), 56.1 (7-OCH3), 112.2 (8), 128.5 (9); C 175.3 (1), 38.6 (2), 14.0 (2-Me), 41.4 (3); D 169.5 (1), 76.6 (2), 36.2 (3), 15.5 (3-Me), 24.2 (4), 14.0 (5).

Cryptophycin 19

$[\alpha]_D$ +62.6°(MeOH, c 0.67); UV (MeOH) λ$_{max}$ (ε) 204 (44900), 230 (17000), 248 (15600), 280 (2500); IR (neat) ν$_{max}$ 3413, 3272, 2966, 1745, 1726, 1672, 1504, 1258, 1199, 1178, 1066, 692 cm$^{-1}$; EIMS m/z (rel intensity) 624/626 (3.0/1.4), 398/400 (58/21), 280/282(15/5), 227 (100), 195/197 (57/22); high resolution EIMS m/z 624.2585 (calcd for C$_{34}$H$_{41}$ClN$_2$O$_7$, 1.8 mmu error). $^1$H-NMR (CDCl$_3$):amino or hydroxy acid unit δ (carbon position, multiplicity; J in Hz) 5-hydroxy-6-methyl-8-phenyl-2,7-octadienoic acid (A) 5.76 (2, d; 15.2), 6.64 (3, ddd; 15.4, 9.1 and 6.2), 2.38 (4, m), 2.47 (4, m), 5.04 (5, ddd;7.1, 5.1 and 1.8), 2.57 (6, m), 1.15 (6-Me, d; 6.9), 6.05 (7, dd; 15.8 and 8.5), 6.43 (8, d; 15.8), 7.29–7.35 (10/11/13/14, m), 7.23 (12, m); 3-chloro-4-methoxyphenylalanine (B) 4.84 (2, m), 5.67 (2-NH, d; 8.9), 3.04(3, dd; 14.3 and 7.1), 3.14 (3, dd; 14.3 and 5.3), 7.22 (5, d; 2.0), 3.86 (7-OCH$_3$, s), 6.83 (8, d; 8.2), 7.08 (9, dd; 8.2 and 2.0); 3-amino-2-methylpropionic acid (C) 2.75 (2, m), 1.23 (2-Me, d; 7.1), 3.19 (3, m), 3.59 (3, m), 6.80 (3-NH, brt; 6.7); 2-hydroxyisovaleric acid (D) 4.73 (2, d; 4.2), 2.09 (3, m), 0.84 (4, d; 6.9), 0.95 (4', d; 6.9). $^{13}$C NMR (CDCl$_3$) unit δ (carbon position) A 165.5 (1), 125.3 (2), 141.3 (3), 36.3 (4), 77.7 (5), 42.0 (6), 17.1 (6-Me), 129.9 (7), 131.9 (8), 136.8 (9), 126.1 (10/14), 128.6 (11/13), 127.6 (12); B 171.0 (1), 53.4 (2), 35.1 (3), 130.0 (4), 131.1 (5), 122.4 (6), 153.9 (7), 56.1 (7-OMe), 112.2 (8), 128.5 (9); C 175.1 (1), 38.7 (2), 13.9 (2-Me), 41.5 (3); D 169.6 (1), 76.9 (2), 29.8 (3), 19.0 (4), 16.7 (3-Me).

Cryptophycin 21

$[\alpha]_D$ +40.2°(CHCl$_3$ c 0.72); UV λmax (ε) 240 (6700), 280 (2400), 288 (2100); IR (neat) ν$_{max}$ 3403, 3279, 2957, 1731, 1673, 1503, 1464, 1409, 1372, 1258, 1174, 1065, 1023, 889 cm$^{-1}$; EIMS m/z (relative intensity) 640/642 (10/4), 612 (5), 478 (15), 398 (40), 266 (33), 227 (76), 195 (95), 155 (100), 127 (90); high resolution EIMS m/z 640.2550 (calcd for C$_{34}$H$_{41}$ClN$_2$O$_8$, 0.2 mmu error); $^1$H NMR (CDCl$_3$) amino or hydroxy acid unit δ (carbon positions, multiplicities; J in Hz) 7,8-epoxy-5-hydroxy-6-methyl-8-phenyl octanoic acid (A ) 5.73 (2, d; 15.4), 6.68 (3, ddd; 15.0, 9.9 and 4.9), 2.45 (4, m), 2.56 (4, m), 5.19 (5, ddd; 11.2, 5.1 and 1.5), 1.80 (6, m), 1.14 (6-Me, d; 7.1), 2.92 (7, dd; 7.5 and 2.0), 3.68 (8, d; 1.8), 7.25 (10/14, m), 7.33–7.38 (11/12/13, m); 3-chloro-4methoxyphenylalanine (B) 4.74 (2, ddd; 8.2, 6.8 and 6.2), 5.68 (2-NH, d; 8.6), 2.98 (3, dd; 14.3 and 7.7), 3.14 (3, dd; 14.3 and 5.6), 7.21 (5, d; 2.0), 3.86 (7-OMe, s), 6.83 (8, d; 8.4), 7.07 (9, dd; 8.4 and 2.0); 3-aminopropionic acid (C) 2.56 (2, m), 3.51 (3, m), 3.45 (3, m), 6.90 (3-NH, br t; 5.8); leucic acid (D) 4.89 (2, dd; 10.0 and 3.3), 1.67 (3, m), 1.31 (3, m), 1.67 (4, m), 0.84 (5, d; 6.4), 0.83 (5', d; 6.4); $^{13}$C NMR (CDCl$_3$) unit δ (carbon position) A 165.5 (1), 125.3 (2), 141.0 (3), 36.7 (4), 75.9 (5), 40.6 (6), 13.5 (6-Me), 63.0 (7), 59.0 (8), 136.7 (9), 125.6 (10/14), 128.7 (11/13), 128.5 (12); B 170.7 (1), 53.9 (2), 35.0 (3), 129.8 (4), 130.9 (5), 122.4 (6), 153.9 (7), 56.1 (7-OMe), 112.2 (8), 128.3 (9); C 172.6 (1), 32.4 (2), 34.4 (3), D 170.5 (1), 71.2 (2), 39.5 (3), 24.4 (4), 22.8 (5), 21.2 (5').

Cryptophycin 23

$[\alpha]_D$ +47°(MeOH, c 1.55); UV λ$_{max}$(ε) 240 (4571), 282 (2174), 290 (2177); IR (neat) ν$_{max}$ 3284, 2960, 1747, 1724, 1653, 1540, 1490, 1339, 1272, 1174 cm$^{-1}$; EIMS m/z (rel intensity) 674/675/678 (47/35/8), 432/434/436 (11/5/2), 299/301/303 (39/30/7), 227 (64), 215/217/219 (31/20/8), 141 (100); high resolution EIMS m/z 674.21643 (calcd. for C$_{34}$H$_4$Cl$_2$N$_2$O$_8$, −0.3 mmu error); $^1$H NMR (CDCl$_3$) amino or hydroxyacid unit δ (carbon position, multiplicity; J in Hz) 7,8-epoxy-5-hydroxy-6-methyl-8-phenyl-2-octenoic acid (A) 5.77 (2, d; 15.4), 6.65 (3, ddd; 15.4, 9.3 and 6.0), 2.47 (4, dt; 14.2 and 10.2), 2.55 (4, br dd; 14.2 and 5.6), 5.13 (5, ddd; 11.0, 4.6 and 1.6), 1.81 (6, m), 1.15 (6-Me, d; 6.9), 2.93 (7, dd; 7.6 and 2.0), 3.7 (8, d; 2.0), 7.22–7.26 (10/14, m), 7.32–7.39 (11/12/13, m); 3,5-dichloro-4-hydroxyphenylalanine (B) 4.81 (2, m), 5.69 (2-NH, d; 8.6), 3.11 (3, dd; 14.5 and 5.6), 3.50 (3, dd; 14.3 and 7.0), 7.13 (5/9, s), 5.78 (7-OH, s); 3-amino-2-methylpropionic acid (C) 2.73 (2, m), 1.22 (2-Me, d; 7.1), 3.19 (3, dt; 13.4 and 6.9), 3.58 (3, ddd; 13.6, 5.8 and 4.1), 6.82 (3-NH, br t; 5.9); leucic acid (D) 4.84 (2, dd; 9.9 and 3.2), 1.38 (3, m), 1.68–1.75 (3, m), 1.68–1.75 (4, m), 0.86 (4-Me, d; 6.7), 0.87 (5, d; 6.7). $^{13}$C NMR (CDCl$_3$) unit δ (carbon position) A 165.4 (1), 125.4 (2), 140.9 (3), 36.7 (4), 76.3 (5), 40.6 (6), 13.5 (6-Me), 63.0 (7), 58.9 (8), 136.7 (9), 125.6 (10/14), 128.7 (11/13), 128.6 (12); B 170.7 (1), 53.3 (2), 35.0 (3), 130.3 (4), 129.0 (5/9), 121.0 (6/8), 146.7 (7); C 175.3 (1), 38.4 (2), 13.9 (2-Me), 41.5 (3); D 170.8 (1), 71.3 (2), 39.4 (3), 24.6 (4), 21.3 (4-Me), 22.9 (5).

Cryptophycin 24

[α]$_D$ +48.8°(CHCl$_3$, c 0.63); UV λ$_{max}$ (ε) 228 (19006), 242 (8249), 274 (2351); IR (neat) ν$_{max}$ 3400, 3284, 2959, 1732, 1678, 1652, 1514, 1248, 1178 cm$^{-1}$; EIMS m/z (rel intensity, assignment) 606 (2, M$^+$), 364 (7), 161 (55, CH$_3$O—C$_6$H$_4$—CH=CH=CO$^+$), 121 (100, CH$_3$O—C$_6$H$_4$—CH$_2^+$), 91 (68); high resolution EIMS m/z 606.2954 (calcd for C$_{34}$H$_{42}$N$_2$O$_8$, −1.3 mmu error); $^1$H NMR (CDCl$_3$) amino or hydroxy acid unit δ (carbon position, multiplicity; J in Hz) 7,8-epoxy-5-hydroxy-6-methyl-8-phenyl-2-octenoic acid (A) 5.70 (2, dd; 15.2 and 1.3), 6.70 (3, ddd; 15.2, 10.3 and 4.7), 2.43 (4, dt; 14.3 and 10.9), 2.56 (4, m), 5.20 (5, ddd; 11.3, 5.1 and 2.0), 1.79 (6, m), 1.14 (6-Me, d; 7.0), 2.92 (7, dd; 7.5 and 2.0), 3.68 (8, d; 2.0), 7.23–7.38 (10/11/12/13/14, m); O-methyltyrosine (B) 4.73 (2, m), 5.58 (2-NH, d; 8.3), 3.03 (3, dd; 14.5 and 7.5), 3.14 (3, dd; 14.5 and 5.7), 7.11 (5/9, d; 8.6), 6.81 (6/8, d; 8.6), 3.78 (7-OMe, s); 3-aminopropionic acid (C) 2.55 (2-H$_2$, m), 3.42 (3, m), 3.53(3, m), 6.97 (3-NH, br t; 5.7); leucic acid (D) 4.89 (2, dd; 9.9 and 3.5), 1.29 (3, m), 1.62–1.70 (3/4, m), 0.83 (5, d; 5.9), 0.84 (5', d; 6.1); $^{13}$CNMR(CDCl$_3$): unit δ (carbonposition) A 165.4(1), 125.3 (2), 141.0(3), 36.7 (4), 75.9 (5), 40.6 (6), 13.4 (6-Me), 63.0 (7), 59.0 (8), 136.7 (9), 125.6 (10/14), 128.7 (11/13), 128.5 (12); B 170.7 or 170.6 (1), 54.1 (2), 35.2 (3), 128.5 (4), 130.2 (5/9), 114.1 (6/8), 158.6 (7), 55.2 (7-OMe); C 172.8 (1), 32.5 (2), 34.2 (3); D 170.6 or 170.7 (1), 71.2 (2), 39.5 (3), 24.4 (4), 21.3 (5), 22.8 (5').

Cryptophycin 26

[α]$_D$ +28.2°(CHCl$_3$, c 1.31); UV λ$_{max}$(ε) 254 (14615), 284 (2949); IR (neat) ν$_{max}$ 3299, 2960, 1732, 1644, 1504, 1258, 1209 cm$^{-1}$; EIMS m/z (rel intensity) 656/658 (0.5⁄0.1, M$^+$), 638/640 (1.7/1.0), 525/527 (3.7/1.8), 412/414 (10/4), 280/282 (12/11), 227 (20), 195 (48), 131 (68); high resolution EIMS m/z 656.2836 (calcd for C$_{35}$H$_{45}$ClN$_2$O$_8$, 2.8 mmu error), 638.2712 (calcd for C$_{35}$H$_{43}$ClN$_2$O$_7$, 4.7 mmu error); $^1$H NMR (CDCl$_3$) amino or hydroxy acid unit δ (carbon position, multiplicity; J in Hz) 3,5-dihydroxy-6-methyl-8-phenyl-7-octenoic acid (A) 2.46 (2, dd; 14.8 and 7.8), 2.58 (2, dd; 14.8 and 3.0), 5.46 (3, m), 1.86–1.90 (4-H$_2$, m), 3.61 (5, m), 2.37 (6, m), 1.14 (6-Me, d; 6.8), 6.06 (7, dd; 16 and 8.7), 6.47 (8, d; 16), 7.37 (10/14, br d; 7.9), 7.32 (11/13, br t; 7.6), 7.22–7.28 (12, m); 3-chloro-4methoxyphenylalanine (B) 4.73 (2, br dt; 6.4 and 8.1), 6.14 (2-NH, d; 8.6), 2.84 (3, dd; 14.4 and 8), 3.18 (3, dd; 14.4 and 6.3), 7.21 (5, d; 2.2), 3.85 (7-OMe, s), 6.82 (8, d; 8.6), 7.08 (9, dd; 8.6 and 2.2); 3-amino-2-methylpropionic acid (C) 2.87 (2, m), 1.19 (2-Me, d; 7.0), 3.01 (3, ddd; 13.4, 10.6 and 4.9), 3.73 (3, ddd; 13.4, 8.2 and 4.7), 6.72 (3-NH, br dd; 7.3 and 5.2); leucic acid () 4.95 (2, dd; 9.7 and 4.2), 1.62–1.72 (3, m), 1.79–1.84 (3, m), 1.62–1.72 (4, m), 0.90 (4-Me, d; 6.4), 0.95 (5, d; 6.4). $^{13}$C NMR (CDCl$_3$) unit δ (carbon position) A 170.0 (1), 41.5 (2), 71.4 (3), 37.3 (4), 71.9 or 71.8 (5), 43.6 (6), 16.6 (6-Me), 130.8 (7), 132.5 (8), 136.8 (9), 126.2 (10/14), 128.6 (11/13), 127.6 (12); B 170.9 (1), 53.2 (2), 34.7 (3), 130.3 (4), 131.1 (5), 122.2 (6), 153.8 (7), 56.1 (7-OMe), 112.2 (8), 128.5 (9); C 174.3 (1), 40.1 (2), 14.4 (2-Me), 42.5 (3); D 170.7 (1), 71.8 or 71.9 (2), 38.9 (3), 24.6 (4), 21.6 (4-Me), 22.9 (5).

Cryptophycin 28

[α]$_D$ +65.6°(MeOH, c 0.93); UV (MeOH) λ$_{max}$ (ε) 204 (48000), 230 (19300), 248 (18700), 280 (3400); IR (neat) ν$_{max}$ 3413, 3270, 2958, 1745, 1726, 1665, 1504, 1258, 1197, 1175, 1066, 694 cm$^{-1}$; EIMS m/z (rel intensity) 624/626 (3.0/1.3), 412/414 (70/24), 280/282(13/6), 213 (100), 195/197 (86/40); high resolution EIMS m/z 624.2626 (calcd for C$_{34}$H$_{41}$ClN$_2$O$_7$, −2.4 mmu error); $^1$H NMR(CDCl$_3$) amino or hydroxy acid unit δ (carbon position, multiplicity; J in Hz) 5-hydroxy-8-phenyl-2,7-octadienoic acid (A) 5.78 (2, d; 15.6), 6.71(3, ddd; 15.6, 9.9 and 5.4), 2.40 (4, m), 2.53 (4, m), 5.17 (5, m), 2.53 (6-H$_2$, br t; 6.7), 6.07 (7, dt; 15.8 and 7.4), 6.44 (8, d; 15.8), 7.27–7.38 (10/11/13/14, m), 7.22 (12, m); 3-chloro-4-methoxyphenylalanine (B) 4.82 (2, m), 5.72 (2-NH, d; 8.5), 3.04 (3, dd; 14.5 and 7.2), 3.14 (3, dd; 14.5 and 5.4), 7.22 (5, d; 2.0), 3.87 (7-OMe, s), 6.84 (8, d; 8.5), 7.08 (9, dd; 8.5 and 2.0); 3-amino-2-methylpropionic acid (C) 2.72 (2, m), 1.21 (2-Me, d; 7.2), 3.29 (3, dt; 13.5 and 7.0), 3.49 (3, ddd; 13.5, 4.9 and 3.8), 6.97 (3-NH, br t; 5.6); leucic acid (D) 4.82 (2, m), 1.40 (3, m), 1.62 (3, m), 1.62 (4, m), 0.76 (4-Me, d; 6.3), 0.74 (5, d; 6.3); $^{13}$C NMR (CDCl$_3$) unit δ (carbon position) A 165.4 (1), 125.2 (2), 141.2 (3), 38.5 (4), 73.5 (5), 38.6 (6), 124.1 (7), 133.8 (8), 136.7 (9), 126.1 (10/14), 128.6 (11/13), 127.6 (12); B 170.9 (1), 53.6 (2), 35.1 (3), 129.8 (4), 131.0 (5), 122.4 (6), 154.0 (7), 56.1 (7-OMe), 112.3 (8), 128.4 (9); C 175.6 (1), 38.3 (2), 14.0 (2-Me), 41.2 (3); D 170.9 (1), 71.6 (2), 39.6 (3), 24.5 (4), 21.5 (4-Me), 22.6 (5).

Cryptophycin 29

[α]$_D$ +22.2°(CHCl$_3$, c 1.13); UV λ$_{max}$(ε) 250 (17000), 284 (3300); IR (neat) ν$_{max}$ 3415, 3272, 2960, 1744, 1734, 1674, 1504, 1259, 1197, 1174, 1067, 694 cm$^{-1}$; EIMS m/z (rel intensity) 624/626 (2.6/1.1), 398/400 (44/15), 227 (100), 195/197 (50/16), 155/157 (59/20), 131 (63), 91 (95); high resolution EIMS m/z 624.2607(calcd for C$_{34}$H$_{41}$ClN$_2$O$_7$, −0.5 mmu error); $^1$H NMR(CDCl$_3$) amino or hydroxy acid unit δ (carbon position, multiplicity; J in Hz) 5-hydroxy-6-methyl-8-phenyl-2,7-octadienoic acid (A) 5.75 (2, dd; 15.3 and 1.1), 6.69 (3, ddd; 15.3, 10.1 and 5.3), 2.36 (4, m), 2.54 (4, m), 5.03 (5, ddd; 11.0, 6.4 and 1.8), 2.56 (6, m), 1.14 (6-Me, d; 6.8), 6.01 (7, dd; 15.8 and 8.8), 6.41 (8, d; 15.8), 7.28–7.33 (10/11/13/14, m), 7.22 (12, m); 3-chloro-4-methoxyphelylalanine (B) 4.76 (2, m), 5.67 (2-NH, d; 8.6), 3.0 (3, dd; 14.4 and 10.2), 3.14 (3, dd; 14.4 and 5.9), 7.22 (5, d; 2.2), 3.87 (7-OMe, s), 6.83 (8, d; 8.4), 7.08 (9, dd; 8.4 and 2.2); 3-aminopropionic acid (C) 2.55 (2-H$_2$, m), 3.44 (3, m), 3.55 (3, m), 6.89 (3-NH, br t; 5.7); leucic acid (D) 4.90 (2, dd; 9.9 and 3.5), 1.34 (3, ddd; 15.4, 10.3 and 3.5), 1.63 (3, m), 1.63 (4, m). 0.76 (4-Me, d; 6.4), 0.72 (5, d; 6.4); $^{13}$C NMR (CDCl$_3$) unit δ (carbon position) A 165.6 (1), 125.2 (2), 141.5 (3), 36.4 (4), 77.1 (5), 42.3 (6), 17.3 (6-Me), 130.1 (7), 131.8 (8), 136.7 (9), 126.2 (10/14), 128.6 (11/13), 127.6 (12); B 170.9 (1), 53.8 (2), 34.9 (3), 129.9 (4), 131.0 (5), 122.4 (6), 153.9 (7), 56.1 (7-OMe), 112.2 (8), 128.4 (9); C 172.6 (1), 32.4 (2), 34.5 (3); D 170.4 (1), 71.5 (2), 39.7 (3), 24.4 (4), 21.2 (4-Me), 22.6 (5).

Cryptophycin 30

[α]$_D$ −12.3°(CHCl$_3$, c 1.53); UV λ$_{max}$(ε) 254 (17200), 284 (3600); IR (neat) ν$_{max}$ 3414, 3306, 2961, 1738, 1729, 1660, 1504, 1258, 1205, 1183, 1066, 695 cm$^{-1}$; EIMS m/z (rel intensity) 656/658 (1.0/0.3), 638/640 (3.0/1.0), 525/527 (3.8/1.3), 412/414 (10.5/3.6), 280/282(10.3/3.8), 227 (29), 195/197 (48/17), 155/157 (74/21), 131 (100); high resolution EIMS m/z 656.2852(calcd for C$_{35}$H$_{45}$ClN$_2$O$_8$, 1.3 mmu error); $^1$H-NMR(CDCl$_3$):amino or hydroxy acid unit δ (carbon position, multiplicity; J in Hz) 3,5-dihydroxy-6-methyl-8-phenyl-7-octenoic acid (A) 2.25 (2, dd; 16.0 and 9.6), 2.64 (2, brd; 16.0), 3.89 (3, m), 2.51 (3-OH, d; 6.4), 1.77 (4, ddd; 14.3, 9.8 and 2.1), 1.88 (4, ddd; 14.3, 11.3 and 3.8), 4.88 (5, ddd; 11.3, 6.2 and 2.1), 2.53 (6, m), 1.10 (6-Me, d; 6.8), 5.99 (7, dd; 15.9 and 9.0), 6.40 (8, d; 15.9), 7.28–7.33 (10/11/13/14, m), 7.23 (12, m); 3-chloro-4-methoxyphenylalanine (B) 4.60 (2, m), 6.61 (2-NH, d; 8.1), 3.09 (3, dd; 14.2 and 5.6), 3.15 (3, dd; 14.2 and 7.3), 7.22 (5, d; 2.1), 3.86 (7-OMe, s), 6.83 (8, d; 8.3), 7.07 (9, dd; 8.3 and 2.1); 3-amino-2-methylpropionic acid (C) 2.67 (2, m), 1.21 (2-Me, d; 7.3), 3.26 (3, ddd; 13.6, 7.3 and 6.4), 3.63 (3, ddd; 13.6, 6.2 and 3.9), 6.75 (3-NH, brt; 6.3); leucic acid (D) 4.83 (2, dd; 9.6, 4.1), 1.42 (3, m), 1.64 (3, m), 1.64 (4, m). 0.79 (4-Me, d; 6.4), 0.76 (5, d; 6.4); $^{13}$C NMR (CDCl$_3$) unit δ (carbon position) A 171.6 (1), 42.4 (2), 66.0 (3), 41.3 (4), 76.0 (5), 42.0 (6), 17.3 (6-Me), 130.0 (7), 131.9 (8), 136.7 (9), 126.1 (10/14), 128.6 (11/13), 127.6 (12); B 170.8 (1), 54.3 (2), 35.1 (3), 130.1 (4), 131.1 (5), 122.2 (6), 153.8 (7), 56.1 (7-OMe), 112.1 (8), 128.7 (9); C 175.6 (1), 39.7 (2), 13.8 (2-Me), 41.5 (3), D 171.9 (1), 72.1 (2), 39.1 (3), 24.6 (4), 21.4 (4-Me), 22.7 (5).

Cryptophycin 31

$[\alpha]_D$ +50.6°(MeOH, c 1.13); UV $\lambda_{max}$(ε) 242 (3800), 284 (700); IR (neat) $\nu_{max}$ 3412, 3272, 2961, 1745, 1725, 1678, 1537, 1481, 1270, 1196, 1176, 1000, 698 cm$^{-1}$; EIMS m/z (rel intensity) 688/690/692 (1.2/1.0/0.4), 446/448/450 (7.9/6.7/3.1), 314/316/318 (17/11/3), 91 (100); high resolution EIMS m/z 688.2336 (calcd for C$_{35}$H$_{42}$Cl$_2$N$_2$O$_8$, −1.8 mmu error); $^1$H-NMR (CDCl$_3$)amino or hydroxy acid unit δ (carbon position, multiplicity; J in Hz) 7,8-epoxy-5-hydroxy-6-methyl-8-phenyl-2-octenoic acid (A) 5.78 (2, d; 15.5), 6.66 (3, ddd; 15.5, 9.4 and 6.0), 2.47 (4, ddd; 14.1, 10.8 and 9.4), 2.56 (4, m), 5.14 (5, ddd; 10.8, 4.7 and 1.7), 1.82 (6, m), 1.15 (6-Me, d; 7.1), 2.93 (7, dd; 7.5 and 1.9), 3.70 (8, d; 1.9), 7.24–7.26 (10/14, m), 7.34–7.39 (11/12/13, m); 3,5-dichloro-4-methoxyphenylalanine (B) 4.83 (2, m), 5.68 (2-NH, d; 9.0), 3.0 (3, dd; 14.4 and 7.3), 3.14 (3, dd; 14.4 and 5.6), 7.16 (5/9, s), 3.87 (7-OMe, s); 3-amino-2-methylpropionic acid (C) 2.74 (2, m), 1.22 (2-Me, d; 7.1), 3.20 (3, m), 3.58 (3, ddd; 13.5, 5.6 and 4.1), 6.82 (3-NH, br t; 5.6); leucic acid (D) 4.83 (2, m), 1.38 (3, m), 1.72 (3, m), 1.72 (4, m). 0.87 (4-Me, d; 6.8), 0.86 (5, d; 6.8); $^{13}$C NMR (CDCl$_3$) unit δ (carbon position) A 165.4 (1), 125.4 (2), 141.0 (3), 36.7 (4), 76.3 (5), 40.6 (6), 13.5 (6-Me), 63.0 (7), 58.9 (8), 136.7 (9), 125.6 (10/14), 128.7 (11/13), 128.6 (12); B 170.8 (1), 53.2 (2), 35.2 (3), 129.3 (4), 129.6 (5/9), 134.5 (6/8), 151.2 (7), 60.6 (7-OMe); C 175.3 (1), 38.3 (2), 13.9 (2-CH3), 41.5 (3), D 170.6 (1), 71.3 (2), 39.4 (3), 24.6 (4), 22.9 (4-Me), 21.3 (5).

Cryptophycin 40

$[\alpha]_D$+41.6°(CHCl$_3$, c 0.31); UV $\lambda_{max}$(ε) 242 (4974), 266 (3911), 274 (3666), 286 (2359), 328 (511); IR (neat) $\nu_{max}$3415, 2959, 1748, 1723, 1667, 1505, 1463, 1289, 1176 cm$^{-1}$; EIMS m/z (rel intensity) 640/642 (5/2), 280/282 (7/3), 213 (13), 195/197 (51/17), 155 (29), 141 (32), 121 (28), 91 (100), 69 (47); high resolution EIMS m/z 640.2570 (calcd. for C$_{34}$H$_{41}$ClN$_2$O$_8$, −1.8 mmu error); $^1$H NMR (CDCl$_3$) amino or hydroxy acid unit δ (carbon positions, multiplicities; J in Hz) 7,8-epoxy-5-hydroxy-8-phenyl-2-octenoic acid (A) 5.77 (2, d; 15.1), 6.72 (3, ddd; 15.1, 9.7 and 4.9), 2.42 (4, m), 2.58 (4, m), 5.33 (5, m), 1.89 (6, ddd; 12.9, 8.1 and 5.0), 2.13 (6, ddd; 12.9, 9.3 and 5.0), 2.98 (7, ddd; 6.7, 4.5 and 1.9), 3.64 (8, d; 1.9), 7.31–7.39 (10/11/13/14, m), 7.22 (12, m); 3-chloro-4-methoxyphenylalanine (B) 4.83 (2, m), 5.64 (2-NH, d; 8.6), 3.03 (3, dd; 14.3 and 7.5), 3.14 (3, dd; 14.3 and 5.4), 7.21 (5, d; 2.0), 3.87 (7-OMe, s), 6.84 (8, d; 8.3), 7.08 (9, dd; 8.3 and 2.0); 3-amino-2-methylpropionic acid (C) 2.72 (2, m), 1.23 (2-Me, d; 7.3), 3.31 (3, dt; 13.8 and 6.9), 3.50 (3, ddd; 13.6, 5.7 and 3.9), 6.96 (3-NH, br t; 6.0); leucic acid (D) 4.85 (2, dd; 6.7, 3.4), 1.42 (3, m), 1.72 (3, m), 1.72 (4, m), 0.86 (4-Me, d, 3.7), 0.87 (5, d, 3.7); $^{13}$C NMR (CDCl$_3$) unit δ (carbon position) A 165.3 (1), 125.2 (2), 140.9 (3), 39.0 (4), 72.0 (5), 37.3 (6), 59.0 (7), 58.7 (8), 140.9 (9), 125.6 (10/14), 128.7 (11/13), 128.5 (12); B 170.9 (1), 53.6 (2), 35.1(3), 129.8 (4), 131.0 (5), 122.5 (6), 157.0 (7), 56.1 (7-OMe), 112.3 (8), 128.4 (9); C 175.6 (1), 38.3 (2), 14.1 (2-Me), 41.1 (3); D 170.9 (1), 71.4 (2), 39.4 (3), 24.5 (4), 21.5 (4-Me), 22.8 (5).

Cryptophycin 43

$[\alpha]_D$+20°(CHCl$_3$, c 0.2); UV $\lambda_{max}$(ε) 250 (20512), 282 (4083), 294 (1734); IR (neat) $\nu_{max}$ 3400, 3272, 2927, 1727, 1660, 1516, 1455, 1242, 1175 cm$^{-1}$; EIMS m/z (rel intensity) 533 (24), 484 (3), 445 (14), 398 (9), 364 (29), 227 (59), 149 (67), 91 (100); high resolution EIMS m/z 590.3044 (calcd for C$_{34}$H$_{41}$N$_2$O$_7$, −5.2 mmu error); $^1$H NMR (CDCl$_3$) amino or hydroxy acid unit δ (carbon position, multiplicity; J in Hz) 5-hydroxy-6-methyl-8-phenyl-2,7-octadienoic acid (A) 5.75 (2, d; 15.3), 6.69 (3, ddd; 15.3, 9.9 and 5.3), 2.37 (4, dt; 14.2 and 10.4), 2.52 (4, m), 5.01 (5, ddd; 11.2, 6.4 and 1.8), 2.55 (6, m), 1.13 (6-Me, d; 6.9), 6.01 (7, dd; 15.8 and 8.9), 6.41 (8, d; 15.8), 7.21–7.34 (10/11/12/13/14, m); 4methoxyphenylalanine (B) 4.80 (2, m), 5.64 (2-NH, d; 8.4), 3.06(3, dd; 14.5 and 7.2), 3.13 (3, dd; 14.4 and 5.3), 7.06 (5/9, d; 8.4), 6.74 (6/8, d; 8.4); 3-amino-2-methylpropionic acid (C) 2.69 (2, m), 1.22 (2-Me, d; 7.3), 3.33 (3, m), 3.44 (3, dt; 14.0 and 4.7), 7.0 (3-NH, m); leucic acid (D) 4.84 (2, dd; 10.0 and 3.6), 1.60–1.67 (3, m), 1.35 (3, m), 1.60–1.67 (4, m), 0.76 (5, d; 6.4), 0.73 (5', d; 6.7); $^{13}$C NMR (CDCl$_3$) unit δ (carbon position) A 125.2 (2), 141.5 (3), 36.5 (4), 77.5 (5), 42.3 (6), 17.3 (6-Me), 130.1 (7), 131.8 (8), 136.8 (9), 126.2 (10/14), 128.6 (11/13), 127.6 (12); B 53.8 (2), 35.3 (3), 129.8 (4), 130.5 (5/9), 115.6 (6/8), 154.6 (7); C 38.3 (2), 14.1 (2-Me), 41.0 (3); D 71.6 (2), 39.6 (3), 24.5 (4), 21.2 (5), 22.9 (5'). Due to the small sample size, carbonyl carbon signals could not be seen.

Cryptophycin 45

$[\alpha]_D$ +72.0°(MeOH, c 0.122); UV $\lambda_{max}$(ε) 250 (25500), 284 (5300); IR (neat) $\nu_{max}$ 3407, 3239, 2958, 1743, 1727, 1667, 1538, 1469, 1242, 1196, 1177, 694 cm$^{-1}$; EIMS m/z (rel intensity) 658/660/662 (2.1/1.4/0.3), 483 (7.6) 432/434/436 (9.5/6.4/1.8), 300/302/304 (8.0/5.5/1.2), 227 (100) 91 (87); high resolution EIMS m/z 658.2207 (calcd for C$_{34}$H$_{40}$Cl$_2$N$_2$O$_7$, 0.6 mmu error); $^1$H-NMR(CDCl$_3$):amino or hydroxy acid unit δ (carbon position, multiplicity; J in Hz) 5-hydroxy-6-methyl-8-phenyl-2,7-octadienoic acid (A) 5.80 (2, d; 14.7), 6.66 (3, ddd; 14.7, 8.5 and 5.5), 2.38 (4, m), 2.53 (4, m), 4.97 (5, br dd; 10.4 and 6.2), 2.57 (6, m), 1.14 (6-Me, d; 6.7), 6.01 (7, dd; 15.9 and 8.7), 6.42 (8, d; 15.9), 7.28–7.34 (10/11/1314, m), 7.22 (12; m); 3,5-dichloro-4hydroxyphenylalanine (B) 4.82 (2, m), 5.73 (2-NH, br d; 8.7), 3.02 (3, dd; 14.3 and 6.2), 3.10 (3, dd; 14.3 and 5.2), 7.14 (5/9, s), 5.79 (7-OH, s); 3-amino-2-methylpropionic acid (C) 2.73 (2, m), 1.21 (2-Me, d; 7.0), 3.17 (3, m), 3.60 (3, m), 6.81 (3-NH, br t; 6.7); leucic acid (D) 4.84 (2, dd;10.0 and 3.2), 1.38 (3, ddd; 14.9, 10.2 and 3.2), 1.65 (3, m), 1.65 (4, m). 0.78 (4-Me, d; 6.5), 0.73 (5, d; 6.5); $^{13}$C NMR (CDCl$_3$) unit δ (carbon position) A 165.5 (1), 125.4 (2), 141.2 (3), 36.4 (4), 77.6 (5), 42.3 (6), 17.3 (6-Me), 130.0 (7), 131.9 (8), 136.7 (9), 126.2 (10/14), 128.6 (11/13), 127.6 (12); B 171.0 (1), 53.2 (2), 35.0 (3), 130.4 (4), 129.1 (5/9), 121.0 (6/8), 146.7 (7); C 175.2 (1), 38.5 (2), 13.9 (2-Me), 41.6 (3), D 170.7 (1), 71.5 (2), 39.5 (3), 24.6 (4), 22.7 (4-Me), 21.2 (5).

Cryptophycin 49

$[\alpha]_D$ +68.1°(MeOH, c 0.075); UV $\lambda_{max}$(ε) 246 (25500), 284 (5200); IR (neat) $\nu_{max}$ 3401, 3282, 2962, 1744, 1728, 1668, 1540, 1505, 1464, 1258, 1198, 1177, 1066, 694 cm$^{-1}$;EIMS m/z (rel intensity) 624/626 (0.8/0.3), 398/400 (43/14), 227(78), 195/197 (58/26) 91 (100); high resolution EIMS m/z 624.2650 (calcd for C$_{34}$H$_{41}$ClN$_2$O$_7$, −4.8 mmu error); $^1$H-NMR(CDCl$_3$): amino or hydroxy acid unit δ (carbon position, multiplicity; J in Hz) 5-hydroxy-6-methyl-8-phenyl-2,7-octadienoic acid (A) 5.77 (2, d; 14.1), 6.67 (3, m), 2.38 (4, m), 2.50 (4, m), 5.01 (5, m), 2.56 (6, m), 1.13 (6-Me, d; 6.5), 6.03 (7, dd; 15.8 and 8.6), 6.42 (8, d; 15.8), 7.29–7.35 (10/11/13/14, m), 7.23 (12; m); 3-chloro-4-methoxyphenylalanine (B) 4.82 (2, m), 5.64 (2-NH, m), 3.06 (3, m), 3.13 (3, m), 7.22 (5, m), 3.87 (7-OMe, s), 6.83 (8, m), 7.08 (9, m); 3-amino-2-methylpropionic acid (C) 2.72 (2, m), 1.22 (2-Me, d; 6.7), 3.26 (3, m), 3.53 (3, m), 6.90 (3-NH, m); 2-hydroxyvaleric acid (D) 4.81 (2, dd; 8.8 and 3.9), 1.63 (3, m), 1.68 (3, m), 1.33 (4-$H_2$, m). 0.74 (5, t; 7.3).

Cryptophycin 50

$[\alpha]_D$ +32.0°(CHCl$_3$ c. 0.44); UV $\lambda_{max}(\epsilon)$ 242 (4933), 262 (3996, 274 (3719), 286 (2430), 332 (359); IR (neat) $v_{max}$3412, 3274, 2958, 1752, 1724, 1676, 1648, 1503, 1465, 1258, 1177, 1066, 753; EIMS m/z (rel intensity) 640/642 (4/2), 398/400 (11/4), 280/282 (10/3), 227 (17), 195/197 (57/18), 157 (20), 141 (31), 91 (100); high resolution EIMS m/z 640.2531 (calcd. for $C_{34}H_{41}ClN_2O_8$, 2.1 mmu error); $^1$H NMR (CDCl$_3$) amino or hydroxy acid unit δ (carbon positions, multiplicities; J in Hz) 7,8-epoxy-5-hydroxy-6-methyl-8-phenyl octanoic acid (A) 5.73 (2, d; 15.7), 6.67 (3, ddd; 15.7, 9.7 and 5.4), 2.45 (4, m), 2.55 (4, m), 5.13 (5, ddd; 11.2, 5.0 and 1.7), 1.78 (6, m), 1.15 (6-Me, d, 6.9), 2.91 (7, dd; 7.5 and 1.9), 3.68 (8, d; 1.7), 7.25 (10/14, m), 7.33–7.38 (11/12/13; m); 3-chloro-4-methoxyphenylalanine (B) 4.80 (2, ddd; 8.3, 7.1 and 5.4), 5.61 (2-NH, d; 8.3), 3.03 (3, dd; 14.4 and 7.3), 3.13 (3, dd; 14.4 and 5.6), 7.21 (5, d; 1.9), 3.87 (7-OMe, s), 6.83 (8, d; 8.4), 7.07 (9, dd; 8.4 and 2.2); 3-amino-2-methylpropionic acid (C) 2.71 (2, m), 1.22 (2-Me, d; 7.3), 3.29 (3, dt; 13.6 and 6.9), 3.49 (3, ddd; 13.6, 6.7 and 5.0), 6.92 (3-NH, br t; 6.7); 2-hydroxypenanoic acid (D) 4.75 (2, dd; 9.2 and 3.7), 1.55 (3, m), 1.65 (3, m), 1.33 (4-$H_2$, m), 0.84 (5, t; 7.3); $^{13}$C NMR (CDCl$_3$) unit δ values (carbon positions) A 165.3 (1), 125.3 (2), 141.0 (3), 36.9 (4), 76.3 (5), 40.8 (6), 13.6 (6-Me), 63.2 (7), 59.1 (8), 136.8 (9), 125.5 (10/14), 128.7 (11/13), 128.5 (12); B 170.9 (1), 53.6 (2), 35.1 (3), 129.8 (4), 131.0 (5), 122.5 (6), 154.0 (7), 56.1 (7-OMe), 112.3 (8), 128.5 (9); C 175.6 (1), 38.4 (2), 14.1 (2-Me), 41.2 (3); D 170.4 (1), 72.4 (2), 32.7 (3), 18.4 (4), 13.5 (5).

Cryptophycin 54

EIMS m/z (relative intensity) 654/656 (17/10), 493 (5), 411/413 (12/4), 280 (16), 227 (25), 195/197 (45/25), 141 (30), 91 (100); high resolution EIMS m/z 654.2686 (calcd for $C_{35}H_{43}ClN_2O_8$, 2.2 mmu error); $^1$H NMR (CDCl$_3$): amino or hydroxy acid unit δ (carbon position, multiplicity; J in Hz) 5-hydroxy-6-methyl-7-oxo-8-phenyl-2-octenoic acid (A) 5.73 (2, d; 15.4), 6.66 (3, ddd; 15.4, 9.7, 5.7), 2.46 (4, m), 2.53 (4, m), 5.16 (5, ddd; 11.0, 4.2, 1.7), 1.79 (6, m), 1.14 (6-Me, d; 6.8), 2.89 (7, dd; 7.4, 1.8), 3.69 (8, d; 1.9), 7.25 (10/14, m), 7.30–7.38 (11/12/13, m); (B) 4.81(2, m), 5.63 (2-NH, d; 8.6), 3.03 (3, dd; 14.5, 7.3), 3.13 (3, dd; 14.5, 5.5), 7.21 (5, d; 2.2), 3.87 (7-OMe, s), 6.83 (8, d; 8.4), 7.07 (9, dd; 8.4, 2.2); (C) 2.73 (2, m), 1.22 (2-Me, d; 7.3), 3.26 (3, ddd; 13.4, 6.8, 6.8), 3.51 (3, ddd; 13.4, 6.8, 5.3), 6.88 (3-NH, br t; 6.8); (D) 4.73 (2, d; 4.2), 1.78–1.82 (3, m), 0.92 (3-Me, d; 6.8), 1.36–1.41 (4, m), 1.18–1.20 (4, m), 0.80 (5, t; 7.5); $^{13}$C NMR (CDCl$_3$): unit δ (carbon position) A 165.3 (1), 125.4 (2), 141.0 (3), 36.6 (4), 76.3 (5), 40.6 (6), 13.2 (6-Me), 63.1 (7), 58.7 (8), 136.7 (9), 125.4 (10/14), 128.6 (11/13), 128.5 (12); B 170.9 (1), 53.5 (2), 35.0 (3), 129.8 (4), 131.0 (5), 125.2 (6), 153.9 (7), 56.1 (7-OMe), 112.2 (8), 128.4 (9); C 175.4 (1), 38.5 (2), 14.0 (2-Me), 41.3 (3); D 169.4 (1), 76.5 (2), 36.1 (3), 15.6 (3-Me), 24.0 (4), 11.2 (5).

EXAMPLE 6

Synthesis of Cryptophycin Derivatives

Crypotophycin 8

To a solution of 3.8 mg of Cryptophycin 1 in 1.5 mL of 2:1 1,2-dimethoxyethane/water was added 9 µL 1N HCl. The solution was allowed to stir at room temperature for 4 h, neutralized with potassium carbonate, and evaporated. The residue was partitioned between water and $CH_2Cl_2$. The $CH_2Cl_2$-soluble material was purified by reversed-phase HPLC to obtain 3.3 mg of pure Cryptophycin 8.

EIMS m/z (relative intensity) 690/692/694 (0.8/0.5/0.2). High resolution EIMS m/z 690.2533 (calcd for $C_{35}H_{44}Cl_2N_2O_8$, –5.8 mmu error). $^1$H NMR (CDCl$_3$): amino or hydroxy acid unit δ (carbon position, multiplicity; J in Hz) 8-chloro-5,7-dihydroxy-6-methyl-8-phenyl-2-octenoic acid (A) 5.79 (2, d; 15.4), 6.69 (3, ddd; 15.4, 9.7 and 5.6), 2.68 (4, ddt; 14.0, 5.5 and 1.8), 2.38 (4,m), 5.11 (5, ddd; 10.8, 8.6 and 1.8), 2.51 (6, m), 1.05 (6-Me, d; 7.0), 4.01 (7, dd; 9.6 and 1.9), 4.65 (8, d; 9.6), 7.36–7.41 (10/11/12/13/14, m); leucic acid (D) 4.92 (2, dd; 10.1 and 3.5), 1.76 (3/4, m), 1.45 (3, m), 0.94 (5, d; 6.6), 0.94 (5', d; 6.4); 3-amino-2-methylpropionic acid (C) 2.73(2, m), 1.22 (2-Me, d; 7.2), 3.25 (3, ddd; 13.6, 6.8 and 6.1), 3.54 (3, ddd; 13.5, 6.1 and 3.4), 6.91(3-NH, brt; 6. 1); 3-chloro-4-methoxyphenylalanine (B) 4.82 (2, ddd; 8.8, 7.2 and 5.6), 5.64 (2-NH, d; 8.8), 3.03 (3, dd; 15.4 and 7.2), 3.16 (3, dd; 15.4 and 5.6), 7.23 (5, d; 2.2), 3.88 (7-OCH$_3$, s), 6.85 (8, d; 8.5), 7.09 (9, dd; 8.5 and 2.2).

Cryptophycin 9

To a solution of 10 mg of Cryptophycin 1 in 1 mL dry methanol was added 10 µL methanolic HCl (obtained by treating 1.25 g thionyl chloride with 25 mL MeOH). After stirring for 4 h the solvent was removed in vacuo and the sample was left under vacuum for 12 h. Reversed-phase HPLC gave 8 mg of pure Cryptophycin 9.

$^1$H NMR (CDCl$_3$): amino or hydroxy acid unit δ (carbon position, multiplicity; J in Hz); 5,7-dihydroxy-8-methoxy-6-methyl-8-phenyl-2-octenoic acid (A) 5.76 (2, d; 15.5), 6.67 (3, ddd; 15.5, 9.5 and 5.6), 2.34 (4, ddd; 14.1, 11.1 and 9.5), 2.62 (4, dddd; 14.1, 5.6, 1.8 and 1.5), 5.09 (5, ddd; 11.1, 7.8 and 1.8), 2.24 (6, dqd; 7.8, 7.0 and 2.2), 1.03 (6-Me, d; 7.0), 3.71 (7, dd; 8.3 and 2.2), 4.03(8, d; 8.3), 3.20 (8-OCH$_3$, s), 7.31–7.40 (10/11/12/13/14, m); leucic acid (D) 4.86 (2, dd; 9.8 and 3.5), 1.71 (3/4, m), 1.41 (3, m), 0.89 (5/5', d; 6.4); 3-amino-2-methylpropionic acid (C) 2.71 (2, ddq; 6.8, 3.9 and 7.2), 1.21 (2-Me, d; 7.2), 3.23 (3, ddd; 13.5, 6.8 and 6.0), 3.52 (3, ddd; 13.5, 6.0 and 3.9), 6.90 (3-NH, brt; 6.0); 3-chloro-4-methoxyphenylalanine (B) 4.82 (2, ddd; 8.8, 7.4 and 5.7), 5.66 (2-NH, d; 8.8), 3.02 (3, dd; 14.4, 7.4), 3.15 (3, dd; 14.4 and 5.5), 7.23 (5, d; 2.2), 3.87 (7-OCH$_3$, s), 6.84 (8, d; 8.5), 7.08 (9, dd; 8.5 and 2.2).

Cryptophycin 10

To a stirred solution of 7 mg of Cryptophycin 9 in 1 mL of acetone and 0.3 mL water was added 8 µL of 2N NaOH. After stirring for 4 h the solution was neutralized to pH 7 with 1N HCl and the solvent was removed under reduced pressure. The residue was subjected to reversed-phase HPLC using 7:3 MeOH/H$_2$O to yield pure Cryptophycin 10 (5 mg).

$^1$H NMR (CD$_3$OD): amino or hydroxy acid unit δ (carbon position, multiplicity; J in Hz); 5,7-dihydroxy-8-methoxy-6-methyl-8-phenyl-2-octenoic acid (A) 5.99 (2, dt; 15.4 and 1.3), 6.82 (3, dt; 15.4 and 7.3), 2.30 (4, m), 2.50 (4, m), 3.66 (5, td; 7.8 and 3.5), 2.05 (6, d pentet; 1.8 and 7.0), 0.96 (6-Me, d; 7.0), 4.04 (7, dd; 8.8 and 2.0), 4.01 (8, d; 8.8), 3.12 (8-OCH$_3$, s), 7.26–7.36 (10/11/12/13/14, m); $^3$-amino-2-methylpropionic acid (C) 2.50 (2, m), 1.02 (2-Me, d; 7.3), 3.16 (3, dd; 13.4 and 6.9), 3.82 (3, dd; 13.4 and 6.6); $^3$-chloro-4-methoxyphenylalanine (B) 4.57 (2, dd; 8.5 and 6.5), 2.82 (3, dd; 13.9 and 8.6), 3.03 (3, dd; 13.9 and 6.5), 7.25 (5, d; 2.2), 3.82 (7-OCH$_3$, s), 6.96 (8, d; 8.6), 7.13 (9, dd; 8.6 and 2.2). $^{13}$C NMR (CD$_3$OD): δ 179.5, 173.4, 168.2, 155.4, 143.7, 141.7, 131.9, 131.7, 129.8, 129.3 (2C), 129.2 (2C), 128.8, 126.2, 123.2, 113.4, 85.9, 74.5, 74.1, 56.8, 56.6, 56.3, 43.3, 41.2, 40.2, 38.8, 38.0, 15.5, 9.9.

Cryptophycin 12

To a solution of 5 mg of Cryptophycins 1, 5 or 8 in 1 mL of 4:1 acetone/water was added 15 µL of 2N NaOH. After stirring at room temperature for 5 h, the reaction mixture was neutralized to pH 7 with 1N HCl and evaporated. The $CH_2Cl_2$-soluble material was passed through a small silica-cartridge with $CH_2Cl_2$, 1:1 EtOAc/$CH_2Cl_2$, and EtOAc. The fraction eluted with EtOAc contained pure Cryptophycin 12.

$^1$H NMR ($CD_3OD$): amino or hydroxy acid unit δ (carbon position, multiplicity; J in Hz); 5,7,8-trihydroxy-6-methyl-8-phenyl-2-octenoic acid (A) 6.07 (A) (2, ddd; 15.5, 1.3 and 1.2), 6.40 (3, dt; 15.5 and 7.3), 2.49 (4, m), 2.60 (4, m), 3.92 (5, ddd; 9.3, 6.7 and 4.5), 1.94 (6, m), 1.07 (6-Me, d; 6.6), 3.61 (7, dd; 8.9 and 7.6), 4.56 (8, d; 7.6), 7.36 (10/14, dd; 7.4 and 1.5), 7.32 (11/13, brt; 7.5), 7.25 (12, m); 3-amino-2-methylpropionic acid (C) 2.54 (2, ddq; 7.0, 6.6 and 7.0), 1.02 (2-Me, d; 7.0), 3.14 (3, dd; 13.5 and 7.0), 3.42 (3, dd; 13.4 and 6.6); 3-chloro-4-methoxyphenylalanine (B) 4.57 (2, dd; 8.4 and 6.7), 2.83 (3, dd; 13.8 and 8.4), 3.02 (3, dd; 13.8 and 6.6), 7.25 (5, d; 2.1), 3.82 (7-$OCH_3$, s), 6.95 (8, d; 8.5), 7.12 (9, dd; 8.5 and 2.1). Methylation of Cryptophycin 12 with diazomethane gave Cryptophycin 6.

Cryptophycin 14

To a solution of 3 mg of Cryptophycin 6 in 1 mL of 3:1 acetone/$H_2O$ was added 5 µL of 2N NaOH. After stirring for 5 h, the reaction mixture was neutralized to pH 7 with 1N HCl and then evaporated to dryness. The residue was subjected to reversed-phase HPLC to give 2.4 mg of Cryptophycin 14.

$^1$H NMR ($CD_3OD$): amino or hydroxy acid unit δ (carbon position, multiplicity; J in Hz); 5-hydroxy-6-methyl-8-phenyl-2,7-octadienoic acid (A) 5.98 (2, d; 15.3), 6.78 (3, dt; 15.3 a-nd 7.5), 2.35 (4, m), 3.64 (5, td; 7.2 and 4.8), 2.47 (6, m), 1. 14 (6-Me, d; 6.9), 6.22 (7, dd; 15.9 and 8.1), 6.39 (8, d, 15.9), 7.24–7.36 (10/11/12/13/14, m); 3-amino-2-methylpropionic acid (c) 2.35 (2, m), 1.02 (2-Me, d; 6.9), 3.18 (3, dd; 13.2 and 6.6), 3.36 (3, dd; 13.2 and 4.5); 3-chloro-4-methoxyphenylalanine (B) 4.58 (2, dd; 8.7 and 6.3), 2.80 (3, dd; 13.8 and 9.0), 3.05 (3, dd; 13.8 and 6.3), 7.25 (5, d; 2.1), 3.82 (7-$OCH_3$, s), 6.95 (8, d; 8.4), 7.13(9, dd; 8.4 and 2.1).

Cryptophycin 35

A catalytic amount of $PtO_2$ was added to a flask containing 0.5 ml of $CH_2Cl_2$. The air in the flask was evacuated, $H_2$ was introduced, and the mixture was stirred at room temperature for 20 min. A solution of 10 mg of Cryptophycin 1 in minimum $CH_2Cl_2$ was added and the mixture was stirred at room temperature for 45 min. The catalyst was removed by filtration through celite/cotton and the solvent was evaporated. Reversed phase HPLC of the residue on a C18 column yielded 6.5 mg of Cryptophycin 35.

EIMS m/z (relative intensity) 656/658 (25/10), 412/414 (25/12), 280/282 (20/10), 195/197 (78/25), 141 (58), 91 (100); high resolution EIMS m/z 656.2864 (calcd for $C_{35}H_{45}ClN_2O_8$, 0.0 mmu error); $^1$H NMR ($CDCl_3$) amino or hydroxy acid unit_δ_values (carbon positions, multiplicities; J in Hz) 2,3-dihydro-7,8-epoxy-5-hydroxy-6-methyl-8-phenyl octanoic acid (A) 2.32 (2, ddd; 14.5, 9.2, 5.8), 2.10 (2, ddd; 14.5, 9.2, 6.2), 1.5–1.8 (3/4 overlapping m), 5.07 (5, ddd; 12.5, 5.6, 2.0), 1.80 (6, m), 1.12 (6-Me, d; 7.0), 2.90 (7, dd; 7.4, 1.8), 3.67 (8, d; 1.8), 7.24 (10/14, m), 7.32–7.38 (11/12/13, m); 3-chloro-4-methoxyphenylalanine (B) 4.71 (2, ddd; 8.7, 6.4, 6.3), 5.62 (2-NH, d; 8.7), 3.08 (2H-3, br d; 6.4), 7.19 (5, d; 2.0), 3.87 (7-OMe, s), 6.83 (8, d; 8.5), 7.07 (9, dd; 8.4, 2.0); 3-amino-2-methylpropionic acid (C) 2.72 (2, m), 1.18 (2-Me, d; 6.9), 3.12 (3, ddd; 11.4, 10.6, 5.6), 3.70 (3, ddd), 6.76 (3-NH, br t, 6.0); leucic acid (D) 4.83 (2, dd; 9.9, 3.8), 1.39 (3, m), 1.70 (3, m), 1.72 (4, m), 0.87 (4-Me, d; 5.3), 0.86 (5, d; 5.3); $^{13}$C NMR ($CDCl_3$) unit δ_values (carbon positions) A 172.4 (1), 36.2 (2), 32.0 (3), 21.1 (4), 76.6 (5), 40.2 (6), 13.6 (6-Me), 63.3 (7), 59.2 (8), 136.8 (9), 125.6 (10/14), 128.7 (11/13), 128.6 (12); B 170.7 (1), 53.7 (2), 35.5 (3), 130.0 (4), 131.1 (5), 122.2 (6), 153.8 (7), 56.1 (7-OMe), 112.1 (8), 128.5 (9); C 175.2 (1), 38.2 (2), 13.6 (2-Me), 42.1 (3); D 171.9 (1), 71.7 (2), 39.6 (3), 24.5 (4), 22.9 (4-Me), 21.4 (5).

Cryptophycin 20

Cryptophycin 1 (4.3 mg) in 1:1 dichloromethane/ethyl ether (1.5 mL) was treated with ferric chloride (3 mg) at room temperature for 3 hours. The reaction mixture was washed with water and the organic layer dried over magnesium sulfate and evaporated. The residue was chromatographed on an Alltech extract-clean silica column (500 mg/2.8 mL) and fractions were collected with dichloromethane and ethyl acetate. The ethyl acetate fraction was evaporated and the residue subjected to HPLC purification on an Econosil silica cartridge (250×4.6 mm, 5µ) with 45:55 ethyl acetate/hexane to produce Cryptophycin 20 (3.5 mg): EIMS m/z (relative intensity) 654/656 (0.8/0.5), 433/435 (1.2/0.7), 411/413 (1.4/0.8), 153 (100); high resolution EIMS m/z 654.2718 ($C_{35}H_{43}ClN_2O_8$, Δ−1.0 mmu). $^1$H NMR ($CDCl_3$) amino or hydroxy acid unit δ (carbon positions, multiplicity; J in Hz) 5-hydroxy-6-methyl-7-oxo-8-phenyl-2-octenoic acid (A) 5.74 (2, d; 15.3), 6.66 (3, ddd; 15.3, 10.0 and 5.3), 2.25 (4, dt; 14.2 and 10.7), 2.53 (4, brdd; 14.3 and 5.2), 5.27 (5, ddd; 11, 8.9 and 1.9), 2.94 (6, m), 1.13 (6-Me, d; 7.1), 3.72 (8, s), 7.17 (10/14, brd; 8.4), 7.31–7.34 (11/13, m), 7.28 (12, m); 3-chloro-4-methoxyphenylalanine (B) 4.8 (2, dt; 5.8 and 7.8), 5.63 (2-NH, d; 8.6), 3.03 (3, dd; 14.4 and 7.3), 3.14 (3, dd; 14.4 and 5.5), 7.21 (5, d; 2.0), 3.87 (7-$OCH_3$, s), 6.84 (8, d; 8.4), 7.08 (9, dd; 8.4 and 2.2); 3-amino-2-methylpropionic acid (C) 2.71 (2, m), 1.22 (2-Me, d; 7.3), 3.30 (3, dt; 13.7 and 6.8), 3.48 (3, dt; 13.7 and 4.4); leucic acid (D) 4.72 (2, dd; 10.3 and 3.2), 1.63–1.71 (3, m), 1.16–1.22 (3, m), 1.63–1.71 (4, m), 0.83 (4-Me, d; 6.4), 0.88 (5, d; 6.4). $^{13}$C NMR ($CDCl_3$): unit δ (carbon position) A 165.3 (1), 125.3 (2), 140.9 (3), 35.8 (4), 74.6 (5), 49.1 (6), 13.6 (6-Me), 207.4 (7), 49.4 (8), 133.2 (9), 128.8 (10/14), 129.5 (11/13), 128.4 (12); B 170.9 (1), 53.6 (2), 35.0 (3), 129.9 (4), 131.0 (5), 122.4 (6), 154.0 (7), 56.2 (7-OCH3), 112.3 (8), 127.3 (9); C 175.7 (1), 38.3 (2), 14.1 (2-Me), 41.1(3); D 170.1(1), 71.3 (2), 39.0 (3), 24.6 (4), 21.3 (4-Me), 23.0 (5).

Cryptophycins 25 and 37

Method I

Cryptophycin 1 (20 mg) was dissolved in 1.5 mL dimethoxyethane in a reaction vial 150 µl 30% hydrogen bromide in acetic acid was added. The reaction mixture was stirred at 100° C. for 48 hours. The contents were then cooled to ambient temperature, neutralized to pH 7 with 1M potassium carbonate and partitioned between water and ethyl acetate. The organic layer was evaporated and the residue subjected successively to normal-phase column chromatography and HPLC on silica using 55% ethyl acetate/hexane to obtain 25 (9 mg) and 37 (7 mg).

Method II

To a solution of Cryptophycin 8 (20 mg) in 1.0 mL of dry acetone(distilled from $K_2CO_3$) was added 20 mg of LiBr. The mixture was stirred for 24 h at 90° C. After cooling to room temperature, the solvent was evaporated and the residue was subjected to normal-phase HPLC using 50/50 EtOAc/hexane to give Cryptophycin 25 (5.2 mg) and Cryptophycin 37 (4.2 mg).

Spectral Properties of Crvptophycin 25

EIMS m/z (relative intensity) 654/656 (0.5/0.3, M$^+$- HBr), 412/414 (1.4/0.4), 195/197 (11/3), 91 (100); $^1$H NMR ($CDCl_3$): amino or hydroxy acid unit δ (carbon position, multiplicity; J in Hz) 8-bromo-5,7-dihydroxy-6-methyl-8-phenyl-2-octenoic acid (A) 5.80 (2, d; 15.3), 6.70 (3, ddd; 15.3, 9.7 and 5.5), 2.38 (4,m), 2.66 (4, brdd; 14.3, 5.5), 5.11 (5, td; 9.8 and 1.8), 2.58 (6, m), 1.03 (6-Me, d; 7.0), 4.09 (7, brd; 9.9), 4.73 (8, d; 9.9), 7.32–7.42 (10/11/12/13/14, m); 3-chloro-4methoxyphenylalanine (B) 4.81 (2, m), 5.68 (2-NH, d; 8.5), 3.03 (3, dd; 14.4 and 7.4), 3.16 (3, dd; 14.5 and 5.5), 7.23 (5, d; 2.2), 3.88 (7-$OCH_3$, s), 6.85 (8, d; 8.3), 7.09 (9, dd; 8.4 and 2.2); 3-amino-2-methylpropionic acid (C) 2.74 (2, m), 1.23 (2-Me, d; 7.2), 3.26 (3, dt; 13.6, 6.8), 3.53 (3, m), 6.90 (3-NH, brt; 5.8); leucic acid (D) 4.93 (2, dd; 10.1 and 3.1), 1.74–1.63 (3/4, m), 1.49 (3, m), 0.95 (4-Me/5, d; 6.6); $^{13}$C NMR (CDCl$_3$): unit δ (carbon position)A 165.6 (1), 125.2 (2), 141.6 (3), 36.3 (4), 76.4 (5), 39.1 (6), 8.6 (6-Me), 73.5 (7), 53.8 (8), 138.7 (9), 128.3 (10/14), 129.1 (11/12/13); B 171.1 (1), 53.7 (2), 35.0 (3), 130.0 (4), 131.0 (5), 122.4 (6), 153.9 (7), 56.1 (7-OCH$_3$), 112.2 (8), 128.4 (9); C 175.3 (1), 38.3 (2), 14.1 (2-Me), 41.2 (3); D 170.6(1), 71.3 (2), 39.7 (3), 24.7 (4), 21.5 (4-Me), 23.1 (5).

Spectral Properties of Cryptophycin 37

EIMS m/z (relative intensity) 654/656 (3.4/2.0, M$^+$-HBr), 598/600 (311), 412/414 (6/2), 195/197 (27/9), 80 (100); $^1$H NMR (CDCl$_3$): amino or hydroxy acid unit δ (carbon position, multiplicity; J in Hz) 8-bromo-5,7-dihydroxy-6-methyl-8-phenyl-2-octenoic acid (A) 5.71 (2, d; 15.6), 6.65 (3, ddd; 15.1, 9.9 and 5.3), 2.14 (4, dt; 14.5 and 10.7), 2.54 (4, m), 5.07 (5, td; 9.7 and 1.7), 1.52 (6, m), 0.90 (6-Me, d; 6.8), 4.24 (7, brd; 9.9), 5.02 (8, d; 10.1), 7.32–7.39 (10/11/12/13/14, m); 3-chloro-4methoxyphenylalanine (B) 4.79 (2, m), 5.59 (2-NH, d; 8.5), 3.03 (3, dd; 14.5 and 7.2), 3.13 (3, dd; 14.5 and 5.5), 7.21 (5, d; 2.0), 3.87 (7-OCH$_3$, s), 6.83 (8, d; 8.3), 7.07 (9, dd; 8.4 and 2.0); 3-amino-2-methylpropionic acid (C) 2.73 (2, m), 1.23 (2-Me, d; 7.2), 3.29 (3, dt; 13.4, 6.8), 3.50 (3, m), 6.93 (3-NH, brt; 6.0); leucic acid (D) 4.87 (2, dd; 9.8 and 3.6), 1.5 (3, m), 1.55 (3, m), 1.70 (4, m), 0.9 (5, d; 6.6), 0.98 (5', d; 6.8); $^{13}$C NMR (CDCl$_3$): unit δ (carbon position) A 165.4 (1), 125.1 (2), 141.5 (3), 36.2 (4), 76.2 (5), 38.3 (6), 8.4 (6-Me), 74.1 (7), 62.4 (8), 138.1 (9), 127.6 (10/14), 129.2 (11/12/13); B 171.0 (1), 53.6 (2), 35.0 (3), 129.9 (4), 131.0 (5), 122.4 (6), 154.0 (7), 56.1 (7-OCH$_3$), 112.2 (8), 128.4 (9); C 175.5 (1), 38.3 (2), 14.1 (2-Me), 41.2 (3); D 170.4(1), 71.4 (2), 39.7 (3), 24.8 (4), 21.7 (4-Me), 23.1 (5).

Cryptophycin 27

Method I

To a solution of Cryptophycin 1 (500 mg) in 3 mL of 1,2-dimethoxyethane was added 60 μL of concentrated HCl. The mixture was stirred at room temperature for 18 h, potassium carbonate (50 mg) was added, and the mixture was stirred for an additional 2 h, then filtered and evaporated. The residue was subjected to reversed-phase HPLC (Alltech Econosil C18, 250 mm×22 mm column, flow rate 5 mL/min, 20 mg/injection, UV detection at 254 nm) using 3:1 MeCN/H$_2$O to give 433 mg of Cryptophycin 8 (t$_R$ 25 min) and 16 mg of Cryptophycin 27 (t$_R$ 21 min)).

Method II

To a solution of Cryptophycin 8 (20 mg) in 1.0 mL of dry acetone(distilled from K$_2$CO$_3$) was added 20 mg of LiCl. The mixture was stirred for 3 days at 100° C., cooled to room temperature, and evaporated. The residue was subjected to reversed-phase HPLC using 82/18 MeOH/H$_2$O to give Cryptophycin 27 (6.8 mg) and recovered Cryptophycin 8 (10.1 mg).

Spectral Properties of Cryptophycin 27

EIMS m/z (rel intensity) 690/692/694 (0.7/0.4/0.14), 654/656 (8.3/5.4), 412/414 (27/11), 280/282 (23/8), 227 (14), 195/197 (100/33), 155/157 (90/28); high resolution EIMS m/z 690.2491(C$_{35}$H$_{44}$Cl$_2$N$_2$O$_8$, Δ–1.6 mmu), 654.2705 (C$_{35}$H$_{43}$ClN$_2$O$_8$, Δ0.3 mmu). $^1$H NMR (CDCl$_3$) amino or hydroxy acid unit δ (carbon position, multiplicity; J in Hz) 8-chloro-5,7-dihydroxy-6-methyl-8-phenyl-2-octenoic acid (A) 5.70 (2, dd; 15.4 and 1.1), 6.64 (3, ddd; 15.4, 9.8 and 5.4), 2.14 (4, m), 2.53 (4, m), 5.06 (5, ddd; 10.8, 8.0 and 1.7), 1.45 (6, m), 0.94 (6-Me, d; 6.7), 4.07 (7, dt; 9.6 and 2.0), 2.63 (7-OH, broad peak), 4.88 (8, d; 9.6), 7.31 (10/14, m), 7.36–7.40 (11/12/13, m); 3-chloro-4-methoxyphenylalanine (B) 4.79 (2, m), 5.64 (2-NH, d; 8.5), 3.02 (3, dd; 14.4 and 7.4), 3.13 (3, dd; 14.4 and 5.4), 7.21 (5, d; 2.2), 3.86 (7-OCH$_3$, s), 6.83 (8, d; 8.4), 7.07 (9, dd; 8.4 and 2.2); 3-amino-2-methylpropionic acid (C) 2.73 (2, m), 1.23 (2-CH3, d; 7.2), 3.27 (3, m), 3.51 (3, ddd; 13.7, 5.2 and 3.9), 6.91 (3-NH, brt; 6.1); leucic acid (D) 4.85 (2, dd; 9.8 and 3.7), 1.50 (3, ddd; 14.2, 7.6 and 3.7), 1.84 (3, ddd; 14.2, 9.8 and 5.0), 1.69 (4, m). 0.97 (4-Me, d; 6.7), 0.94 (5, d; 6.7). $^{13}$C NMR (CDCl$_3$) unit δ (carbon position) A 165.4 (1), 125.1 (2), 141.5 (3), 36.1 (4), 76.1 (5), 38.4 (6), 8.7 (6-Me), 74.5 (7), 68.6 (8), 137.6 (9), 127.4 (10/14), 129.1 (11/13), 129.2 (12); B 171.0 (1), 53.6 (2), 35.0 (3), 129.9 (4), 131.0 (5), 122.4 (6), 153.9 (7), 61.1 (7-OCH3), 112.2 (8), 128.4 (9); C 175.5 (1), 38.3 (2), 14.1 (2-CH3), 41.2 (3), D 170.4 (1), 71.4 (2), 39.7 (3), 24.8 (4), 23.1 (4-Me), 21.7 (5).

Cryptophycin 32

To a mixture of a catalytic amount of PtO$_2$ in 0.5 mL of CH$_2$Cl$_2$ that had been stirred under H$_2$ for 20 min was added a solution of Cryptophycin 1 (4 mg) in 0.2 mL of CH$_2$Cl$_2$. The mixture was stirred at room temperature under H$_2$ for 45 min. More CH$_2$Cl$_2$ (3 mL) was added, the mixture filtered through cotton/celite, and the solvent evaporated. After reversed-phase HPLC purification, 3.4 mg (94% based on consumed starting material) of 32 was obtained. EIMS m/z (rel intensity) 642/644 (10/14), 398 (24), 266/268 (20/7), 195/197 (60/20), 184/186 (80/20), 127 (60), 91 (100); high resolution EIMS m/z 642.2704 (calcd for C$_{34}$H$_{43}$ClN$_2$O$_8$, Δ0.4 mmu); $^1$H NMR (CDCl$_3$) amino or hydroxy acid unit δ values (carbon positions, multiplicities; J in Hz) 2,3-dihydro-7,8-epoxy-5-hydroxy-6-methyl-8-phenyl octanoic acid (A) 2.29 (2, ddd; –14.7, 7.4, 5.5), 2.06 (2, ddd; –14.7, 9.3, 6.2), 1.5–1.8 (3/4, 4H, overlapping multiplets), 5.05 (5, ddd; 10.1, 8.1, 2.9), 1.70 (6, m), 1.12 (6-Me, d; 6.9), 2.90 (7, dd; 7.7, 1.9), 3.67 (8, d; 1.9), 7.25 (10/14, m), 7.31–7.40 (11/12/13, m); 3-chloro-4methoxyphenylalanine (B) 4.62 (2, ddd; 8.6, 6.6, 6.0), 5.62 (2-NH, d; 8.6), 3.06 (3, dd; –14.1, 6.0), 3.13 (3, dd; –14.1, 6.6), 7.19 (5, d; 2.0), 3.87 (7-OMe; s), 6.83 (8, d; 8.4), 7.06 (9, dd; 8.4, 2.0); 3-amino propionic acid (C) 2.55 (2, m), 3.58 (3, m), 3.48 (3, m), 6.87 (NH, br t; 6.2); leucic acid (D) 4.83 (2, dd; 9.8, 4.1), 1.34 (3, m), 1.70 (3, m), 1.70 (4, m), 0.86 (4-Me; d; 4.3), 0.85 (5, d; 4.3); $^{13}$C NMR (CDCl$_3$) unit δ values (carbon positions) A 172.7 (1), 36.3 (2), 32.0 (3), 21.4 (4), 76.6 (5), 40.2 (6), 13.6 (6-Me), 63.4 (7), 59.2 (8), 136.8 (9), 125.6 (10/14), 128.7 (11/13), 128.5 (12); B 170.6 (1), 54.5 (2), 35.4 (3), 130.0 (4), 131.0 (5), 122.2 (6), 153.8 (7), 56.1 (7-OMe), 112.1 (8), 128.7 (9); C 173.0 (1), 33.2 (2), 34.9 (3); D 171.7 (1), 72.1 (2), 39.1 (3), 24.4 (4), 22.8 (4-Me), 21.4 (5).

Cryptophycin 33

A mixture of 10 mg of Cryptophycin 1 and 0.5 mg 10% Pd/C in 0.5 mL of CH$_2$Cl$_2$ was stirred under an atmosphere of hydrogen at room temperature for 2 hours. An additional 2 mL of CH$_2$Cl$_2$ was added and the mixture was filtered through cotton/celite and the filtrate evaporated. Reversed-phase HPLC purification of the residue on C18 using 65% aqueous CH$_3$CN yielded 8.5 mg of Cryptophycin 33 (85%). EIMS m/z (relative intensity) 658/660(8/3), 567/569 (18/7), 412/414 (15/6), 280/282 (20/11), 195/197 (84/29), 155/157 (50/19), 121 (42), 91 (100); high resolution EIMS m/z 658.3017 (C$_{35}$H$_{47}$ClN$_2$O$_8$, Δ+0.4 mmu); $^1$H NMR (CDCl$_3$) amino or hydroxy acid unit δ values (carbon positions, multiplicities; J in Hz) 5,7-dihydroxy-6-methyl-8-phenyl octanoic acid (A) 2.33 (2, ddd; –14.6, 8.1, 5.7), 2.10 (2, ddd; –14.6, 8.9, 6.6), 1.5–1.8 (3/4, 4 H, overlapping multiplets), 5.04 (5, ddd; 9.7, 5.2, 2.5), 1.75 (6, m), 1.00 (6-Me, d; 7.0), 3.92 (7, ddd; 8.6, 4.8, 2.3), 2.80 (8, dd; -13.7, 8.6), 2.68 (8, dd; -13.7, 4.8), 7.25 (10/14, m), 7.34–7.39 (11/12/13, m); 3-chloro-4methoxyphenylalanine (B) 4.69 (2, ddd; 8.8, 8.6, 6.6), 5.67 (2-NH, d; 8.8), 3.09 (3, 2 H, m), 7.20 (5, d; 2.1), 3.87 (7-OMe, s), 6.83 (8, d; 8.4), 7.07 (9, dd; 8.4, 2.3); 3-amino-2-methylpropionic acid (C) 2.74 (2, m), 1.18 (2-Me, d; 7.1), 3.09 (3, ddd; overlaps with B-3), 3.67 (3, ddd; 13.5, 8.1, 4.3), 6.75 (3-NH, br t; 6.6); leucic acid (D) 4.89 (2, dd; 9.7, 4.1), 1.4–1.8 (3/4, m), 0.93 (4-Me, d; 6.6), 0.90 (5, d; 6.6); $^{13}$C NMR (CDCl$_3$) unit δ values (carbon positions) A 172.6 (1), 36.1 (2), 31.4 (3), 39.3 (4), 76.9 (5), 41.0 (6), 9.3 (6-Me), 71.6 (7), 42.2 (8), 138.5 (9), 128.6 (10/14), 129.1 (11/13), 130.2 (12); B 170.8 (1), 53.8 (2), 35.4 (3), 130.2 (4), 131.2 (5), 122.2 (6), 153.8 (7), 56.1 (7-OMe), 112.1 (8), 129.1 (9); C 174.9 (1), 39.7 (2),13.6 (2-Me), 42.2 (3); D 172.0 (1), 71.7 (2), 21.0 (3), 24.8 (4), 22.9 (4-Me), 21.6 (5).

Cryptophycin 34

A mixture of 2.5 mg of Cryptophycin 4 and 0.1 mg of 10% Pd/C in 0.3 mL of CH$_2$Cl$_2$ was stirred at room temperature under a hydrogen atmosphere for 1 hour. Additional solvent (2 mL) was added and the mixture was filtered through cotton/celite and the filtrate evaporated to yield, after reversed-phase HPLC purification, 2.1 mg of Cryptophycin 34 (84%). EIMS m/z (relative intensity) 608 (10), 377 (35), 333 (10), 232 (38), 161 (100), 121 (85), 91 (65); high resolution EIMS m/z 608.3474 (C$_{35}$H$_{48}$N$_2$O$_7$, Δ−1.2 mmu); $^1$H NMR (CDCl$_3$) amino or hydroxy acid unit δ (carbon positions, multiplicities; J in Hz) 5-hydroxy-6-methyl-8-phenyl octanoic acid (A) 1.20 (6-Me, d, 7.2), 2.55 (6, m); 4methoxyphenylalanine (B) 4.74 (2, ddd, 8.6, 8.5, 6.2), 5.59 (NH, d, 8.5), 7.11 (5/9, d, 8.5), 6.81 (6/8, d, 8.6), 3.78 (7-OMe, s); 3-amino-2-methylpropionic acid (C) 2.69 (2,m), 1.21 (2-Me, d, 7.2), 3.18 (3, m), 3.64 (3', m), 6.81 (3-NH, dd; 9.4, 5.2); leucic acid (D) 4.89 (2, dd, 9.4, 4.7), 1.34 (3, m), 1.65 (4, m), 0.93 (5, d, 6.5), 0.90 (5', d, 6.5); $^{13}$C NMR (CDCl$_3$) δ (carbon positions) A 172.6 (1), 36.3 (2), 33.1 (3), 39.5 (4), 78.2 (5), 41.9 (6), 13.6 (6-Me), 39.3 (7), 41.9 (8), 147.0 (9), 128.2 (10/14), 128.4 (11/13), 125.9 (12); B 171.0 (1), 53.8 (2), 35.7 (3), 128.8 (4), 130.4 (5/9), 114.0 (6,8), 158.4 (7), 55.2 (7-OMe); C 175.3 (1), 36.3 (2)*, 15.5 (2-Me), 30.6 (3)*; D 171.9 (1), 71.9 (2), 22.8 (3), 24.7 (4), 21.4 (5), 21.7 (5').

Cryptophycin 38

A solution of Cryptophycin 3 (22 mg) and m-chloroperbenzoic acid (60% pure, 22 mg) in 1.5 mL of dry CH$_2$Cl$_2$ was stirred at 60° C. for 90 minutes. The reaction mixture was brought to the ambient temperature and added 100 μL of dimethylsulfide to quench excess peroxyacid and continued the stirring with 0.1 sodium phosphate buffer at pH 8 (2×2 mL) to remove 3-chlorobenzoic acid. The organic layer, which tested negative both to litmus and starch iodide paper, was evaporated under nitrogen and the concentrate kept under reduced pressure for overnight. The residue was purified by reversed-phase HPLC (Econosil C18, 250×22 mm, 10μ) using 3:7 H$_2$O/CH$_3$CN to give Cryptophycin-1 (10.4 mg) and Cryptophycin 38 (t$_R$ 39.8 min, 5.9 mg). EIMS m/z (rel intensity); high resolution EIMS m/z (C$_{35}$H$_{43}$ClN$_2$O$_8$, Δ mmu error). $^1$H NMR (CDCl$_3$): amino or hydroxyacid unit δ (carbon position, multiplicity; J in Hz) 7,8-epoxy-5-hydroxy-6-methyl-8-phenyl-2-octenoic acid (A) 5.82 (2, d; 15.4), 6.70 (3, ddd; 15.4, 9.9 and 5.4), 2.57 (4, brdd; 14.5 and 5.4), 2.67 (4, dt; 14.5 and 10.6), 5.14 (5, ddd; 11.2, 5.0 and 1.6), 1.77 (6, m), 1.05 (6-Me, d; 7.1), 2.90 (7, dd; 7.8 and 2.0), 3.60 (8, d; 2.0), 7.22–7.26 (10/14, m), 7.30–7.38 (11/12/13, m); 3-chloro-4-methoxyphenylalanine (B) 4.83 (2, m), 5.72 (2-NH, d; 8.7), 3.05 (3, dd; 14.4 and 7.4), 3.15 (3, dd; 14.4 and 5.5), 7.24 (5, d; 2.1), 3.88(7-OCH$_3$, s), 6.85 (8, d; 8.4), 7.09 (9, dd; 8.4 and 2.1); 3-amino-2-methylpropionic acid (C) 2.73 (2, m), 1.24 (2-Me, d; 7.4), 3.31 (3, dt; 13.9 and 6.7), 3.51 (3, dt; 13.9 and 4.4), 6.98 (3-NH, br t; 5.9); leucic acid (D) 4.92 (2, dd; 10.0 and 3.3), 1.51 (3, m), 1.70–1.77 (3/4, m), 0.89 (4-Me, d; 6.7), 0.91 (5, d; 6.5); $^{13}$C NMR (CDCl$_3$): unit δ (carbon position) A 165.5 (1), 125.3 (2), 141.4 (3), 36.7 (4), 76.9 (5), 41.1 (6), 13.4 (6-Me), 63.2 (7), 56.1 (8), 137.1 (9), 125.4 (10/14), 128.6 (11/13), 128.3 (12); B 171.0 (1), 53.6 (2), 35.1 (3), 129.9 (4), 131.0 (5), 122.5 (6), 154.0 (7), 56.3 (7-OCH$_3$), 112.3 (8), 128.4 (9); C 175.6 (1), 38.3 (2), 14.1 (2-Me), 41.1 (3), D 170.8(1), 71.5 (2), 39.3 (3), 24.7 (4), 21.4 (4-Me), 23.1 (5).

Cryptophycin 39

Method I

A solution of Cryptophycin 27 (6.0 mg) in 1.0 mL of dry acetone was treated with 15 mg of potassium carbonate at 85° C. After 24 h the reaction mixture was filtered and the filtrate was evaporated. The residue was subjected to normal-phase HPLC on silica using 50/50 EtOAc/hexane to give Cryptophycin 39 (3.2 mg).

Method II

A solution of Cryptophycin 37 (5.0 mg) in 1.0 mL of dry acetone was treated with 15 mg of potassium carbonate at 65° C. After 12 h the reaction mixture was filtered and the filtrate was evaporated to give crude Cryptophycin 39 (4.2 mg).

Spectral Properties of Cryptophycin 39

EIMS m/z (rel intensity) 654/656 (6.9/3.3), 412/414 (28/11), 280/282(18/7), 227 (17), 195/197 (100/51); high resolution EMS m/z 654.2711 (C$_{35}$H$_{43}$ClN$_2$O$_8$, Δ−0.3 mmu). $^1$H NMR (CDCl$_3$)amino or hydroxy acid unit δ (carbon position, multiplicity; J in Hz) 7,8-epoxy-5-hydroxy-6-methyl-8-phenyl-2-octenoic acid (A) 5.67 (2, d; 15.5), 6.52 (3, ddd; 15.5, 9.9 and 5.3), 1.79 (4, m), 2.27 (4, dt; 14.5 and 10.8), 4.86 (5, m), 1.79 (6, m), 1.15 (6-Me, d; 6.8), 3.20 (7, dd; 9.4 and 3.7), 4.17 (8, d; 3.7),, 7.25 (10/14, brd; 7.0), 7.35 (11/13, brt; 7.0), 7.30 (12, brt; 7.0); 3-chloro-4-methoxyphenylalanine (B) 4.80 (2, m), 5.59 (2-NH, d; 8.3), 3.04 (3, dd; 14.5 and 7.0), 3.12 (3, dd; 14.5 and 5.5), 7.21 (5, d; 2.2), 3.88 (7-OCH$_3$, s), 6.84 (8, d; 8.6), 7.07 (9, dd; 8.4 and 2.2); 3-amino-2-methylpropionic acid (C) 2.72 (2, m), 1.22 (2-Me, d; 7.2), 3.28 (3, dt; 13.6 and 6.8), 3.50 (3, dt; 13.6, 4.4), 6.89 (3-NH, brt; 4.6); leucic acid (D) 4.86 (2, dd; 10.1 and 3.5), 1.48 (3, m), 1.79 (3, m), 1.70 (4, m). 0.96 (4-Me, d; 6.8), 0.93 (5, d; 6.4). $^{13}$C NMR (CDCl$_3$) unit δ (carbon position) A 165.2 (1), 125.0 (2), 141.1 (3), 36.6 (4), 76.2 (5), 34.2 (6), 14.7 (6-Me), 60.2 (7), 58.7 (8), 135.0 (9), 126.3 (10/14), 128.3 (11/13), 128.0 (12); B 170.9 (1), 53.5 (2), 35.0 (3), 129.8 (4), 131.0 (5), 122.4 (6), 154.0 (7), 56.1 (7-OCH$_3$), 112.3 (8), 128.4 (9); C 175.6 (1), 38.3 (2), 14.1 (2-Me), 41.1 (3), D 170.6 (1), 71.4 (2), 39.6 (3), 24.7 (4), 23.1 (4-Me), 21.4 (5).

Cryptophycins 59 and 64

To a solution of 32 mg (0.05 mmol) of Cryptophycin 35 in 0.9 ml dry dimethoxyethane was added 4 μL of conc. HCl. The mixture was stirred at room temperature for 12 h, neutralized with solid potassium carbonate, and filtered. The filtrate was evaporated and the residue was subjected to reversed-phase HPLC on C$_{18}$ (10 μm, 10×250 mm column) using 65% aqueous CH$_3$CN at a flow rate of 3 mL/min. Pure Cryptophycin 59 (24.4 mg, 73%) eluted at t$_R$ 25.2 min. Pure Cryptophycin 64 (4.6 mg, 14%) eluted at t$_R$ 20.6 min.

Spectral Properties of Cryptophycin 59

EIMS m/z (rel intensity) 692/694 (4/1), 656/658 (14/5), 412/414 (23/8), 280/282 (17/8), 184 (56), 155 (64), 91 (100); high resolution EIMS m/z 692.2679 (calcd for C$_{35}$H46Cl$_2$N$_2$O$_8$, Δ−4.8 mmu); $^1$H NMR (CDCl$_3$): amino or hydroxyacid unit δ (carbon position, multiplicity; J in Hz) 8-chloro-5,7-dihydroxy-6-methyl-8-phenyloctanoic acid (A) 2.32 (2, m), 2.13 (2, m), 1.48–1.65 (3/4, overlapping mult.), 5.04 (5, br t; 8.8), 2.43 (6, m), 0.99 (6-Me, d; 7.0), 3.99 (7, dd; 9.6, 2.0), 4.65 (8, d; 9.6), 7.34–7.41 (10/11/12/13/14, m); 3-chloro-4-methoxyphenylalanine (B) 4.68 (2, m), 5.84 (2-NH, m), 3.08 (3, 2 H, m), 7.20 (5, d; 2.0), 3.86 (7-OMe, s), 6.82 (8, d; 8.6), 7.07 (9, dd; 8.6, 2.0); 3-amino-2-methylpropionic acid (C) 2.74 (2, 2 H, m), 1.18 (2-Me, d; 7.0), 3.08 (3, m), 3.68 (3, m), 6.79 (3-NH, br t; 6.1); leucic acid (D) 4.93 (2, dd; 9.6, 3.7), 1.81 (3, m), 1.58 (3, m), 1.81 (4, m),.0.94 (4-Me, d; 6.6), 0.96 (5, d; 6.6); $^{13}$C NMR (CDCl$_3$) unit δ (carbon position) A 172.6 (1), 36.1 (2), 31.6 (3), 20.9 (4), 76.7 (5), 38.1 (6), 8.6 (6-Me), 74.0 (7), 62.1 (8), 138.7 (9), 128.0 (10/14), 128.9 (11/13), 129.0 (12); B 171.9 (1), 53.8 (2), 35.3 (3),.130.3 (4), 131.1 (5), 122.2 (6), 153.8

(7), 56.1 (7-OMe), 112.1 (8), 128.6 (9); C 174.9 (1), 39.4 (2), 13.5 (2-Me), 42.2 (3); D 170.9 (1), 71.7 (2), 39.7 (3), 24.8 (4), 21.7 (4-Me), 23.0 (5).

Spectral Properties of Cryptophycin 64

$^1$H NMR (CDCl$_3$):amino or hydroxy acid unit δ (carbon position, multiplicity; J in Hz) 8-chloro-5,7-dihydroxy-6-methyl-8-phenyloctanoic acid (A) 2.29 (2, ddd; -14.6, 9.9, 5.0), 2.05 (2, ddd; -14.6, 9.3, 8.2), 1.40 (3, m), 1.61 (3, m), 1.40 (4, m), 4.98 (5, brt; 8.0), 1.61 (6, m), 0.88 (6-Me, d; 6.9), 4.05 (7, dd; 8.5, 1.7), 4.88 (8, d; 8.5), 7.30–7.38 (10/11/12/13/14, m); 3-chloro-4-methoxyphenylalanine (B) 4.67 (2, dt; 8.7, 6.5), 5.73 (2-NH, d; 8.7), 3.08 (3, d; 6.5), 7.18 (5, d; 2.2), 3.85 (7-OMe, s), 6.81 (8, d; 8.4), 7.05 (9, dd; 8.4, 2.2); 3-amino-2-methylpropionic acid (C) 2.72 (2, m), 1.19 (2-Me, d; 6.5), 3.67 (3, ddd; -13.4, 6.8, 4.3), 3.12 (3, ddd; -13.4, 9.1, 6.8), 6.77 (3-NH, brt, 6.8); leucic acid (D) 4.89 (2, dd; 9.5, 4.1), 1.87 (3, m), 1.75 (3, m), 1.53 (4, m), 1.01 (4-Me, d; 6.5), 0.96 (5, d; 6.5); $^{13}$C NMR (CDCl$_3$) unit δ (carbon position) A 172.5 (1), 35.9 (2), 31.3 (3), 20.8 (4), 76.2 (5), 38.0 (6), 8.8 (6-Me), 74.3 (7), 68.5 (8), 137.8 (9), 127.4(10/14), 129.0 (11/13), 129.1 (12); B 171.7 (1), 53.8 (2), 35.2 (3), 130.2 (4), 131.1 (5), 122.2 (6), 153.8 (7), 56.1 (7-OMe), 112.1 (8), 128.6 (9); C 174.9 (1), 39.4 (2), 13.5 (2-Me), 42.2 (3); D 170.8 (1), 71.7 (2), 39.7 (3), 24.8 (4), 21.8 (4-Me), 23.0 (5).

Cryptophycin 60

To a solution of cryptophycin 1 (7 mg, 0.01 mmol) and triphenylphosphine sulfide (6 mg, 0.02 mmol) in 0.5 mL of dry benzene was added trifluoroacetic acid (1.2 mg, 0.8 μL, 0.01 mmol) as a solution in benzene. The solution was allowed to stir at room temperature for 20 hrs, then sodium carbonate was added, the mixture stirred for a further 5 minutes then filtered through a 5μ filter and the solvent removed in vacuo. The residue was taken up in acetonitrile and purified by hplc (ODS, 10μ, 250×10 mm, MeCN/H$_2$O (4:1), 3 mL min$^{-1}$) to return the episulfide (cryptophycin 60, 3.7 mg, 51%) as a colorless amorphous solid.

[α]$_D$ -6.4 (c=1.5, CHCl$_3$); λ$_{max}$ (ε) 204 (32400), 226 (14100), 284 (1050) nm; IR (NaCl) ν$_{max}$ 3406, 3270, 2950, 1751, 1722, 1671, 1640, 1500, 1255, 1189, 1061, 752 cm$^{-1}$; $^1$H NMR (500 MHz, CDCl$_3$) δ Unit A: 7.25–7.33 (10/11/12/13/14-H, m), 6.71 (3-H, ddd, 15.2, 9.7, 5.4), 5.80 (2-H, d, 15.2), 5.21 (5-H, ddd, 11.2, 4.3, 1.9), 3.58 (8-H, d, 5.2), 2.84 (7-H, dd, 8.8, 5.2), 2.65 (4-H$_b$, ddd, 14.5, 11.2, 9.7), 2.56 (4-H$_B$, dddd, 14.5, 5.4, 1.9, 1.9), 1.69–1.78 (6-H, bm, W$_{1/2}$≈25), 1.17 (6-Me, d, 7.1), Unit B: 7.23 (5-H, d, 2.2), 7.09 (9-H, dd, 8.6, 2.2), 6.85 (8-H, d, 8.6), 5.68 (NH, d, 8.4), 4.82 (2-H, ddd, 8.4, 7.3, 5.7), 3.87 (7-OCH$_3$, s), 3.15 (3-H$_b$, dd, 14.5, 5.7), 3.05 (3-H$_B$, dd, 14.5, 7.3), Unit C: 6.97 (NH, m, W$_{1/2}$≈10), 3.50 (3-H$_b$, ddd, 13.4, 9.1, 4.5), 3.31 (3-H$_a$, ddd, 13.4, 6.7, 6.7), 2.73 (2-H, m, W$_{1/2}$≈10), 1.24 (2-CH$_3$, d, 7.3), Unit D: 4.90 (2-H, dd, 9.8, 3.7), 1.69–1.78 (3-H$_b$/4-H, bm, W$_{1/2}$≈25), 1.50 (3-H$_a$, m, W$_{1/2}$≈10), 0.92$^+$ (4-CH$_3$, d, 6.5), 0.90$^+$(5-H$_3$, d, 6.5); $^{13}$C NMR (125 MHz, CDCl$_3$) δ Unit A: 165.4 (1), 141.3 (3), 138.5 (9), 128.7 (11/13), 127.8 (12), 126.9 (10/14), 125.3 (2), 77.0 (5), 44.6 (6), 44.0 (7), 41.1(8), 35.6 (4), 16.3 (6-Me), Unit B: 170.9 (1), 154.0 (7), 131.0 (5), 129.8 (4), 128.4 (9), 122.5 (6), 112.3 (8), 56.1 (7-OMe), 53.6 (2), 35.1 (3), Unit C: 175.5 (1), 41.1 (3), 38.4 (2), 14.1 (2-Me), Unit D: 170.6 (1), 71.4 (2), 39.5 (3), 24.7 (4), 22.9$^+$ (4-Me), 21.5$^+$ (5); MS (EI) m/z 670/672 (M$^+$, <<1), 638/640 (M$^+$- S, 4/2), 618/620 (6/4), 452/454 (15/10), 412/414 (53/31), 280 (18), 227 (87), 207 (71), 195/197 (59/21), 155/157 (100/31), 129 (52), 91 (93), 77 (35); HRMS, obsd m/z 638.2719, C$_{35}$H$_{43}$N$_2$O$_7$$^{35}$Cl (Δ 4.0 mmu), obsd m/z 618.2465 C$_{35}$H$_{39}$N$_2$O$_6$$^{35}$Cl (Δ 3.2 mmu).

(Resonances with identical superscripts are interchangeable)

Cryptophycin 63

To a solution of 1.3 mg of Cryptophycin 40 in 0.2 mL of dry dimethoxyethane was added 1 μL of concentrated HCl. The solution was stirred at room temperature for 30 min, neutralized with solid potassium carbonate, and filtered. The filtrate was evaporated and the residue subjected to reversed-phase HPLC (C$_{18}$, 10 μm, 10×250 mm column, 65% aqueous CH$_3$CN, 3 mL/min flow rate) to give 0.8 mg (62%) of pure Cryptophycin 63 (t$_R$ 16 min). $^1$H NMR (CDCl$_3$):amino or hydroxy acid unit δ (carbon position, multiplicity; J in Hz) 8-chloro-5,7-dihydroxy-8-phenyl-2-octenoic acid (A) 5.75 (2, d; 15.7), 6.68 (3, ddd; 15.1, 9.3, 5.1), 2.45 (4, m), 2.37(4, m), 5.32(5, brt; 10.0), 2.13(6, m), 1.80(6, m), 3.90(7, m), 4.77(8, d; 6.2), 7.36–7.39 (10/11/12/13/14, m); 3-chloro-4methoxyphenylalanine (B) 4.81 (2, m), 5.62 (2-NH, d; 8.0), 3.15 (3, dd; -14.5, 5.5), 3.02 (3, dd; -14.5, 7.1), 7.22 (5, d; 1.5), 3.87 (7-OMe, s), 6.84 (8, d; 8.2), 7.08 (9, dd; 8.2, 1.5); 3-amino-2-methylpropionic acid (C) 2.72 (2,m), 1.22 (2-Me, d; 7.1), 3.51(3, ddd; -13.3, 8.6, 5.9), 3.27 (3, ddd; -13.6, 6.6, 5.9), 6.92 (3-NH, br t; 5.9), leucic acid (D) 4.86 (2, dd;, 9.3, 3.8), 1.73, 3, m), 1.48 (3, m), 1.80 (4, m), 0.96 (4-Me, d; 6.7), 0.93 (5, d; 6.7).

Cryptophycins 69 and 70

A solution of 6.0 mg of Cryptophycin 38 in 0.5 mL of dimethoxythane was treated with 2 μL concentrated HCl at room temperature. After 12 hours the excess acid was neutralized by stirring with 20 mg of solid potassium carbonate. The reaction mixture was filtered and the solvent evaporated to obtain a residue which was subjected to reversed-phase HPLC (C18, 10 μm, 22×250 mm column, 3:1 CH$_3$CN/H$_2$O, 3 mL/min flow rate) to give 4.3 mg of Cryptophycin 69 (t$_R$ 25.6 min) and 1.1 mg of Cryptophycin 70 (t$_R$ 24 min).

Spectral Properties of Cryptophycin 69

EIMS m/z (relative intensity); high resolution EIMS m/z (C$_{35}$H$_{44}$Cl$_2$N$_2$O$_8$, Δ mmu). $^1$H NMR (CDCl$_3$) amino or hydroxy acid unit δ (carbon positions, multiplicity; J in Hz) 8-chloro-5,7-dihydroxy-6-methyl-8-phenyl-2-octenoic acid (A) 5.75 (2, d; 15.2), 6.69 (3, ddd; 15.2, 9.8 and 5.3), 2.37 (4, dt; 14.4 and 10.6), 2.58 (4, brdd; 14.4 and 5.4), 5.40 (5, m), 1.83 (6, m), 1.06 (6-Me, d; 7.0), 3.76 (7, t; 5.8), 5.08 (8, d; 5.8), 7.31–7.40 (10/11/12/13/14, m); 3-chloro-4-methoxyphenylalanine (B) 4.81 (2, m), 5.69 (2-NH, d; 8.5), 3.04 (3, dd; 14.4 and 7.2), 3.12 (3, dd; 14.4 and 5.4), 7.21 (5, d; 2.2), 3.87 (7-OCH$_3$, s), 6.84 (8, d; 8.3), 7.07 (9, dd; 8.3 and 2.2); 3-amino-2-methylpropionic acid (C) 2.71 (2, m), 1.23 (2-Me, d; 7.4), 3.32 (3, dt; 13.2 and 6.7), 3.48 (3, m), 6.97 (3-NH, brd;6. 1); leucic acid (D) 4.81 (2, dd; 9.5 and 4.6), 1.68 (3, m), 1.43 (3, m), 1.59 (4, m), 0.86 (4-Me, d; 6.7), 0.91 (5, d; 6.7). $^{13}$C NMR (CDCl$_3$): unit δ (carbon position) A 165.5 (1), 125.0 (2), 142.0 (3), 34.6 (4), 74.3 (5), 39.7 (6), 12.9 (6-Me), 77.7 (7), 67.1 (8), 138.2 (9), 127.6 (10/14), 128.9 (11/13), 128.9 (12); B 171.0 (1), 53.6 (2), 35.1 (3), 129.9 (4), 131.0 (5), 122.4 (6), 154.0 (7), 56.1 (7-OCH$_3$), 112.3 (8), 128.4 (9); C 175.5 (1), 38.4 (2), 14.1 (2-Me), 41.2 (3); D 170.3(1), 71.5 (2), 39.4 (3), 24.6 (4), 21.7 (4-Me), 22.7 (5).

Spectral Properties of Cryptophycin 70

EIMS m/z (relative intensity); high resolution EIMS m/z (C$_{35}$H$_{44}$Cl$_2$N$_2$O$_8$, Δ mmu). $^1$H NMR (CDCl$_3$) amino or hydroxy acid unit δ (carbon positions, multiplicity; J in Hz) 8-chloro-5,7-dihydroxy-6-methyl-8-phenyl-2-octenoic acid (A) 5.77 (2, d; 15.2), 6.69 (3, ddd; 15.2, 9.8 and 5.3), 2.43 (4, dt; 14.4 and 10.4), 2.54 (4, brdd; 14.4 and 5.5), 5.43 (5, m), 1.88 (6, m), 1.02 (6-Me, d; 7.2), 3.93 (7, dd; 7.4 and 5.4), 4.94 (8, d; 5.4), 7.31–7.48 (10/11/12/13/14, m); 3-chloro-4methoxyphenylalanine (B) 4.82 (2, m), 5.66 (2-NH, d; 8.8), 3.05 (3, dd; 14.4 and 7.1), 3.15 (3, dd; 14.4 and 4.9), 7.22 (5, d; 2.2), 3.87 (7-OCH$_3$, s), 6.84 (8, d; 8.3), 7.08 (9, dd; 8.3 and 2.2); 3-amino-2-methylpropionic acid (C) 2.71 (2, m), 1.22 (2-Me, d; 7.6), 3.28 (3, dt; 13.5 and 6.8), 3.50 (3, m), 6.93 (3-NH, brt; 6.6); leucic acid (D) 4.83 (2, dd; 10.1 and 4.9), 1.56–1.72 (3, m), 1.50 (3, m), 1.56–1.72 (4, m), 0.85 (4-Me, d; 6.7), 0.88 (5, d; 6.7). $^{13}$C NMR (CDCl$_3$): unit δ

(carbon position) A 165.5 (1), 125.0 (2), 142.0 (3), 34.4 (4), 74.7 (5), 39.4 (6), 11.9 (6-Me), 77.0 (7), 64.5 (8), 136.9 (9), 128.6 (10/14), 128.8 (11/13), 129.1 (12); B 171.0 (1), 53.5 (2), 35.1 (3), 129.9 (4), 131.1 (5), 122.4 (6), 154.0 (7), 56.2 (7-OCH$_3$), 112.3 (8), 128.5 (9); C 175.5 (1), 38.5 (2), 14.1 (2-Me), 41.3 (3); D 170.4(1), 71.5 (2), 39.4 (3), 24.6 (4), 21.7 (4-Me), 22.6 (5).

Cryptophycins 71 and 72

A solution of 7 mg of Cryptophycin 38 in 1 mL of dimethoxyethane was treated with 10 μL of 30% HBr in acetic acid at 50° C. for 18 hours. The mixture was brought to the ambient temperature and stirred with 20 mg of powdered dry potassium carbonate for 3 hours. The solution was filtered, the solvent evaporated and the residue subjected to HPLC on an Econosil silica column (250×10 mm, 5μ, 1:1 ethylacetate/hexane, 3 mL/min) to obtain 3.3 mg of crypptophycin 71 (t$_R$ 49.6 min) and 2.8 mg of cryptophycin 72 (t$_R$ 46 min).

Spectral Properties of Cryptophycin 71

EIMS m/z (relative intensity); high resolution EIMS m/z (C$_{35}$H$_{44}$ClBrN$_2$O$_8$, Δ mmu). $^1$H NMR (CDCl$_3$) amino or hydroxy acid unit δ (carbon positions, multiplicity; J in Hz) 8-bromo-5,7-dihydroxy-6-methyl-8-phenyl-2-octenoic acid (A) 5.75 (2, d; 15.3), 6.69 (3, ddd; 15.3, 9.6 and 5.4), 2.35 (4, dt; 14.6 and 10.6), 2.61 (4, brdd; 14.6 and 5.3), 5.38 (5, ddd; 11.2, 3.9 and 1.5), 1.78 (6, m), 1.06 (6-Me, d; 7.0), 3.76 (7, t; 5.8), 5.18 (8, d; 5.8), 7.41 (10/14, dd; 8.1 and 1.3), 7.29–7.37 (11/12/13, m); 3-chloro-4-methoxyphenylalanine (B) 4.82 (2, m), 5.64 (2-NH, brd; 7.4), 3.06 (3, dd; 14.6 and 7.1), 3.12 (3, dd; 14.6 and 5.6), 7.22 (5, d; 2.0), 3.87 (7-OCH$_3$, s), 6.84 (8, d; 8.5), 7.08 (9, dd; 8.5 and 2.0); 3-amino-2-methylpropionic acid (C) 2.71 (2, m), 1.24 (2-Me, d; 7.4), 3.32 (3, dt; 13.4 and 6.7), 3.49 (3, dt; 13.4 and 4.2), 6.96 (3-NH, brt; 5.8); leucic acid (D) 4.79 (2, dd; 9.5 and 4.5), 1.40 (3, m), 1.66 (3, m), 1.55 (4, m), 0.85 (4-Me, d; 6.6), 0.90 (5, d; 6.6). $^{13}$C NMR (CDCl$_3$): unit δ (carbon position) A 165.5 (1), 124.9 (2), 142.0 (3), 34.9 (4), 74.0 (5), 40.0 (6), 13.2 (6-Me), 77.6 (7), 61.6 (8), 138.6 (9), 128.1 (10/14), 129.0 (11/13), 129.0 (12); B 171.0 (1), 53.6 (2), 35.1 (3), 129.8 (4), 131.0 (5), 122.4 (6), 154.0 (7), 56.1 (7-OCH$_3$), 112.3 (8), 128.4 (9); C 175.6 (1), 38.4 (2), 14.1 (2-Me), 41.1 (3); D 170.3(1), 71.5 (2), 39.4 (3), 24.6 (4), 21.7 (4-Me), 22.7 (5).

Spectral Properties of Cryptophycin 72

EIMS m/z (relative intensity); high resolution EIMS m/z (C$_{35}$H$_{44}$ClBrN$_2$O$_8$, Δ mmu). $^1$H NMR (CDCl$_3$) amino or hydroxy acid unit δ (carbon positions, multiplicity; J in Hz) 5-hydroxy-6-methyl-7-oxo-8-phenyl-2-octenoic acid (A) 5.77 (2, d; 15.3), 6.69 (3, ddd; 15.3, 9.6 and 5.6), 2.43 (4, dt; 14.1 and 10.4), 2.52 (4, brdd; 14.1 and 5.5), 5.43 (5, m), 1.89 (6, m), 0.98 (6-Me, d; 6.9), 4.01 (7, dd; 7.8 and 4.9), 5.10 (8, d; 4.9), 7.52 (10/14, d; 7.7 and 1.9), 7.32–7.37 (11/12/13, m); 3-chloro-4-hydroxyphenylalanine (B) 4.83 (2, m), 5.63 (2-NH, brd; 8.7), 3.06 (3, dd; 14.5 and 7.0), 3.13 (3, dd; 14.5 and 5.4), 7.22 (5, d; 2.1), 3.88 (7-OCH$_3$, s), 6.84 (8, d; 8.4), 7.08 (9, dd; 8.4 and 2.1); 3-amino-2-methylpropionic acid (C) 2.71 (2, m), 1.22 (2-Me, d; 7.4), 3.28 (3, dt; 13.6 and 6.7), 3.50 (3, dt; 13.6 and 4.6), 6.93 (3-NH, brt; 6.0); leucic acid (D) 4.83 (2, dd; 9.2 and 4.9), 1.50 (3, m), 1.68 (3, m), 1.54–1.63 (4, m), 0.85 (4-Me, d; 6.5), 0.87 (5, d; 6.7). $^{13}$C NMR (CDCl$_3$): unit δ (carbon position) A 165.5 (1), 125.0 (2), 141.9 (3), 34.2 (4), 74.7 (5), 39.6 (6), 11.9 (6-Me), 77.2 (7), 57.5 (8), 137.4 (9), 128.8 (10/14), 129.0 (11/13), 129.1 (12); B 171.0 (1), 53.5 (2), 35.1 (3), 129.9 (4), 131.1 (5), 122.4 (6), 154.0 (7), 56.1 (7-OCH$_3$), 112.3 (8), 128.5 (9); C 175.5 (1), 38.4 (2), 14.0 (2-Me), 41.2 (3); D 170.4(1), 71.5 (2), 39.4 (3), 24.6 (4), 21.8 (4-Me), 22.6 (5).

Cryptophycin 73

A solution of 5 mg Cryptophycin-21 in 1.0 ml CHCl$_3$ was cooled to −60° C. and 10 μl of trimethylsilylchoride was added. The mixture was allowed to stir at −60° C. for 15 min at which time the reaction was judged to be complete. Purification by reversed phase HPLC (C18, 10 μm, 10×250 mm, 65% aqueous CH$_3$CN at 5 ml/min) yielded 4.5 mg of pure 73. H NMR (CD$_3$OD):amino or hydroxy acid unit δ (carbon position, multiplicity; J in Hz) 8-chloro-5,7-dihydroxy-6-methyl-8-phenyl-2-octenoic acid (A) 5.91 (2, dd; −15.3, 1.8), 6.70 (3, ddd; −15.3, 11.2, 4.2), 2.50 (4, m), 2.33 (4, m), 5.10 (5, m), 2.50 (6, m), 1.01 (6-Me, d; 7.0), 4.01 (7, dd; 9.7, 2.0), 4.76 (8, d; 9.7), 7.29–7.41 (10/11/12/13/14, m); 3-chloro-4-methoxyphenylalanine (B) 4.50 (2, dd; 10.3, 4.8), 3.14 (3, dd; −14.1, 4.8), 2.77 (3, dd; −14.1, 10.3), 7.27 (5, d; 2.2), 3.83 (7-OMe, s), 6.96 (8, d; 8.3), 7.15 (9, dd; 8.3, 2.2); 3-aminopropionic acid (C) 2.73 (2, m), 2.63 (2, m), 3.55 (3, ddd; −13.8, 7.7, 3.9), 3.36 (3, ddd; −13.8, 11.8, 3.1); leucic acid (D) 5.10 (2, m), 1.75 (3, m), 1.56 (3, m), 1.75 (4, m), 0.97 (4-Me, d; 6.3), 0.96 (5, d; 6.3); $^{13}$C NMR (CD$_3$OD) unit δ (carbon position) A 168.4 (1), 123.2 (2), 143.8 (3), 36.2 (4), 77.3 (5), 41.4 (6), 8.8 (6-Me), 74.6 (7), 63.9 (8), 141.3 (9), 129.4* (10/14), 129.5* (11/13), 129.6 (12); B 173.1 (1), 56.6 (2), 35.0 (3), 131.6 (4), 132.2 (5), 115.3* (6), 155.2 (7), 57.0 (7-OMe), 113.5* (8), 125.6 (9); C 174.0 (1), 33.3 (2), 37.8 (3); D 172.2 (1), 72.5 (2), 40.4 (3), 25.9 (4), 23.4 (4-Me), 22.0 (5).

Cryptophycin 74

A solution of 4 mg Cryptophycin-2 in 1.0 ml CHCl$_3$ was cooled to −60° C. and 10 μl of trimethylsilylchoride was added. The mixture was allowed to stir at −60° C. for 15 min at which time the reaction was judged to be complete. Purification by reversed phase HPLC (C18, 10 μm, 10×250 mm, 65% aqueous CH$_3$CN at 5 ml/min) yielded 3.7 mg of pure 74. $^1$H NMR (CDCl$_3$):amino or hydroxy acid unit δ (carbon position, multiplicity; J in Hz) 8-chloro-5,7-dihydroxy-6-methyl-8-phenyl-2-octenoic acid (A) 5.77 (2, d; 15.0), 6.71 (3, ddd; 15.0, 9.9, 4.6), 2.68 (4, m), 2.37 (4, m), 5.13 (5, ddd; 11.0, 5.1, 2.0), 2.49 (6, m), 1.04 (6-Me, d; 7.0), 4.01 (7, dd; 9.6. 1.5), 4.65 (8, d; 9.6), 7.34–7.40 (10/11/12/13/14, m); 4-methoxyphenylalanine B) 4.79 (2, m), 5.73 (2-NH, d; 7.4), 3.16 (3, dd; −14.2, 5.1), 3.04 (3, dd; -14.2, 7.0), 7.12 (5/9, d; 8.2), 6.82 (6/8, d; 8.2), 3.78 (7-OMe, s); 3-aminopropionic acid (C) 2.70 (2, m), 1.22 (2-Me, d; 7.2), 3.44 (3, brd; −13.0), 3.23 (3, ddd; −13.0, 5.5, 3.4), 7.02 (3-NH, m); leucic acid (D) 4.93 (2, dd; 9.6, 3.7), 1.74 (3/4, m), 1.44 (3, m), 0.93 (4-Me/S, d; 6.6); $^{13}$C NMR (CDCl$_3$) unit δ (carbon position) A 165.4 (1), 125.1 (2), 141.7 (3), 36.4 (4), 76.2 (5), 38.2 (6), 8.6 (6-Me), 74.1 (7), 62.0 (8), 138.4 (9), 128.0 (10/14), 129.0 (11/13), 129.2 (12); B 171.3 (1), 53.9 (2), 35.3 (3), 128.6 (4), 130.2 (5), 114.1 (6), 158.6 (7), 55.2 (7-OMe), 114.1 (8), 130.2 (9); C 175.6 (1), 38.4 (2), 14.1 (2-Me), 40.9 (3); D 170.6 (1), 71.3 (2), 39.7 (3), 24.7 (4), 23.0 (4-Me), 21.5 (5).

Cryptophycins 75 and 76

A solution of 10 mg of Cryptophycin 1 and 2 μL of HF in 1 ML of dimethoxyethane was stirred at 5° C. for 4 h and at room temperature for 8 hours, and then neutralized with solid potassium carbonate. The reaction mixture was filtered, the solvent evaporated and the residue purified on an Econosil C18 HPLC column (250×22 mm, 10μ, 3:7 H$_2$O/CH$_3$CN, 5 mL/min) to give a mixture of Cryptophycins 15 and 22 (2 mg), Crypptophycin 20 (4 mg), Cryptophycin 75 (2 mg, t$_R$ 30.6 min) and cryptophycin 76 (1.2 mg, t$_R$ 26 min).

Spectral Properties of Cryptophycin 75

$^1$H NMR (CDCl$_3$) amino or hydroxy acid unit δ (carbon positions, multiplicity; J in Hz) 8-jluoro-5,7-dihydroxy-6-methyl-8-phenyl-2-octenoic acid (A) 5.78 (2, d; 15.3), 6.68 (3, ddd; 15.3, 9.7 and 5.5), 2.38 (4, dt; 14.1 and 10.5), 2.63 (4, brdd; 14.1 and 5.3), 5.12 (5, m), 2.25 (6, m), 1.09 (6-Me, d; 6.9), 3.89 (7, m), 5.24 (8, dd; 46.8 and 8.7), 7.35–7.43 (10/111/12/13114, m); 3-chloro-4-methoxyphenylalanine (B) 4.79 (2, m), 5.78 (2-NH, m), 3.00 (3, dd; 14.4 and 7.6), 3.15 (3, dd; 14.4 and 5.6), 7.22 (5, d; 2.0), 3.87 (7-OCH$_3$, s), 6.84 (8, d; 8.4), 7.08 (9, dd; 8.4 and 2.0); 3-amino-2- methylpropionic acid (C) 2.72 (2, m), 1.21 (2-Me, d; 7.1), 3.24 (3, dt; 13.7 and 6.7), 3.52 (3, dt; 13.7 and 4.5), 6.93 (3-NH, brt; 5.7); leucic acid (D) 4.89 (2, dd; 10.0 and 3.6), 1.39–1.45 (3, m), 1.66–1.78 (3, m), 1.66–1.78 (4, m), 0.90 (4-Me, d; 6.4), 0.91 (5, d; 6.4). $^{13}$C NMR (CDCl$_3$): unit δ (carbon position) A 165.5 (1), 125.2 (2), 141.5 (3), 35.0 (4), 76.5 (5), 37.8 (6), 9.0 (6-Me), 72.3 (7), 92.9 (8), 137.2 (9), 126.5 (10/14), 128.8 (11/13), 129.3 (12); B 171.0 (1), 53.6 (2), 36.1 (3), 130.0 (4), 131.0 (5), 122.4 (6), 153.9 (7), 56.1 (7-OCH$_3$), 112.3 (8), 128.4 (9); C175.3 (1), 38.3 (2), 14.0 (2-Me), 41.2 (3); D 170.7(1), 71.3 (2), 39.7 (3), 24.7 (4), 21.5 (4-Me), 23.0 (5).

Spectral Properties of Cryptophycin 76

$^1$H NMR (CDCl$_3$) amino or hydroxy acid unit δ (carbon positions, multiplicity; J in Hz) 8-fluro-5,7-dihydroxy-6-methyl-8-phenyl-2-octenoic acid (A) 5.72 (2, dd; 15.3 and 1.0), 6.63 (3, ddd; 15.3, 9.7 and 5.5), 2.18 (4, dt; 14.1 and 10.6), 2.54 (4, brdd; 14.1 and 5.5), 5.07 (5, m), 1.41–1.50 (6, m), 1.03 (6-Me, d; 7.0), 4.0 (7, ddd; 15.4, 8.1 and 1.6), 5.32 (8, dd; 48.1 and 8.1), 7.29–7.31 (10/14, m), 7.39–7.42 (11/12/13, m); 3-chloro-4-methoxyphenylalanine (B) 4.79 (2, m), 5.66 (2-NH, d; 8.5), 3.01 (3, dd; 14.5 and 7.4), 3.14 (3, dd; 14.5 and 5.6), 7.21 (5, d; 2.2), 3.86 (7-OCH$_3$, s), 6.83 (8, d; 8.3), 7.07 (9, dd; 8.3 and 2.2); 3-amino-2-methylpropionic acid (C) 2.72 (2, m), 1.22 (2-Me, d; 7.2), 3.26 (3, dt; 13.6 and 6.7), 3.51 (3, ddd; 13.6, 5.3 and 3.8), 6.90 (3-NH, brt; 5.9); leucic acid (D) 4.82 (2, dd; 10.0 and 3.6), 1.41–1.50 (3, m), 1.80 (3, m), 1.68 (4, m), 0.90 (4-Me, d; 6.6), 0.95 (5, d; 6.8). $^{13}$C NMR (CDCl$_3$): unit δ (carbon position) A 165.4 (1), 125.1 (2), 141.4 (3), 35.0 (4), 75.9 (5), 38.1 (6), 9.4 (6-Me), 73.3 (7), 96.5 (8), 136.0 (9), 126.6 (10/14), 128.9 (11/13), 129.5 (12); B 171.0 (1), 53.6 (2), 35.9 (3), 129.9 (4), 131.0 (5), 122.4 (6), 153.9 (7), 56.1 (7-OCH$_3$), 112.2 (8), 128.4 (9); C 175.4 (1), 38.3 (2), 14.0 (2-Me), 41.2 (3); D 170.4(1), 71.3 (2), 39.6 (3), 24.7 (4), 21.6 (4-Me), 23.0 (5).

EXAMPLE 10

Analysis of Microtubule Depolymerizing Activity of Cryptophycin

Materials

Vinblastine, cytochalasin B, tetramethylrhodamine isothiocyanate (TRITC)-phalloidin, sulforhodamine B (SRB) and antibodies against P-tubulin and vimentin were obtained from the Sigma Chemical Company. Basal Medium Eagle containing Earle's salts (BME) was from Gibco and Fetal Bovine Serum (FBS) was purchased from Hyclone Laboratories.

Cell Lines

The Jurkat T cell leukemia line and A-10 rat aortic smooth muscle cells were obtained from the American Type Culture Collection and were cultured in BME containing 10% FBS and 50 μg/ml gentamycin sulfate. Human ovarian carcinoma cells (SKOV3) and a sub-line which has been selected for resistance to vinblastine (SKVLB1) were a generous gift from Dr. Victor Ling of the Ontario Cancer Institute. Both cell lines were maintained in BME containing 10% FBS and 50 μg/ml gentamycin sulfate. Vinblastine was added to a final concentration of 1 μg/ml to SKVLB1 cells 24 hours after passage to maintain selection pressure for P-glycoprotein-overexpressing cells.

Cell Proliferation and Cycle Arrest Assays

Cell proliferation assays were performed as described by Skehan et al.[11] For Jurkat cells, cultures were treated with the indicated drugs as described in Skehan[11] and total cell numbers were determined by counting the cells in a hemacytometer. The percentage of cells in mitosis was determined by staining with 0.4% Giemsa in PBS followed by three rapid washes with PBS. At least 1000 cells per treatment were scored for the presence of mitotic figures and the mitotic index was calculated as the ratio of cells with mitotic figures to the total number of cells counted.

Immunofluorescence Assays

A-10 cells were grown to near-confluency on glass coverslips in BME/10% FBS. Compounds in PBS were added to the indicated final concentrations and cells were incubated for an additional 24 hours. For the staining of microtubules and intermediate filaments, the cells were fixed with cold methanol and incubated with PBS containing 10% calf serum to block nonspecific binding sites. Cells were then incubated at 37° C. for 60 min with either monoclonal anti-β-tubulin or with monoclonal anti-vimentin at dilutions recommended by the manufacturer. Bound primary antibodies were subsequently visualized by a 45-minute incubation with fluorescein-conjugated rabbit antimouse IgG. The coverslips were mounted on microscope slides and the fluorescence patterns were examined and photographed using a Zeiss Photomicroscope Ill equipped with epifluorescence optics for fluorescein. For staining of microfilaments, cells were fixed with 3% paraformaldehyde, permeabilized with 0.2% Triton X-100 and chemically reduced with sodium borohydride (1 mg/ml). PBS containing 100 nM TRITC-phalloidin was then added and the mixture was allowed to incubate for 45 min at 37° C. The cells were washed rapidly three times with PBS before the coverslips were mounted and immediately photographed as described above.

Figure 2A:
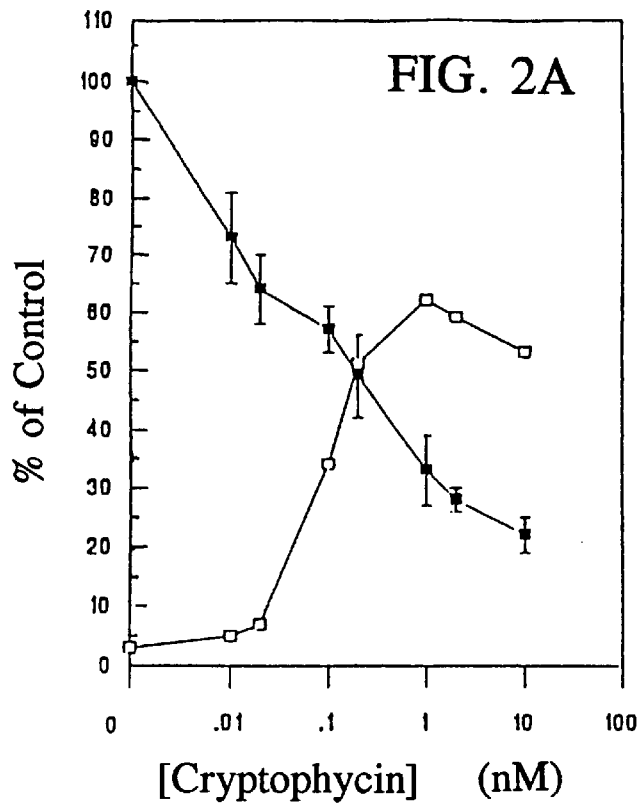
FIGS. 2a and 2b graphically presents the effects of cryptophycin compounds and vinblastine on Jurkat cell proliferation and cell cycle progression. Jurkat cells were incubated with the indicated concentrations of cryptophycin compounds (A) or vinblastine (B) for 24 hours. For each sample, the number of viable cells (■) and the mitotic index (□) were determined as described in the Experimental section. Values represent the means ± standard deviation (sd) for triplicate samples in one of three similar experiments.
Figure 2B:
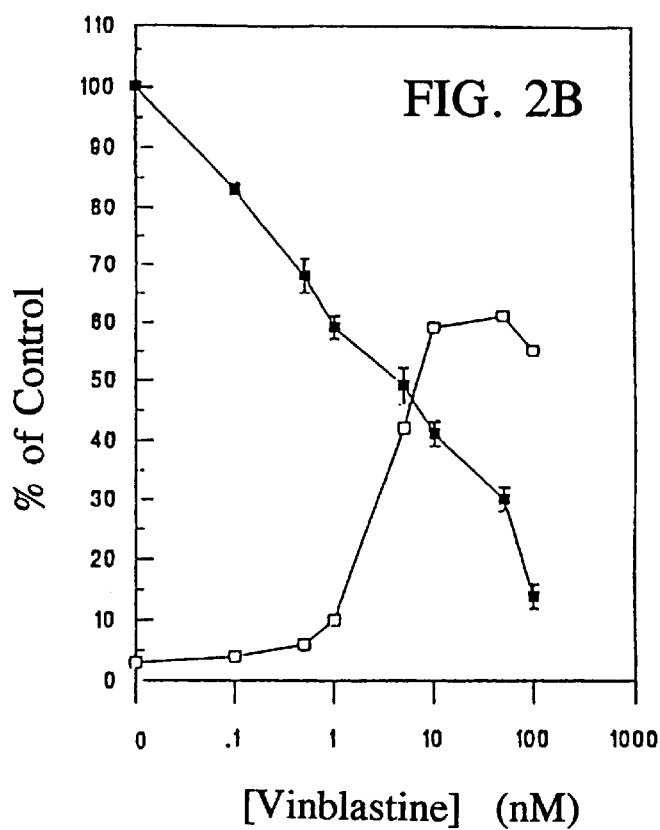

Effects of cryptophycins and vinblastine on Jurkat cell proliferation and cell cycle Dose-response curves for the effects of cryptophycin compounds and vinblastine on cell proliferation and the percentage of cells in mitosis are indicated in FIGS. 2A and 2B, respectively. Less than 3% of untreated cells displayed mitotic figures. Both the cryptophycin compounds and vinblastine caused dose-dependent increases in the percentage of cells observed in mitosis. The increase in the mitotic index was closely correlated with decreases in cell proliferation, i.e. the concentrations of both cryptophycin compounds and vinblastine that caused 50% of the cells to accumulate in mitosis was virtually the same as the concentration which inhibited cell proliferation by 50%. The IC$_{50}$s for the cryptophycin compounds and vinblastine for these effects were 0.2 and 8 nM, respectively.

Effects of cytochalasin B, vinblastine and crytophycins on the cytoskeleton

Aortic smooth muscle (A-10) cells were grown on glass coverslips and treated with PBS, 2 μM cytochalasin B, 100 nM vinblastine or 10 nM cryptophycin compounds. After 24 hours, microtubules and vimentin intermediate filaments were visualized by indirect immunofluorescence and microfilaments were stained using TRITC-phalloidin. The morphological effects of each drug were examined. Untreated cells displayed extensive microtubule networks complete with perinuclear microtubule organizing centers. Vimentin intermediate filaments were also evenly distributed throughout the cytoplasm, while bundles of microfilaments were concentrated along the major axis of the cell. Cytochalasin B caused complete depolymerization of microfilaments along with the accumulation of paracrystalline remnants. This compound did not affect the distribution of either microtubules or intermediate filaments. Both vinblastine and the cryptophycin compound caused marked depletion of microtubules. Neither compound affected microfilament organization; however, vimentin intermediate filaments collapsed, forming concentric rings around the nuclei of cells treated with either vinblastine or a cryptophycin compound.

Effects of cryptophycins and vinblastine on taxol-stabilized microtubules

A-10 cells were treated for 3 hours with 0 or 10 μM taxol before the addition of PBS, 100 nM vinblastine or 10 nM cryptophycin compound. After 24 hours, microtubule organization was examined by immunofluorescence as described above. Compared with those in control cells, microtubules in taxol-treated cells were extensively bundled, especially in the cell polar regions. As before, vinblastine caused complete depolymerization of microtubules in non-pretreated cells. However, pretreatment with taxol prevented microtubule depolymerization in response to vinblastine. Similarly, taxol pretreatment completely stabilized microtubules against cryptophycin-induced depolymerization.

Reversibility of microtubule depolymerization by vinblastine and cryptophycin

A-10 cells were treated with either 100 nM vinblastine or 10 nM cryptophycins for 24 hr, resulting in complete microtubule depolymerization. The cells were then washed and incubated in drug-free medium for periods of 1 hour or 24 hours. Microtubules repolymerized rapidly after the removal of vinblastine, showing significant levels of microtubules after 1 hour and complete morphological recovery by 24 hour. In contrast, microtubules did not reappear in cells treated with cryptophycin compounds at either 1 hour or 24 hours after removal of the compound.

Figure 3:
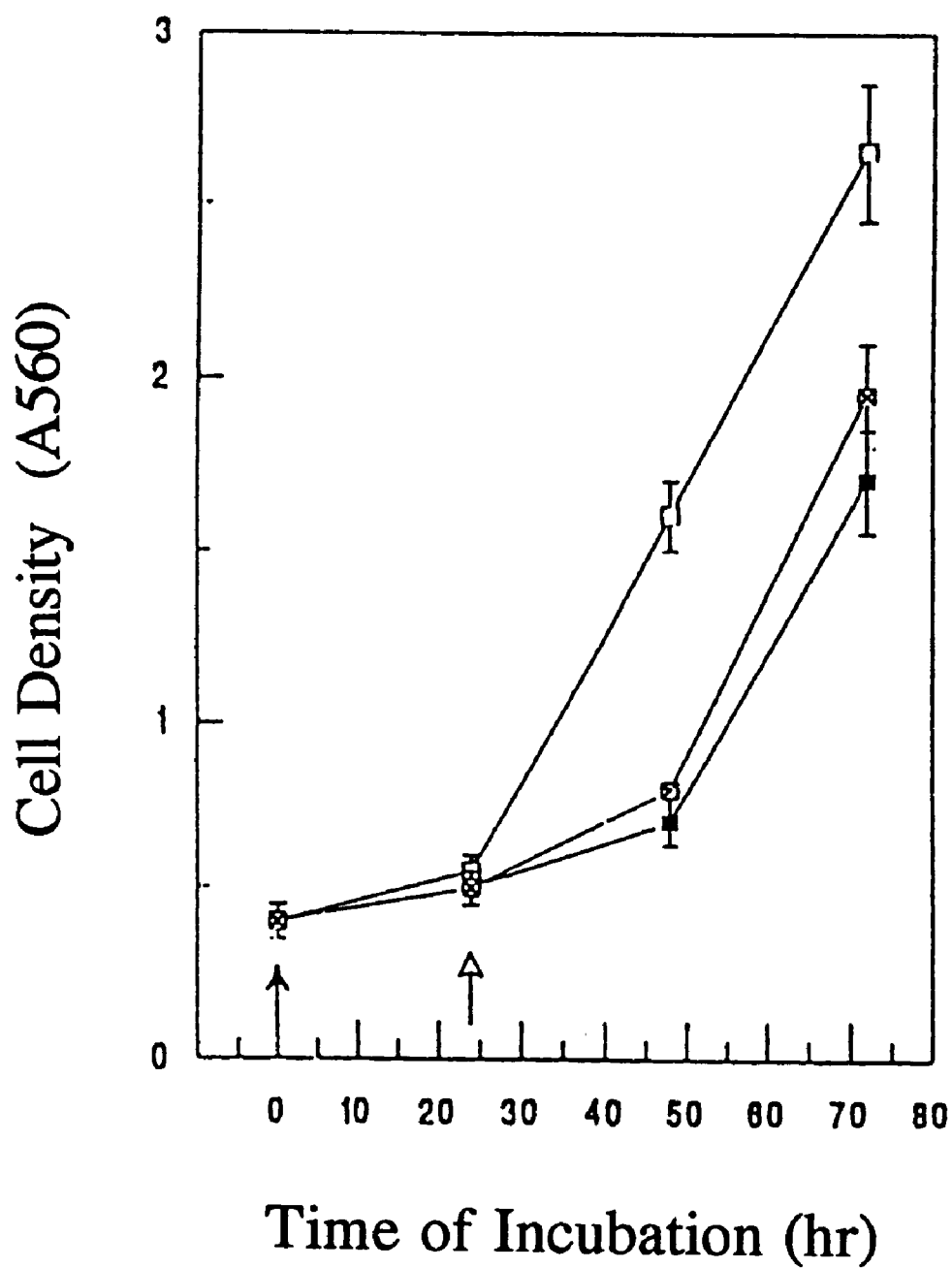
FIG. 3 graphically presents the reversibility of the effects of vinblastine, cryptophycins and taxol on cell growth. SKOV3 cells were treated with 0.1 nM vinblastine (□), 0.1 nM cryptophycins (■) or 1 nM taxol ⊠ at time=0. These concentrations inhibited cell growth by 50% for each compound. After 24 hours the cells were washed and incubated in drug-free medium for the time indicated. The cell density was determined by sulforhodamine B (SRB) staining as described in the Experimental Section, and is expressed as the mean ±sd absorbance at 560 nm for triplicate samples in one of three experiments.

Reversibility of cryptophycins-, vinblastine- and taxol-inhibition of cell proliferation SKOV3 cells were treated for 24 hours with previously determined $IC_{50}$ doses of vinblastine, cryptophycin compounds or taxol (i.e. values determined in experiments summarized in Table 5). During this time the cell density increased from 0.4 to 0.5±0.05 absorbance units (FIG. 3), indicating a 25% increase in cell number for all three treatments. Removal of the drugs resulted in rapid growth of the vinblastine-treated cells, such that their numbers were increased approximately 3-fold in 24 hours. In contrast, cells treated with cryptophycin compounds or taxol remained arrested, increasing only 0.2- to 0.4-fold in the 24 hours following removal of the drug. The proliferative capacity of cryptophycins or taxol-treated cells was subsequently restored since the cells then doubled in the next 24 hours.

Effects of combinations of vinblastine and cryptophycins on cell proliferation

Figure 4:
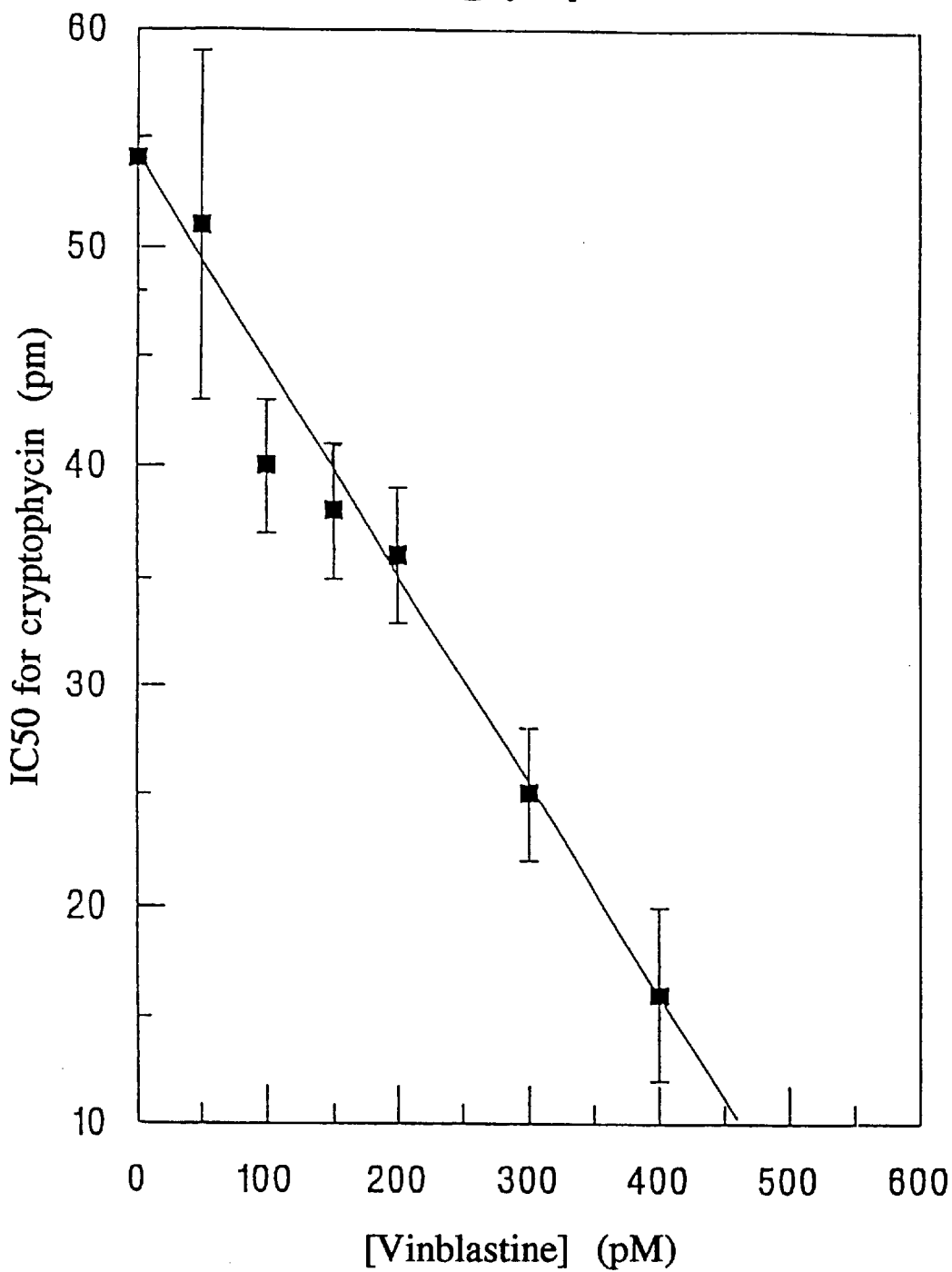
FIG. 4 provides Isobolograms for combinational effects of vinblastine and cryptophycins on cell proliferation. SKOV3 cells were treated with vinblastine (0–600 pM) and/or cryptophycins (1–100 pM) for 48 hours. Cell numbers were then determined by SRB staining as described in the Experimental Section, and the IC$_{50}$s (■) and the line of additivity ( - - - ) for combinations of vinblastine and cryptophycin compounds. Values represent the means for two experiments each containing triplicate samples.

SKOV3 cells were treated with combinations of cryptophycins and vinblastine for 48 hours. The percentages of surviving cells were then determined and the $IC_{50}$s for each combination was calculated. The effects of these combinational treatments, as well as single drug treatments, are depicted as an isobologram (FIG. 4). The $IC_{50}$s for combinations of cryptophycin compounds and vinblastine fell very close to the line of additivity, indicating that these two drugs induce only additive inhibitions of cell proliferation.

Toxicity of cryptophycins, vinblastine and taxol toward SKOV3 and SKVLB1 cells

SKVLB1 cells are resistant to natural product anticancer drugs because of their over expression of P-glycoprotein[12]. The abilities of taxol, vinblastine and cryptophycin compounds to inhibit the growth of SKOV3 and SKVLB1 cells are summarized in Table 5. Taxol caused dose-dependent inhibition of the proliferation of both cell lines with $IC_{50}$s for SKOV3 and SKVLB1 cells of 1 and 8000 nM, respectively. Vinblastine also inhibited the growth of both cell lines, with $IC_{50}$s of 0.35 and 4200 nM for SKOV3 and SKVLB1 cells, respectively. Cryptophycins demonstrated $IC_{50}$s of 7 and 600 pM for SKOV3 and SKVLB1 cells, respectively. The resulting resistance factors for SKVLB1 cells to the compounds are calculated as the $IC_{50}$s for SKVLB1. $IC_{50}$s for SKOV3 cells are also indicated in Table 5.

|  | Cell Line | | |
| --- | --- | --- | --- |
| Compound | SKOV3 | SKVLB | Resistance Factor |
| | $IC_{50}$ (nM) | | |
| Vinblastine | 0.35 ± 0.25 | 4200 ± 1700 | 12,000 |
| Taxol | 1 ± 0.4 | 8000 ± 2000 | 8,000 |
| Cryptophycins | 0.007 ± 0.002 | 0.60 ± 0.19 | 86 |

Thus it is demonstrated that the present invention provides novel cryptophycin compounds, as well as previously-disclosed cryptophycin compounds, which are potent inhibitors of cell proliferation, acting by disruption of the microtubule network and inhibition of mitosis. The cryptophycin compounds disrupt microtubule organization and thus normal cellular functions, including those of mitosis.

Classic anti-microtubule agents, such as colchicine and Vinca alkaloids, arrest cell division at mitosis. It seemed appropriate to compare the effect of one of these agents on cell proliferation with the cryptophycin compounds. For this purpose, the Vinca alkaloid vinblastine was selected as representative of the classic anti-microtubule agents. Accordingly, the effect of cryptophycin compounds and vinblastine on the proliferation and cell cycle progression of the Jurkat T-cell leukemia cell line was compared. Both compounds caused parallel dose-dependent inhibitions of cell proliferation and accumulation of cells in mitosis.

Since antimitotic effects are commonly mediated by disruption of microtubules in the mitotic spindles, the effects of cryptophycin compounds on cytoskeletal structures were characterized by fluorescence microscopy. Immunofluorescence staining of cells treated with either a cryptophycin compound or vinblastine clearly demonstrated that both compounds caused the complete loss of microtubules. Similar studies with SKOV3 cells demonstrate that the anti-microtubule effects of cryptophycin compounds are not unique to the smooth muscle cell line. Neither drug affected the levels or distribution of microfilament bundles, as was readily induced by cytochalasin B, indicating that the loss of microtubules may not be due to a non-specific mechanism, e.g. activation of proteases or loss of energy charge. Both vinblastine and cryptophycin compounds also promote marked collapse of vimentin intermediate filaments, such that brightly staining rings were formed around the cell nucleus.

Removal of vinblastine from the culture medium resulted in rapid repolymerization of microtubules. In contrast, cells treated with cryptophycin compounds remained depleted of microtubules for at least 24 hours after the compound was removed from the cultures.

The present invention demonstrates that cryptophycin compounds circumvent P-glycoprotein-mediated multiple drug resistance. Transport by P-glycoprotein limits the ability of natural product anticancer drugs to inhibit the growth of tumor cells with acquired or de novo drug resistance.[13–15] Vinca alkaloids, while very useful in the initial course of chemotherapy, are extremely good substrates for transport by P-glycoprotein, and so are of very limited usefulness against P-glycoprotein-mediated MDR tumors. Therefore, identification of agents which overcome multiple drug resistance may, should lead to the development of useful and novel anticancer agents. The cryptophycin compounds of the present invention appear to be such agents since they are poor substrates for P-glycoprotein-mediated transport. This fact is reflected in the low cell resistance factor for cryptophycin compounds compared with vinblastine, taxol and other natural product drugs.

All publications and patent applications cited in this specification, but not individually and specifically incorporated by reference, are herein incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

References

1. Eglof, G., *Organic Chemistry: An Advanced Treatise,* Gilmar et al. (ed.), pp. 31–46, John Wiley & Sons (1943).
2. Kemp, et al., *Organic Chemistry,* Worth Publishers, Inc. (1980).
3. Patterson, G. M. L. et al. *J. Phycol.* 27:530–6 (1991).
4. Corbett, T. H. et al. *Cytotoxic Anticancer Drugs: Models and Concepts for Drug Discovery and Development,* pp 35–87; Kluwer Academic Publishers: Norwell, 1992.
5. Valeriote, F. A. et al. *Discovery and Development of Anticancer Agents;* Kluwer Academic Publishers: Norwell, 1993; in press.
6. Schwartz, R. E. et al. *J. Ind. Microbiol.* 5:113–24 (1990).
7. Hirsch, C. F. et al. U.S. Pat. No. 4,946,835, issued Aug. 7, 1990.
8. Sesin, D. F. U.S. Pat. No. 4,845,085, issued Jul. 4, 1989.
9. Sesin, D. F.; Liesch, J. M. U.S. Pat. No. 4,868,208, issued Sep. 19, 1989.
10. Sesin, D. F. U.S. Pat. No. 4,845,086, issued Jul. 4, 1989.
11. Skehan, P. et al., *J. Natl. Cancer Inst.* 82: 1107–1112 (1990).
12. Bradley, G. et al. *Cancer Res.* 49: 2790–2796 (1989).
13. Endicott, J. A. et al. *Ann. Rev. Biochem.* 58: 137–171 (1989).
14. Beck, W. T. *Biochem. Pharm.* 36: 2879–2887 (1987).
15. Moscow, J. A. et al. *J. Natl. Cancer Inst.* 80: 14–20 (1988).

What is claimed is:

1. A cryptophycin represented by the structure:

wherein:
$R_1$ is H or a halogen;
$R_2$ is H, an oxygen of ketone or OH; or
$R_1$ and $R_2$ may be taken together to form an epoxide ring; or $R_1$ and $R_2$ may be taken together to form an episulfide ring;
$R_3$ is H, or a lower alkyl group;
$R_4$ is H or OH;
$R_5$ is H or OH; or
$R_4$ and $R_5$ may be taken together to form a bond;
$R_6$ is H or a halogen;
with the following proviso:
when $R_1$ and $R_2$ are taken together to form an epoxide group, $R_4$ and $R_5$ are taken together to form a bond and $R_6$ is chlorine, $R_3$ is not methyl.

2. A pharmaceutical composition useful for inhibiting proliferation of a hyperproliferative mammalian cell comprising an effective amount of a compound with the following structure:

wherein:
$R_1$ is H or a halogen;
$R_2$ is H, an oxygen of ketone or OH; or
$R_1$ and $R_2$ may be taken together to form an epoxide ring; or $R_1$ and $R_2$ may be taken together to form an episulfide ring;
$R_3$ is H, or a lower alkyl group;
$R_4$ is H or OH;
$R_5$ is H or OH; or
$R_4$ and $R_5$ may be taken together to form a bond; $R_6$ is H or a halogen; With the following proviso
when $R_1$ and $R_2$ are taken together to form an epoxide group, $R_4$ and $R_5$ are taken together to form a bond and $R_6$ is chlorine, $R_3$ is not methyl.

3. The pharmaceutical composition of claim 2 further comprising at least one anti-mitotic antitumor agent in addition to said compound.

4. The composition of claim 3, wherein said anti-mitotic antitumor agent is selected from agents which inhibit formation of microtubules by sequestering tubulin, agents which induce formation of paracrystalline aggregates of tubulin or agents which promote the polymerization of tubulin.

5. The composition of claim 3, wherein said anti-mitotic antitumor agent is selected from colchicine, colcemid, vinblastine, vincristine or taxol.

* * * * *

UNITED STATES PATENT AND TRADEMARK OFFICE
CERTIFICATE OF CORRECTION

PATENT NO. : 5,952,298
DATED : September 14, 1999
INVENTOR(S) : Richard E. Moore, et al.

It is certified that error appears in the above-identified patent and that said Letters Patent is hereby corrected as shown below:

At column 64, line 40, claim 2, please delete "R$_3$ is not methyl." and insert therefor -- R$_3$ is not methyl; together with a pharmaceutically acceptable carrier--.

Signed and Sealed this

Eighth Day of May, 2001

Attest:

NICHOLAS P. GODICI

Attesting Officer

Acting Director of the United States Patent and Trademark Office